US009604957B2

(12) United States Patent
Chang et al.

(10) Patent No.: US 9,604,957 B2
(45) Date of Patent: Mar. 28, 2017

(54) SELECTIVE MATRIX METALLOPROTEINASE INHIBITORS

(71) Applicant: University of Notre Dame du Lac, Notre Dame, IN (US)

(72) Inventors: Mayland Chang, Granger, IN (US); Shahriar Mobashery, Granger, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 15/120,508

(22) PCT Filed: Feb. 20, 2015

(86) PCT No.: PCT/US2015/016950
§ 371 (c)(1),
(2) Date: Aug. 19, 2016

(87) PCT Pub. No.: WO2015/127302
PCT Pub. Date: Aug. 27, 2015

(65) Prior Publication Data
US 2017/0015647 A1 Jan. 19, 2017

Related U.S. Application Data

(60) Provisional application No. 61/942,516, filed on Feb. 20, 2014, provisional application No. 62/088,380, filed on Dec. 5, 2014.

(51) Int. Cl.
*C07D 331/02* (2006.01)
*C07D 303/34* (2006.01)

(52) U.S. Cl.
CPC ......... *C07D 331/02* (2013.01); *C07D 303/34* (2013.01)

(58) Field of Classification Search
CPC ............................ C07D 331/02; C07D 303/34
See application file for complete search history.

(56) References Cited

U.S. PATENT DOCUMENTS

| | | |
|---|---|---|
| 6,025,150 A | 2/2000 | Livant |
| 6,166,084 A | 12/2000 | Bloor |
| 6,555,118 B1 | 4/2003 | Niazi |
| 6,600,057 B2 | 7/2003 | Quirk |
| 6,703,415 B2 | 3/2004 | Mobashery et al. |
| 7,144,917 B2 | 12/2006 | Mobashery et al. |
| 7,320,783 B2 | 1/2008 | Livant |
| 7,402,571 B2 | 7/2008 | Tennenbaum et al. |
| 7,727,520 B2 | 6/2010 | Ferguson |
| 7,879,798 B1 | 2/2011 | Aufseeser |
| 7,928,127 B2 | 4/2011 | Lee et al. |
| 7,981,426 B2 | 7/2011 | Kim |
| 7,993,665 B2 | 8/2011 | Colin et al. |
| 8,012,947 B2 | 9/2011 | Tomic et al. |
| 8,093,287 B2 | 1/2012 | Lee et al. |
| 8,129,341 B2 | 3/2012 | Gold et al. |
| 8,247,384 B2 | 8/2012 | Green et al. |
| 8,889,615 B2 | 11/2014 | Tomic-Canic et al. |
| 2002/0037916 A1 | 3/2002 | Mobashery et al. |
| 2007/0232541 A1 | 10/2007 | Reiter et al. |
| 2009/0068251 A1 | 3/2009 | Tomic et al. |
| 2011/0224275 A1 | 9/2011 | Lee et al. |
| 2011/0293643 A1 | 12/2011 | Wilkes |
| 2012/0052110 A1 | 3/2012 | Tomic et al. |
| 2013/0052184 A1 | 2/2013 | Chang et al. |

FOREIGN PATENT DOCUMENTS

| WO | 2006/125208 A1 | 11/2006 |
|---|---|---|
| WO | 2011/026107 A1 | 3/2011 |

OTHER PUBLICATIONS

Lee et al. ACS Med. Chem. Lett. 2012, 3, 490-495.*
Armstrong et al., "The Role of Matrix Metalloproteinases in Wound Healing", Journal of the American Podiatric Medical Association, vol. 92, No. 1, 2002; pp. 12-18, Research Gate.
Brown et al., "Potent and Selective Mechanism-Based Inhibition of Gelatinases", Journal of the American Chemical Society, vol. 122, No. 28; Jun. 30, 2000; pp. 6799-6800; American Chemical Society.
Chen et al., "Molecular and Mechanistic Validation of Delayed Healing Rat Wounds as a Model for Human Chronic Wounds", Wound Repair and Regeneration, vol. 7, No. 6, Nov. 1999, pp. 486-494; The Wound Healing Society.
Cui et al., "Inhibition of MMP-9 by a Selective Gelatinase Inhibitor Protects Neurovasculature from Embolic Focal Cerebral Ischemia", Molecular Neurodegeneration, vol. 7, No. 21, 2012, pp. 1-15, BioMed Central Ltd.
Fisher et al., "Recent Advances in MMP Inhibitor Design", Cancer and Metastasis Reviews, vol. 25, 2006, pp. 115-136, Springer Science and Business Media, LLC.
Forbes et al., "Active Site Ring-Opening of a Thiirane Moiety and Picomolar Inhibition of Gelatinases", Chemical Biology & Drug Design, vol. 74, Aug. 2009, pp. 527-534, John Wiley & Sons A/S.
Gu et al., "A Highly Specific Inhibitor of Matrix Metalloproteinase-9 Rescues Laminin from Proteolysis and Neurons from Apoptosis in Transient Focal Cerebral Ischemia", The Journal of Neuroscience, vol. 25, No. 27, Jul. 6, 2005; pp. 6401-6408; Society for Neuroscience.
Gutierrez-Fernandez et al., "Increased Inflammation Delays Wound Healing in Mice Deficient in Collagenase-2 (MMP-8)", The FASEB Journal, vol. 21, No. 10, Aug. 2007, pp. 2580-2591.

(Continued)

*Primary Examiner* — Matthew Coughlin
(74) *Attorney, Agent, or Firm* — Haukaas Fortius PLLC; Michael H. Haukaas

(57) ABSTRACT

The invention provides compounds, compositions, and methods for the treatment of diseases, disorders, or conditions that are modulated by matrix metalloproteinases (MMPs). The compounds can be selective MMP inhibitors, for example, selective inhibitors of MMP-2, MMP-9, and/or MMP-14. The disease, disorder, or condition can include, for example, stroke, neurological disorders, ophthalmological disorders, or wounds, such as chronic wounds or diabetic wounds.

25 Claims, 9 Drawing Sheets

(56) References Cited

OTHER PUBLICATIONS

Gooyit et al., "Selective Water-Soluble Gelatinase Inhibitor Prodrugs", Journal of Medicinal Chemistry, vol. 54, Aug. 25, 2011; pp. 6676-6690; ACS Publications, American Chemical Society.

Gooyit et al., "Selective Gelatinase Inhibitor Neuroprotective Agents Cross the Blood-Brain Barrier", ACS Chemical Neuroscience, vol. 3, Jul. 30, 2012; pp. 730-736; ACS Publications, American Chemical Society.

Gooyit et al., "O-Phenyl Carbamate and Phenyl Urea Thiiranes as Selective Matrix Metalloproteinase-2 Inhibitors that Cross the Blood-Brain Barrier", Journal of Medicinal Chemistry, vol. 56, Sep. 12, 2013; pp. 8139-8150; ACS Publications, American Chemical Society.

Gooyit et al., "A Chemical Biological Strategy to Facilitate Diabetic Wound Healing", ACS Chemical Biology 2014, vol. 9; Sep. 20, 2013; pp. 105-110; ACS Publications, American Chemical Society.

Harsha et al., "ADAM12: a Potential Target for the Treatment of Chronic Wounds", Journal of Molecular Medicine (Berlin), vol. 86, No. 8, Aug. 2008, pp. 961-969, National Institutes of Health Public Access,14 pgs.

Hadass et al., "Selective Inhibition of Matrix Metalloproteinase-9 Attenuates Secondary Damage Resulting from Severe Traumatic Brain Injury", PLoS One, vol. 8, No. 10, e76904; Oct. 23, 2013; pp. 1-14; Open Access <www.plosone.org>.

Hesek et al., "Design and Characterization of a Metalloproteinase Inhibitor-Tethered Resin for the Detection of Active MMPs in Biological Samples", Chemistry & Biology, vol. 13, Apr. 21, 2006; pp. 379-386; Elsevier Ltd.

Hesek et al., "Synthesis of an Inhibitor-Tethered Resin for Detection of Active Matrix Metalloproteinases Involved in Disease", Journal of Organic Chemistry, vol. 71, No. 16, Jul. 11, 2006; pp. 5848-5854; American Chemical Society.

Lee et al., "Metabolism of a Highly Selective Gelatinase Inhibitor Generates Active Metabolite", Chemical Biology & Drug Design, vol. 70; Sep. 2007, pp. 371-382, Blackwell Munksgaard.

Lee et al., "Structure-Activity Relationship for Thirane-Based Gelatinase Inhibitors", ACS Medicinal Chemistry Letters, vol. 3, May 2, 2012; pp. 490-495; ACS Publications, American Chemical Society.

Pradhan et al., "Wound-Healing Abnormalities in Diabetes and New Therapeutic Interventions", Diabetic Foot, US Endocrine Disease, 2007, pp. 68-72, Touch Briefings.

Song et al., "Water-Soluble MMP-9 Inhibitor Prodrug Generates Active Metabolites That Cross the Blood-Brain Barrier", ACS Chemical Neuroscience, vol. 4; May 20, 2013; pp. 1168-1173; ACS Publications, American Chemical Society.

Toth et al., "Tissue Inhibitor of Metalloproteinase (TIMP)-2 Acts Synergistically with Synthetic Matrix Metalloproteinase (MMP) Inhibitors but not with TIMP-4 to Enhance the (Membrane Type 1)-MMP-Dependent Activation of Pro-MMP-2", The Journal of Biological Chemistry, vol. 275, No. 52, Dec. 29, 2000; pp. 41415-41423; The American Society for Biochemistry and Molecular Biology, Inc.

U.S. Patent and Trademark Office as International Searching Authority, "International Search Report and Written Opinion for patent application No. PCT/US2015/016950," May 20, 2015; 9 pgs.; published by International Bureau of WIPO (World Intellectual Property Organization).

Zhang et al., "Role of Matrix Metalloproteinases and Therapeutic Benefits of Their Inhibition in Spinal Cord Injury", Neurotherapeutics: The Journal of American Society for Experimental NeuroTherapeutics, Apr. 1, 2011; 15 pgs.; Springerlink.com.

Zhou et al., "QM/MM Studies of the Matrix Metalloproteinase 2 (MMP2) Inhibition Mechanism of (S)-SB-3CT and Its Oxirane Analogue", Journal of Chemical Theory and Computation, vol. 6, No. 11, Jul. 10, 2010; pp. 3580-3587; American Chemical Society.

* cited by examiner

SELECTIVE MATRIX METALLOPROTEINASE INHIBITORS

RELATED APPLICATIONS

This application is a National Stage entry under 35 U.S.C. §371 of International Patent Application No. PCT/US2015/016950 which claims priority under 35 U.S.C. §119(e) to U.S. Provisional Patent Application No. 61/942,516 filed Feb. 20, 2014, and 62/088,380 filed Dec. 5, 2014, which applications are incorporated by reference.

BACKGROUND OF THE INVENTION

Matrix metalloproteinases (MMPs) are a group of 26 endoproteases that cleave components of the extracellular matrix. MMPs exist in their inactive zymogen (proMMP) forms, requiring activation by disruption of the complex between the cysteine residue in the prodomain and the zinc atom in the catalytic domain. MMP activity is regulated predominantly by endogenous inhibitors called tissue inhibitors of metalloproteinases (TIMPs). MMPs play roles in a wide variety of processes, ranging from cell death, differentiation, proliferation, cell signaling and migration, angiogenesis, wound healing, and tissue remodeling. When the activities of MMPs are imbalanced or uncontrolled, MMPs may play important roles in pathological processes, such as tumor metastasis and inflammation. MMPs also play roles in the development and repair of the central nervous system (CNS), as well as in the pathology of many neurological diseases.

Numerous studies implicating MMPs in cancer pathology resulted in evaluation of broad-spectrum MMP inhibitors in clinical trials in patients with advanced cancer. The compounds tested contained hydroxamate groups that chelate to zinc, and as such, inhibit MMPs and often other zinc-dependent enzymes broadly. Clinical trials with these broad-spectrum MMP inhibitors failed to extend survival. Moreover, toxic side effects, such as musculoskeletal pain and inflammation, were observed. The toxicities were attributed to the poor selectivity of the inhibitors. In addition, broad-spectrum MMP inhibitors advanced to clinical trials without adequate target validation. It is now recognized that some MMPs are essential for tumor progression and metastasis, but others play host-protective functions. Thus, the strategy of broad inhibition of MMPs is problematic. Numerous studies indicate that neurological conditions would benefit from MMP inhibitors, however selective MMP inhibitors are necessary. This is critical, as disparate MMPs mediate different roles. Some exert the desirable repair functions in disease, yet others promote the deleterious pathological consequences of neurological diseases.

A well-studied subgroup of MMPs is the gelatinases: MMP-2 (gelatinase A) and MMP-9 (gelatinase B). ProMMP-2 is present constitutively and is activated by MMP-14, while MMP-9 is inducible and is activated by MMP-3, plasmin, or under oxidative stress conditions. Gelatinases, in particular MMP-9, play roles in many pathological CNS conditions, with disruption of the blood-brain barrier (BBB) occurring in many neurological diseases. Following cerebral ischemia, activation of MMP-2 leads to disruption of the BBB, followed by a second wave of damage to the BBB after reperfusion, which is mediated by MMP-9.

Treatment with the selective gelatinase inhibitor SB-3CT (compound 1) rescues laminin from proteolysis and neurons from apoptosis following transient focal cerebral ischemia and protected the neurovasculature from embolic focal cerebral ischemia. Disruption of the BBB is observed after traumatic brain injury, which has been attributed to MMP-9 and aquaporin-4 (AQP4). Selective inhibition of MMP-9 with compound 1 attenuated secondary damage resulting from severe traumatic brain injury in mice. In mice expressing mutant superoxide dismutase (SOD1) that causes amyotrophic lateral sclerosis, reduction of MMP-9 by gene ablation, viral gene therapy, or chemical inhibition with the tetrapeptidyl hydroxamic acid FN-439, delayed muscle denervation, indicating that MMP-9 plays a major role in motor neuron degeneration. After spinal cord injury, elevated MMP-9 in the lumbar cord contributes to failure of motor relearning in mice and deletion of MMP-9 reduces inflammation in the lumbar cord and results in improved recovery.

MMP-9 also plays a role in epilepsy. In pentylenetetrazole-induced epilepsy, sensitivity to epileptogenesis decreases in mice lacking the MMP-9 gene and increases in rats overexpressing MMP-9, and MMP-9 deficiency diminishes seizures. MMP-9 significantly contributes to cell death after pilocarpine-induced seizures in the developing brain. Treatment with the broad-spectrum MMP inhibitor GM6001 mitigates cell death in pilocarpine-induced seizures in immature rats, and in the pathophysiology of brain injury following seizures. MMP-1, MMP-3 and MMP-9 have been implicated in BBB disruption in West Nile virus encephalitis. Treatment with the broad-spectrum MMP inhibitor GM6001 reversed West Nile virus-induced BBB disruption. These studies implicate gelatinases in various pathophysiological processes in the CNS. Thus, selective potent inhibitors of gelatinases that cross the BBB are highly sought.

Development of therapeutics that target CNS diseases requires that the drugs be delivered to the target site, the brain. However, the BBB is a major challenge to the development of CNS-active small-molecule therapeutics, constituting a physical barrier that prevents the transport of substances from the blood into the CNS. Small molecules are transported across the BBB by lipid-mediated transport, if they have a molecular weight of less than 400 Da and/or high lipid solubility. In practice, a very small number of drugs for CNS diseases fit these criteria. This is due to the fact that the water solubility of a drug is an important physical property that affects the absorption, distribution, metabolism, and excretion of drugs, as well as whether the compounds can be screened in a high-throughput manner. While it is assumed that lipophilic small molecules can be transported across the BBB, more than 98% of small-molecule drugs do not cross the BBB. Water-soluble drugs can be lipidized by blocking hydrogen-bond forming functional groups. An example is acetylation of the two hydroxyl groups in morphine to heroin, which increases BBB penetration 100-fold. However, very few CNS drugs have been developed by lipidization of water-soluble drugs, as functional groups are often metabolized in vivo. Alternatively, a water-soluble drug may be chemically modified to increase its affinity for carrier-mediated BBB transporters.

Not only must a CNS drug cross the BBB, but it must achieve therapeutic concentrations in the brain and be cleared from the brain so that the drug does not cause CNS side effects due to accumulation. As a result, CNS drugs have the highest attrition rate in development. Thus, new inhibitors of gelatinases that cross the BBB, that achieve therapeutic concentrations in the brain, and that can cleared from the brain are urgently needed to improve current therapies.

SUMMARY

The invention provides selective water-soluble and slow-binding matrix metalloproteinase inhibitors that cross the blood-brain barrier. The matrix metalloproteinase inhibitors can be selective MMP-2 and MMP-9 inhibitors. These inhibitors can be used for the treatment of neurological conditions and cancer, as well as for improving the healing of wounds.

Accordingly, the invention provides a compound of Formula I:

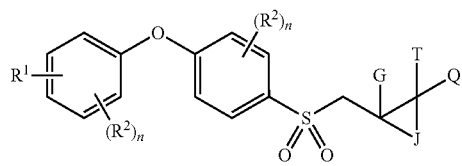
(I)

wherein
R¹ is —CH₂—NHR$^a$ wherein R$^a$ is H or (C₁-C₆)alkanoyl; —NH—C(=NH)—NH₂; or

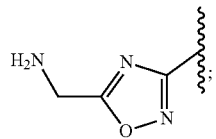

J is S or O;
G, T, and Q are each independently H, (C₁-C₆)alkyl, or —CN;
each R² is independently H, OH, (C₁-C₆)alkyl, (C₁-C₆)alkoxy, (C₁-C₆)alkanoyl, (C₁-C₆)alkanoyloxy, aryl, heteroaryl, carboxy, cyano, nitro, halo, trifluoromethyl, trifluoromethoxy, SR$^z$, SO₂N(R$^z$)₂, NR$^z$R$^z$, or COOR$^z$; wherein each R$^z$ is independently H, (C₁-C₆)alkyl, (C₁-C₆)alkanoyl, (C₆-C₁₀)aroyl, aryl, aryl(C₁-C₆)alkyl, heteroaryl, heteroaryl(C₁-C₆)alkyl, or optionally a nitrogen protecting group when R$^z$ is covalently bonded to a nitrogen atom; and
each n is independently 0, 1, 2, 3, or 4;
or a salt thereof.

One value for R¹ is —CH₂—NHR$^a$.
One specific value for R$^a$ is H.
Another specific value for R$^a$ is —C(=O)CH₃ (acetyl).
One value for R¹ is —NH—C(=NH)—NH₂.
Another specific value for R¹ is

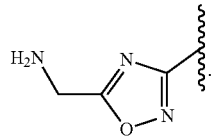 [SMILES: *c1noc(CN)n1]

In some embodiments, R¹ is located at the para position with respect to the oxygen of the phenyl group to which R¹ is attached. The variable group R¹ can be ortho, meta or para with respect to the phenoxy moiety of Formula I. In certain specific embodiments, R¹ is meta or para with respect to the phenoxy moiety of Formula I.

One specific value for J is S. Another specific value for J is O. In one embodiment, G, T, and Q are each independently H.

In another embodiment, the compound of Formula I is a compound of Formula II:

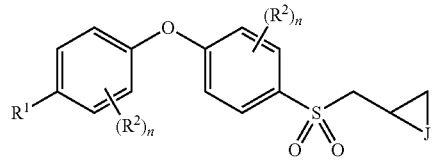
(II)

wherein R¹, R², n, and J are as defined for Formula I.
In another specific embodiment, the compound of Formula I or II is:

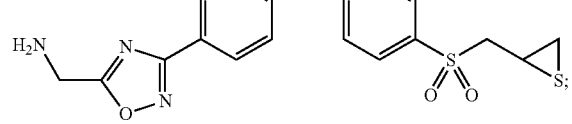
(4)

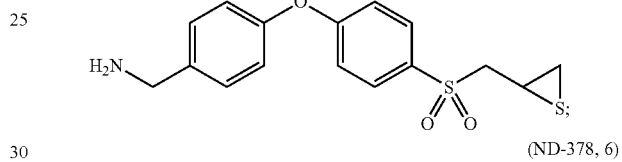
(ND-336, 5)

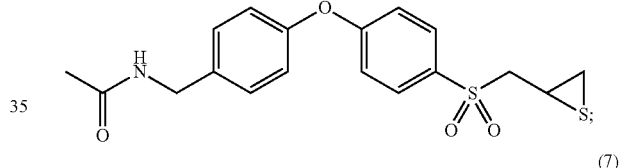
(ND-378, 6)

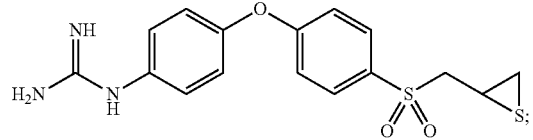
(7)

or a pharmaceutically acceptable salt thereof.

The invention further provides a composition comprising a compound of Formula I or II, in combination with a pharmaceutically acceptable diluent, excipient, or carrier. The pharmaceutical composition can be formulated for intravenous, subcutaneous, intracardiac, intramuscular, intraperatoneal, or topical administration.

The compounds described herein can be a selective inhibitors of MMP-2, MMP-9, MMP-14, or a combination thereof. For example, the compounds can inhibit MMP-2 and have a $K_i$ of less than about 3 μM. In some embodiments, the compound inhibits MMP-9 and has a $K_i$ of less than 20 μM.

The invention also provides a method to inhibit MMP-2 or MMP-9 comprising contacting a composition that includes MMP-2 or MMP-9 with a compound of Formula I, thereby inhibiting the enzymatic activity of the gelatinase.

In some embodiments, the compound can have an aqueous solubility of at least about 2.5, at least about 5, at least about 7.5, at least about 10, at least about 12.5, at least about 15, at least about 20, at least about 25, at least about 30, or at least about 40 mg/mL. In some embodiments, the compound can have an aqueous solubility of at least 2, 4, 5, 10, 20, 25, or 30 mM. In yet other embodiments, the compound has an aqueous solubility of at least about 400 times, at least about 4000 times, or at least about 5000 times that of SB-3CT, which has an aqueous solubility of about 2.45 µg/mL.

The invention further provides diagnostic methods and methods of treatment using the compounds described herein, for example, a compound of Formula I. Thus, in one embodiment, the invention provides a method to selectively inhibit a gelatinase comprising contacting the gelatinase with a compound described herein, thereby selectively inhibiting the enzymatic action of the gelatinase. In some embodiments, the inhibition is selective for MMP-2 in the presence of MMP-8. In some embodiments, the inhibition is selective for MMP-9 in the presence of MMP-8. In some embodiments, the inhibition is selective for MMP-2 in the presence of both MMP-9 and MMP-14.

In some embodiments, the compound is a nanomolar slow-binding inhibitor of MMP-2, MMP-9, and MMP-14, and the compound poorly inhibits MMP-8 in a non-competitive manner. In other embodiments, the compound inhibits MMP-2, MMP-8, MMP-9, and MMP-14. In various embodiment, the compound inhibits MMP-2 at a concentration of less than 0.7 µM. In further embodiments, the compound does not inhibit MMP-1, MMP-3, MMP-7, ADAM9, and ADAM10.

The invention also provides a method to treat a neurological condition comprising administering to a patient having a neurological condition an effective amount of a compound described herein that is effective to treat the neurological condition, thereby alleviating or lessening the symptoms of the condition. The neurological conditions can be one or more of the neurological conditions described herein.

The invention also provides a method to treat cancer comprising administering to a patient having cancer an effective amount of a compound described herein that is effective to treat the cancer, thereby killing cancer cells, inhibiting the cancer cells from proliferating, or alleviating the symptoms of the cancer. The cancer can be one or more of the cancer conditions described herein.

The invention also provides a method to treat a patient having a wound comprising administering to a patient having a wound an effective amount of a compound described herein that is effective to enhance re-epithelialization of tissues adjacent to the wound. The wound can be a chronic wound, a diabetic wound, and/or another type of wound described herein.

The invention also provides a method to treat a patient having traumatic brain injury comprising administering to a patient having traumatic brain injury an effective amount of a compound described herein that is effective to treat the traumatic brain injury, thereby lessening the symptoms of the traumatic brain injury.

In one specific embodiment, the invention provides a method for treating traumatic brain injury in a patient in need of such treatment, the method comprising administering to the patient an effective amount of a compound of Formula I. In some embodiments, the compound of Formula I is a compound of Formula II. In a specific embodiment, the compound is ND-336 or ND-378:

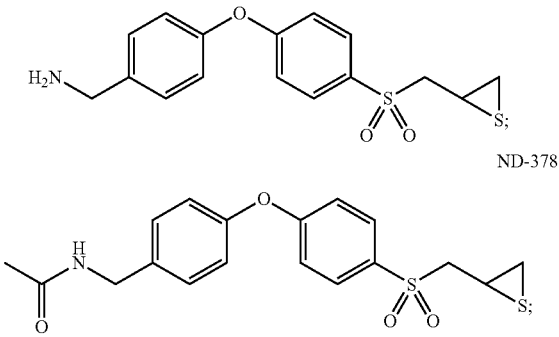

or a pharmaceutically acceptable salt thereof.

In another specific embodiment, the invention provides a method for a diabetic wound in a patient in need of such treatment, the method comprising administering to the patient an effective amount of a compound of Formula I. In some embodiments, the compound of Formula I is a compound of Formula II. In a specific embodiment, the compound is ND-336 or ND-378:

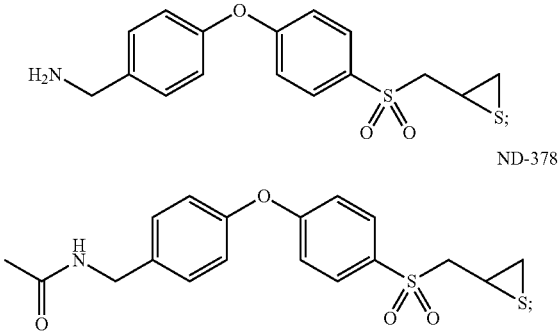

or a pharmaceutically acceptable salt thereof.

The invention thus provides for the use of the compounds and compositions described herein for use in medical therapy. The medical therapy can be treating cancer, for example, breast cancer, lung cancer, pancreatic cancer, prostate cancer, or colon cancer. The medical therapy can also be therapy for traumatic brain injury or for enhancing the healing of wounds. The invention also provides for the use of a compound or composition as described herein for the manufacture of a medicament to treat a condition or disease in a mammal, for example, cancer in a human. The medicament can include a pharmaceutically acceptable diluent, excipient, or carrier.

Accordingly, the invention provides a method of treating a disease or condition that is modulated by a matrix metalloproteinase (MMP) comprising administering to a patient in need of such treatment an effective amount of a compound of a formula described herein, so that the disease or condition is treated. The matrix metalloproteinase (MMP) can be a gelatinase (e.g., MMP-2, MMP-9, or MMP-13), a collagenase, a stromelysin, MMP-23, MMP-19, or matrilysin, and the activity of the matrix metalloproteinase can be significantly inhibited.

When the compounds, compositions, or methods of the invention are used to inhibit MMPs, the inhibition may be selective for one type of MMP over one or more others. In some embodiments, a compound can selectively inhibit MMP-2, MMP-9, and/or MMP-14. The manner of inhibition may also involve slow-binding inhibition with respect to $k_{on}$ and $k_{off}$ parameters. Accordingly, modulating a matrix metalloproteinase or inhibiting a matrix metalloproteinase includes selectively inhibiting a matrix metalloproteinase, such as MMP-2, MMP-9, and/or MMP-14, while other gelatinases, such as MMP-1, MMP-3, and/or MMP-7 are not inhibited.

The disease or condition can include any disease, disorder, or condition recited herein, including, but not limited to, cancer, stroke, a chronic wound, an ophthalmological disorder, traumatic brain injury, spinal cord injury, subarachnoid hemorrhage, tuberculosis, asthma, glaucoma, retinal ischemia, ischemic optic neuropathy, macular degeneration, sequalae of hyperhomocystinemia, convulsion, pain, aneurism, depression, anxiety, schizophrenia, muscle spasm, migraine headache, emesis, brain edema, tardive dyskinesia, AIDS-induced dementia, ocular damage, retinopathy, a cognitive disorder, or a neuronal injury associated with HIV-infection; or a gelatinase-mediated neurodegenerative disorder comprising epilepsy, Alzheimer's disease, Huntington's disease, Parkinson's disease, multiple sclerosis, or amyotrophic lateral sclerosis; or a combination thereof.

In some embodiments, the condition is ischemic stroke or hemorrhagic stroke. In another embodiment, the condition is a neurological disorder or ophthalmological disorder. The neurological disorder or ophthalmological disorder can arise from at least one of trauma, ischemic or hypoxic conditions. The neurological disorder can be a neurodegenerative disorder. In some embodiments, the disease, disorder, or condition may arise from at least one of painful neuropathy, neuropathic pain, diabetic neuropathy, depression, anxiety, movement disorders, tardive dyskinesia, cerebral infections that disrupt the blood-brain barrier, meningitis, meningoencephalitis, hypoglycemia, cerebral ischemia (stroke), cardiac arrest, spinal cord trauma, head trauma, perinatal hypoxia, or hypoglycemic neuronal damage.

The administering of a compound described herein can be carried out in combination with administering a thrombolytic agent. The thrombolytic agent can be, for example, tissue plasminogen activator (tPA).

The invention therefore provides novel compounds of Formula I, intermediates for their synthesis, as well as methods of preparing such compounds. The invention also provides compounds of the formulas described herein that are useful as intermediates for the synthesis of other useful compounds. The invention further provides for the use of compounds of Formula I for the manufacture of medicaments useful for the treatment of various conditions modulated by matrix metalloproteinases, such as stroke in a mammal.

Additionally, the invention provides compounds and compositions described herein for use in medical therapy. The invention thus provides for the use of a compound described herein to prepare a medicament to treat a disease or condition that is modulated by a matrix metalloproteinase (MMP). The medicament can include a physiologically acceptable diluent or carrier. The medical therapy can be treating a neurological disorder or cancer, such as breast cancer, lung cancer, pancreatic cancer, prostate cancer, or colon cancer. Additional diseases, disorders, and conditions that can be treated with such therapy are described herein below. The invention also provides for the use of a compound or composition described herein for the manufacture of a medicament to treat such conditions, for example, conditions in a mammal, such as a human.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
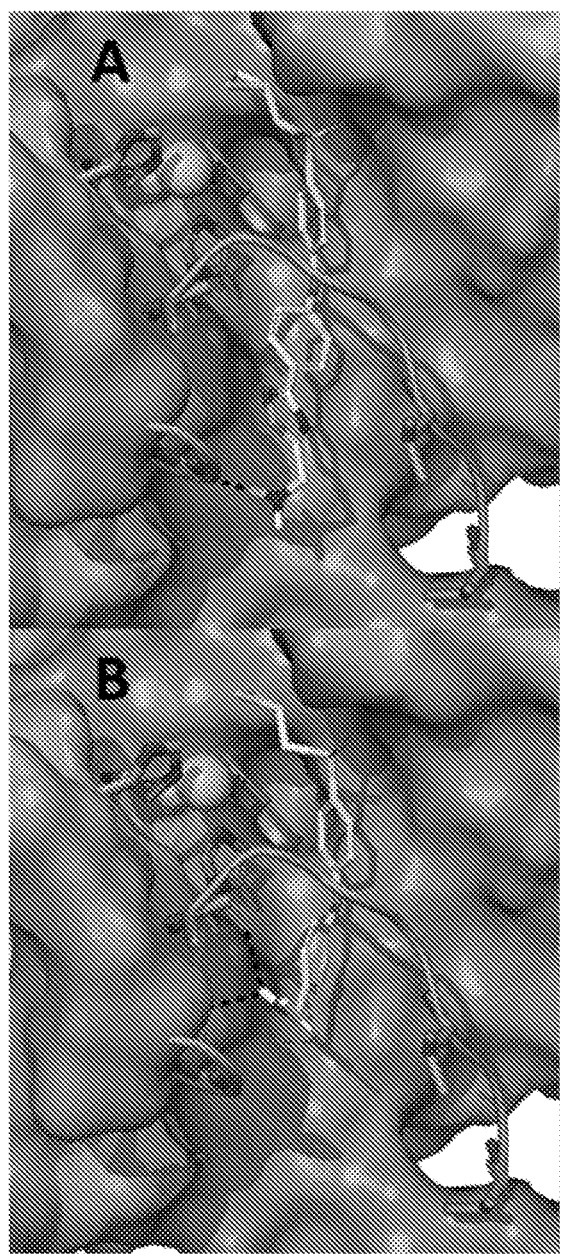
FIG. 1. Stereo view of the thiirane analogs docked to the MMP-2 catalytic site. The inhibitors are represented in capped sticks, with light gray for carbons, blue for nitrogen, red for oxygen, and yellow for sulfur. Relevant loop amino acid residues are represented in capped sticks, with purple for carbon. The zinc ion is shown in gray sphere representation. The Connolly surface was generated for the protein residues excluding that in the loop region, which covers the cavity. Hydrogen bonds between the inhibitor and the protein are shown as black dotted lines. (A) The bulky substituent in the terminal ring of inhibitor 4 is tolerated at the S1' site of MMP-2. (B) Inhibitor 6, in the absence of steric hindrance, can form favorable hydrogen bonds with the backbone carbonyl oxygen atoms of MMP-2 loop residues. The positions of the bulkier residues in other MMPs, Arg424 of MMP-9 and Gln262 and Met264 of MMP-14, are near the 5 o'clock position of the loop.

The invention may be more fully appreciated by reference to the following description, including the following glossary of terms and the concluding examples. For the sake of brevity, the disclosures of the publications, including patents, cited in this specification are herein incorporated by reference. Reference is herein made to the subject matter recited by certain claims, examples of which are illustrated in the accompanying structures and formulas. While the exemplary subject matter will be described, it will be understood that the exemplary descriptions are not intended to limit the claims. On the contrary, the inventive subject matter is intended to cover all alternatives, modifications, and equivalents, which may be included within the scope of the presently disclosed subject matter as defined by the claims.

Gelatinases (matrix metalloproteinases 2 and 9) play important roles in the pathology of many neurological diseases. A major challenge to the development of therapeutics for the treatment of neurological diseases is the inability of >98% of small-molecule drugs to cross the blood-brain barrier (BBB) and achieve therapeutic concentrations in the brain. SB-3CT (compound 1) is a selective slow-binding and potent inhibitor of gelatinases that shows efficacy in animal models of neurological diseases. However, SB-3CT is poorly water-soluble.

We synthesized and evaluated p-aminomethyloxadiazol (4), p-aminomethyl (5, ND-336), p-acetamidomethyl (6, ND-378), and p-guanidino (7) as advancements to compound 1. The compounds are 10- to 14,000-fold more water-soluble than 1, retained slow-binding inhibition behavior towards MMP-2, and crossed the BBB. The p-acetamidomethyl analog (compound 6) is a selective nanomolar slow-binding inhibitor of MMP-2, which does not inhibit the closely related MMP-9 or MMP-14. Because of the slow dissociation of compound 6 from the target MMP-2 (residence time of 6 bound to MMP-2 is 18.2±0.4 min), it results in sustained inhibition of MMP-2 even when concentrations of 6 fall below the $K_i$ value. This inhibitor is a useful tool in therapeutic intervention and in investigations of the role of MMP-2 in neurological diseases. The p-aminomethyl derivative (compound 5) is a water-soluble nanomolar slow-binding inhibitor of MMP-2, MMP-9, and MMP-14 and has residence times for inhibition of these enzymes 6- to 7-fold longer than those of the tissue inhibitors of metalloproteinase 1 or 2 (TIMP-1 or TIMP-2) bound to MMP-9, protein inhibitors that have evolved for the purpose of regulating MMPs.

DEFINITIONS

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "alkyl" refers to a straight- or branched-chain alkyl group having from 1 to about 20 carbon atoms in the chain. For example, the alkyl group can be a $(C_1-C_{20})$alkyl, a $(C_1-C_{12})$alkyl, $(C_1-C_8)$alkyl, $(C_1-C_6)$alkyl, or $(C_1-C_4)$alkyl. Examples of alkyl groups include methyl (Me), ethyl (Et), n-propyl, isopropyl, butyl, isobutyl, sec-butyl, tert-butyl (t-Bu), pentyl, isopentyl, tert-pentyl, hexyl, isohexyl, and groups that in light of the ordinary skill in the art and the teachings provided herein would be considered equivalent to any one of the foregoing examples. Alkyl groups can be optionally substituted or unsubstituted, and optionally partially unsaturated, such as in an alkenyl group.

The term "alkenyl" refers to a straight- or branched-chain alkenyl group having from 2 to 20 carbon atoms in the chain. (The double bond of the alkenyl group is formed by two $sp^2$ hybridized carbon atoms.) Illustrative alkenyl groups include $C_1-C_{12}$ alkenyl groups, such as prop-2-enyl, but-2-enyl, but-3-enyl, 2-methylprop-2-enyl, hex-2-enyl, and groups that in light of the ordinary skill in the art and the teachings provided herein would be considered equivalent to any one of the foregoing examples. Alkenyl groups can be optionally substituted or unsubstituted.

The term "cycloalkyl" refers to a saturated or partially saturated, monocyclic, fused polycyclic, or spiro polycyclic carbocycle having from 3 to 12 ring atoms per carbocycle, and can be optionally substituted or unsubstituted. In some embodiments, an alkyl group refers to a cycloalkyl group that accordingly includes a ring structure. Such alkyl groups include (cycloalkyl)-alkyl groups. Illustrative examples of cycloalkyl groups include the following entities, in the form of properly bonded moieties:

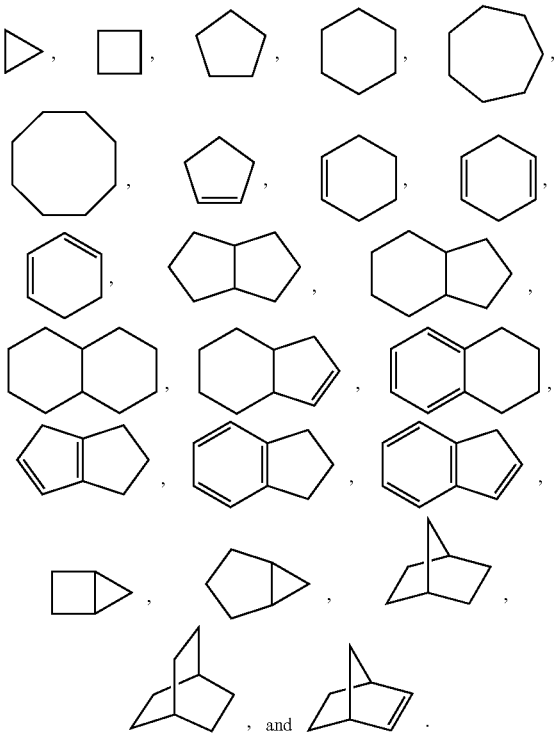

where the cycloalkyl group is attached at the location of any hydrogen atom.

A "heterocycle" or "heterocycloalkyl" group refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members, and can be optionally substituted or unsubstituted. Illustrative examples of heterocycle groups include the following entities, in the form of properly bonded moieties:

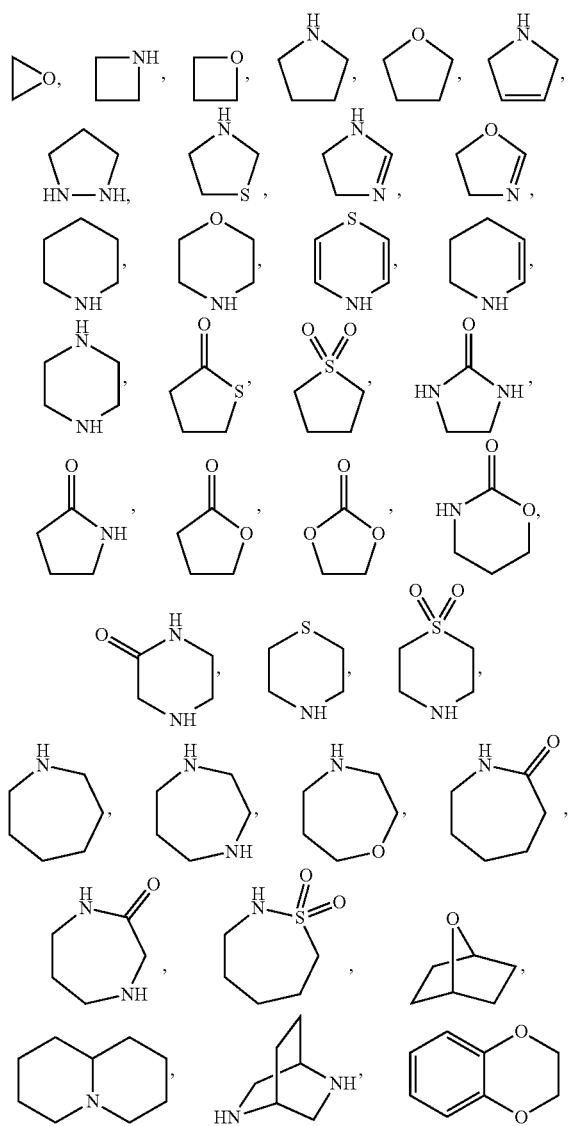

where the heterocycle group is attached at the location of any hydrogen atom.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-14 carbon atoms, about 6-13 carbon atoms, or about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. The heteroaryl can be unsubstituted or optionally substituted. Illustrative examples of heteroaryl groups include the following entities, in the form of properly bonded moieties:

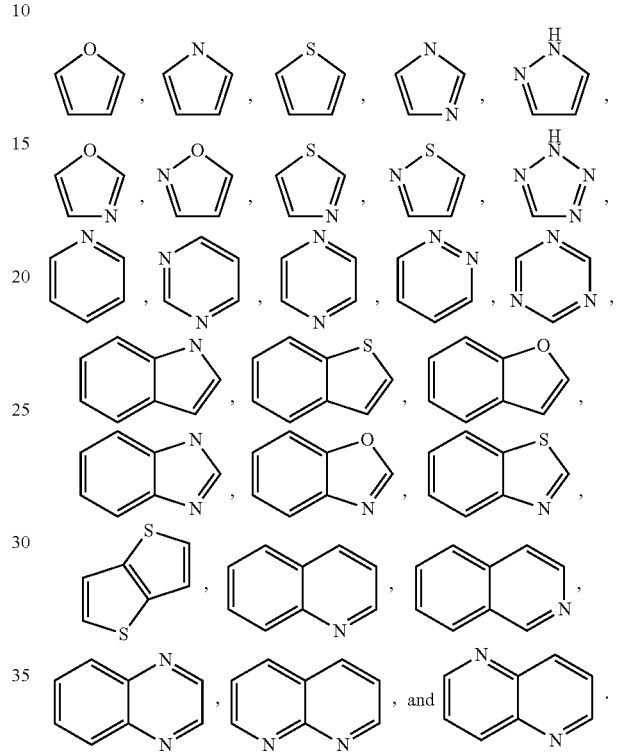

where the heteroaryl group is attached at the location of any hydrogen atom.

Those skilled in the art will recognize that the species of cycloalkyl, heterocycle, and heteroaryl groups listed or illustrated above are not exhaustive, and that additional species within the scope of these defined terms may also be selected.

As used herein, the term "Het" can refer to a 5 or 6 membered heterocyclic ring comprising 1, 2, or 3 heteroatoms selected from O, N, S, or P, wherein the ring optionally includes one or two cites of unsaturation and the ring is optionally substituted with 1, 2, or 3 oxo, halo, nitro, or methyl groups. The Het group can be a heterocycle group or a heteroaryl group. Examples include oxadiazoles, thiadiazoles, oxazoles, thiazoles, diazines, triazoles, and tetrazoles. In one embodiment, Het specifically refers to 1,3,4-oxadiazoles, 1,2,4-oxadiazoles, the isomeric 1,2,4-oxadiazoles, tetrazoles, 1,3,4-thiadiazoles, oxazoles, 1,2-diazines, thiazoles, and 1,3,4-triazoles. In another specific embodiment, Het specifically refers to 1,2-diazine, a thiazole, a 1,2,4-oxadiazole, a 1,3,4-thiadiazole, a 1,3,4-triazole, or a tetrazole. In yet another embodiment, Het specifically refers to a 1,2,4-oxadiazole, or a 1,3,4-thiadiazole. In other embodiments, Het can refer to a 5-membered heterocyclic ring wherein the ring includes three heteroatoms independently selected from O, S, P, and N. In some embodiments, at least two of the heteroatoms are N. In some embodiments, at least two of the heteroatoms are O. In yet other embodiments, Het is specifically any 1, 2, 3, 4, 5, 6, 7, or 8 groups selected from 1,3,4-oxadiazoles, 1,2,4-oxadiazoles, the isomeric 1,2,4-oxadiazoles, tetrazoles, 1,3,4-thiadiazoles, oxazoles, 1,2-diazines, thiazoles, and 1,3,4-triazoles.

The term "halogen" refers to chlorine, fluorine, bromine or iodine. The term "halo" refers to chloro, fluoro, bromo or iodo.

As to any of the groups or "substituents" described herein, each can further include one or more (e.g., 1, 2, 3, 4, 5, or 6) substituents. It is understood, of course, that such groups do not contain any substitution or substitution patterns which are sterically impractical and/or synthetically non-feasible.

The term "substituted" means that a specified group or moiety can bear one or more (e.g., 1, 2, 3, 4, 5, or 6) substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted in some embodiments but can be substituted in other embodiments. Suitable substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxy amine, hydroxyl (alkyl)amine, and/or cyano. In certain embodiments, any one of the above groups can be included or excluded from a variable or from a group of substituents.

Selected substituents within the compounds described herein may be present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis. In some embodiments, the substitution will result in a compound having a molecular weight of less than about 1200 Da, less than about 1000 Da, less than about 900 Da, less than about 800 Da, less than about 750 Da, less than about 700 Da, less than about 650 Da, less than about 600 Da, less than about 500 Da, or less than about 400 Da.

Recursive substituents are an intended aspect of the invention. One of ordinary skill in the art of medicinal and organic chemistry understands the versatility of such substituents. To the degree that recursive substituents are present in an embodiment, the total number will be determined as set forth above.

Specific values listed below for substituents (i.e., groups) and ranges are for illustration only. They do not exclude other defined values or other values within defined ranges for the substituents.

Specifically, $(C_1-C_6)$alkyl can be, for example, methyl, ethyl, propyl, isopropyl, butyl, iso-butyl, sec-butyl, pentyl, 3-pentyl, or hexyl;

$(C_1-C_6)$alkoxy can be methoxy, ethoxy, propoxy, isopropoxy, butoxy, iso-butoxy, sec-butoxy, pentoxy, 3-pentoxy, or hexyloxy;

$(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl;

$(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl;

$(C_1-C_6)$alkanoyl can be acetyl, propanoyl or butanoyl;

$(C_2-C_6)$alkanoyloxy can be acetoxy, propanoyloxy, butanoyloxy, isobutanoyloxy, pentanoyloxy, or hexanoyloxy;

$(C_3-C_8)$cycloalkyl can be cyclopropyl, cyclobutyl, cyclopentyl, cyclohexyl, cycloheptyl, or cyclooctyl;

aryl can be phenyl, indenyl, 5,6,7,8-tetrahydronaphthyl, or naphthyl; and bicyclic aryl can be indenyl or naphthyl.

Het can be heteroaryl, monocyclic heteroaryl, bicyclic heteroaryl, or a non-aromatic heterocycle. Heteroaryl can be furyl, imidazolyl, tetrazolyl, pyridyl (or its N-oxide), thienyl, pyrimidinyl (or its N-oxide), indolyl, or quinolyl (or its N-oxide); monocyclic heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl (or its N-oxide), thienyl, or pyrimidinyl (or its N-oxide); and bicyclic heteroaryl can be quinolyl (or its N-oxide); and bicyclic alkyl can be decahydroquinoline or decahydronaphthalene (cis or trans). The Het group can optionally include, for example, one or two cites of unsaturation, and the ring can optionally be substituted with 1, 2, 3, or 4 substituents, for example, oxo, halo, nitro, or methyl groups.

Any formula given herein is intended to represent compounds having structures depicted by the structural formula as well as certain variations or forms. In particular, compounds of any formula given herein may have asymmetric centers and therefore exist in different enantiomeric and/or diastereomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and/or mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

The invention also specifically includes the racemic, scalemic, R, and S mixtures and forms at the thiirane moiety of compounds of Formula A, Formula I, and their associated formulas. Accordingly, in some embodiments, the stereochemistry of the thiirane chiral center is in the R configuration, and in some embodiments, the stereochemistry of the thiirane chiral center is in the S configuration. Compounds of both configurations actively inhibit MMPs.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively.

Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to limit the definition of the moiety for the variable appearing elsewhere. In other words, where a variable appears more than once, the choice of the species from a specified list is independent of the choice of the species for the same variable elsewhere in the formula, or elsewhere in a different formula.

Various compounds of Formula I can be readily prepared using the techniques described herein, as well as those well known to those of skill in the art, including the techniques described by U.S. Pat. No. 6,703,415 (Mobashery et al.) and U.S. Pat. No. 7,928,127 (Lee et al.); PCT Publication No. WO 2011/026107 (Mobashery et al.); and U.S. Publication No. 2013/0064878 (Chang et al.).

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "selective inhibitor" as used in reference to MMPs refers to an inhibitor that inhibits the enzymatic activity of one MMP in the presence of one or more other MMPs, typically by at least one order of magnitude, for example, with respect to the Ki. The methods used to obtain $K_i$ data are known in the art and are described, for example, by Brown et al., *J. Amer. Chem. Soc.* 2000, 122(28), 6799-6800, and the references cited therein. Additional useful assays and techniques are described in U.S. Patent Publication No. 2009/0209615 (Lipton et al.), which is incorporated herein by reference in its entirety.

The term "mammal" refers to a class of vertebrate animals of more than 15,000 species, including humans, distinguished by self-regulating body temperature, hair, and in the females, milk-producing mammae. Mammals include primates, humans, rodents, canines, felines, bovines, ovines, equines, swine, caprines and the like. Specifically, mammal can be a human.

Selective Water-Soluble and Slow-Binding Matrix Metalloproteinase-2 and -9 Inhibitors that Cross the Blood-Brain Barrier.

Evidence is accumulating that damage to neurons and apoptotic death of neurons play a role in the pathogenesis of many conditions and disorders, including acute and chronic neurologic disorders. These disorders range from acute stroke, head trauma, and epilepsy to more chronic conditions such as Huntington's disease, Alzheimer's disease, HIV-associated dementia, multiple sclerosis, and glaucoma. A contributing factor to several of these diseases is the activation of matrix metalloproteinases (MMPs) in the extracellular matrix.

MMPs constitute a family of extracellular soluble or membrane-bound proteases that are prominently involved in remodeling the extracellular matrix. MMP-9 in particular is significantly elevated in humans after stroke, which is the third leading cause of death in the United States. It is also the primary cause of long-term disability. Acute ischemic stroke, the most common form of stroke, is caused by clotting in the cerebral arteries leading to brain oxygen deprivation and cerebral infarction. Gelatinases (e.g., MMP-2 and MMP-9) are known to be involved in neuronal cell death, blood-brain barrier breakdown and hemorrhage. The only FDA-approved drug for the treatment of ischemic stroke is tissue plasminogen activator (tPA), a thrombolytic agent. The administration of tPA has to be within three hours of the onset of stroke, resulting in its applicability to less than 5% of stroke patients (*CNS Neurol. Disord. Drug Targets* 2008, 7, 243-53). The use of tPA is also limited by serious side effects, which include neurotoxicity and thrombolysis-associated hemorrhagic transformation, and the use of tPA is contraindicated for patients with evidence of hemorrhage or those who are taking anti-coagulant medication. Blood from stroke patients receiving tPA treatment shows elevated levels of MMP-9, and tPA was shown to activate MMP-9. Additionally, recent reports indicate that tPA upregulates MMP-9 in the brain and contributes to matrix degradation and brain damage.

Accordingly, there is a need for new therapies for the treatment of stroke, and for treatments of stroke that have fewer and/or less severe side effects than currently used therapies. There is also a need for new gelatinase inhibitors, such as selective gelatinase inhibitors, that do not have the side effects of known therapies such as tPa.

The compound SB-3CT (1) selectively inhibits gelatinases by a unique mechanism of action involving a reaction catalyzed by the target enzymes, resulting in slow-binding and tight-binding inhibition. It is not a metal chelator, as most broad-spectrum metalloprotease inhibitors are. Furthermore, compound 1 does not broadly inhibit zinc-dependent proteases, not even other closely-related MMPs. Compound 1 is rapidly absorbed and readily crosses the BBB, achieving therapeutic concentrations in the brain. However, compound 1 is poorly water-soluble and is metabolized to two major metabolites, with one retaining activity and the other being devoid of it.

Our studies on the structure-activity relationships revealed that the terminal ring of the phenoxyphenyl moiety in compound 1 tolerated substitution. One of these inhibitors, referred to as ND-322 (compound 2) is water-soluble and inhibits selectively MMP-2 and MMP-9 with $K_i$ values of 24 and 870 nM, respectively. While compound 2 crosses the BBB, the levels in the brain are below the $K_i$ value for MMP-9, requiring N-acetylation to the more potent gelatinase inhibitor ND-364 (compound 3), which achieves therapeutic concentrations in the brain.

We herein report on the syntheses, MMP kinetics, water solubility, pharmacokinetics (PK), and brain penetration of four analogs of compound 1, compounds 4-7. The compounds exhibit 10- to 14,000-fold increase in water solubility compared to 1, retain slow-binding inhibition behavior towards MMP-2, and cross the BBB. Compound 4 is 1-2 orders of magnitude more potent against MMP-2 than MMP-9 and MMP-14. The p-aminomethyl analog (compound 5) is a nanomolar slow-binding inhibitor of MMP-2, MMP-9, and MMP-14, and poorly inhibits MMP-8 in a non-competitive manner. The p-acetamidomethyl analog (compound 6) is a selective nanomolar slow-binding inhibitor of MMP-2 and does not inhibit the closely related MMP-9 or MMP-14. While the p-guanidino derivative (compound 7) is the most potent inhibitor in the series, it lacks selectivity and inhibits MMP-2, MMP-8, MMP-9, and MMP-14.

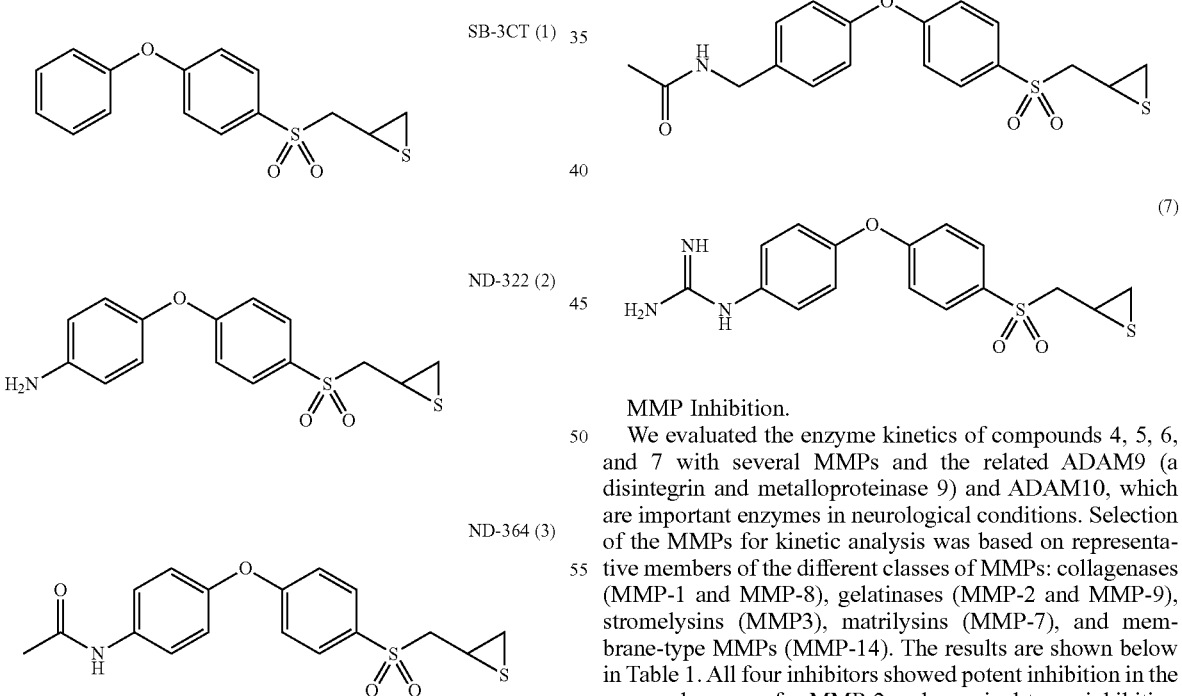

MMP Inhibition.

We evaluated the enzyme kinetics of compounds 4, 5, 6, and 7 with several MMPs and the related ADAM9 (a disintegrin and metalloproteinase 9) and ADAM10, which are important enzymes in neurological conditions. Selection of the MMPs for kinetic analysis was based on representative members of the different classes of MMPs: collagenases (MMP-1 and MMP-8), gelatinases (MMP-2 and MMP-9), stromelysins (MMP3), matrilysins (MMP-7), and membrane-type MMPs (MMP-14). The results are shown below in Table 1. All four inhibitors showed potent inhibition in the nanomolar range for MMP-2 and marginal to no inhibition of MMP-1, MMP-3, MMP-7, ADAM9, and ADAM10. The p-aminomethyloxadiazol derivative (compound 4) inhibited MMP-2, MMP-9, and MMP-14 in a slow-binding manner with $K_i$ values of 0.63±0.06 μM, 34±3 μM, and 9.4±1.1 μM, respectively. A distinctive feature of the thiirane class of MMP inhibitors is the slow-binding inhibition of the gelatinases.

TABLE 1

Kinetic Parameters and Aqueous Solubility

| | $K_i$ (μM) Enzyme | | | | | |
|---|---|---|---|---|---|---|
| Enzyme | 4 (p-oxadiazol-CH$_2$NH$_2$) | 5 (p-CH$_2$NH$_2$) | 6 (p-CH$_2$NHCOCH$_3$) | 7 (p-guanidino) | 1 (p-H) | 2 (p-NH$_2$) |
| MMP-2[a] | 0.63 ± 0.06 | 0.085 ± 0.001 | 0.23 ± 0.01 | 0.021 ± 0.002 | 0.028 ± 0.007[g] | 0.024 ± 0.015[i] |
| MMP-9[a,b] | 34 ± 3 | 0.15 ± 0.01 | 23%[c] | 0.093 ± 0.008 | 0.40 ± 0.15[g] | 0.87 ± 0.11[i] |
| MMP-14[a,b] | 9.4 ± 1.1 | 0.12 ± 0.01 | 23%[c] | 0.040 ± 0.002 | 0.11 ± 0.01[f,g] | 0.21 ± 0.02[i] |
| MMP-1[b] | 8%[d] | 4%[d] | 37%[d] | 4%[d] | 73 ± 5[f,g] | 10%[i,j] |
| MMP-3[b] | 17%[d] | 23%[d] | 14%[d] | 19 ± 1[a] | 4.0 ± 0.4[f,g] | 23.4 ± 1.6[f,i] |
| MMP-7 | 8%[d] | 1%[d] | 50%[d] | 4%[d] | 67 ± 6[g] | 16%[i,j] |
| MMP-8[b] | 24%[c] | 7.7 ± 0.1[e] | 0.69 ± 0.04[f] | 0.73 ± 0.05[f] | 2.1 ± 4[e] | 2.6 ± 0.4[e,i] |
| ADAM9 | 5%[d] | 31%[d] | 31%[d] | 14%[d] | 36%[h] | 30%[h] |
| ADAM10 | 1%[d] | 14%[d] | 8%[d] | 25%[d] | 34%[h] | 21%[k] |
| Aq. solubility (mg/mL) | 0.61 | 4.9 | 0.025 | 32 | 0.023[38] | 4.9 |

[a]$K_i$ is calculated from the ratio of $k_{off}/k_{on}$. Slow-binding kinetic parameters ($k_{on}$ and $k_{off}$ values) are given in Table 2.
[b]Catalytic domains.
[c]Inhibition at 50 μM.
[d]Inhibition at 100 μM.
[e]Linear noncompetitive mechanism.
[f]Linear competitive mechanism.
[g]Data from Lee et al. (*Chem. Biol. Drug Des.* 2007, 70, 371-382); reproduced here for the sake of comparison.
[h]Inhibition at 20 μM.
[i]Data from Gooyit et al. (*ACS Chem. Biol.* 2014, 9, 505-510); reproduced here for the sake of comparison.
[j]Inhibition at 250 μM.

Compound 4 was 54- and 15-fold more potent against MMP-2 than MMP-9 and MMP-14, respectively. The p-aminomethyl analog (compound 5) was a nanomolar slow-binding inhibitor of MMP-2, MMP-9, and MMP-14 ($K_i$ values of 0.085±0.001 μM, 0.015±0.01 μM, and 0.12±0.01 μM, respectively); it poorly inhibited MMP-8 in a noncompetitive manner ($K_i$=7.7±0.1 μM). The p-acetamidomethyl derivative (compound 6) was a potent slow-binding inhibitor of MMP-2 ($K_i$=0.23±0.01 μM), a linear competitive inhibitor of MMP-8 ($K_i$=0.69±0.04 μM), and poorly inhibited other MMPs and ADAMs, including MMP-9 and MMP-14. In contrast, the p-guanidino derivative (compound 7) was the most potent inhibitor in the series. However, it lacked selectivity and inhibited MMP-2, MMP-8, MMP-9, and MMP-14.

Computational Analysis.

Our studies on the structural-activity relationship of the thiirane class revealed that the sulfonylmethylthiirane moiety and phenoxyphenyl group are necessary for inhibition of the gelatinases; these groups are present in compounds 4-7.

To rationalize the selectivity of the inhibitors, we carried out molecular docking of the compounds to the catalytic sites of MMP-2, MMP-9, and MMP14. The caveat to this analysis is that if a rather large conformational change were to take place on inhibitor binding, we cannot account for it. Furthermore, since an X-ray structure for any MMP bound to a thiirane inhibitor does not exist presently, we have used the complex for MMP-2 bound to the thiirane generated based on quantum mechanics/molecular mechanics (QM/MM analysis). However, the results of docking explain a number of features that emerged from the inhibition analyses of these compounds with the panel of MMPs (FIG. 1).

The docked poses of the inhibitors show that the p-substituent at the terminal aryl ring fits within the S1' subsite of the MMPs. This subsite is defined by a loop that spans residues Pro417-Leu433 in MMP-2, Pro415-Leu431 in MMP-9 and Pro253-Leu271 in MMP-14, creating a cavity that accommodates the terminal ring of the inhibitors. The smaller residues Thr426 and Thr428 of the loop line the S1' site of MMP-2, which allows for occupancy by bulkier p-substituents on the inhibitors. In contrast, residues Arg424 of MMP-9 and Gln262 and Met264 of MMP-14 render the site less accessible to the larger p-substituents among these inhibitors. For example, inhibitor 4 with the bulkier p-aminomethyloxadiazole showed a 54-fold larger dissociation constant for MMP-9, likely due to the steric clash with Arg424. Arg424 has been reported as a selectivity determinant for MMP-9 inhibitors in the literature (Tochowicz et al., *J. Mol. Biol.* 2007, 371, 989-1006). The backbone amide carbonyl oxygens of the S1' loop serve as hydrogen bond donors to substituents on the inhibitors. Docked inhibitor 7 with p-guanidino substitution shows multiple potential hydrogen bonds to the backbone of all of the MMPs, which can explain why it is the most potent and non-selective compound in the series. Inhibitor 5, with the p-aminomethyl moiety, also forms similar hydrogen bonds. However, the reason for high selectivity of compound 6 for MMP-2 was not readily evident. It might be reasonable to indicate that the steric encumbrance of the S1' sites of MMP-9 and MMP-14 probably renders the p-acetamido moiety less favorable to form hydrogen bonds to the loop backbone. These findings also support the observation that the most potent inhibition by all four compounds was observed for MMP-2.

Compound 5 is 3- and 6-fold more potent inhibitor of MMP-9 than compounds 1 and 2, respectively (Table 1). While compound 4 inhibits MMP-2 preferentially over MMP-14 (15-fold), greater than one order of magnitude is preferred for therapeutic some in vivo selectivity scenarios; however, the inhibition can also be a valuable tool for diagnostic analyses. Whereas, compound 6 in vivo will inhibit MMP-2 over MMP-9; this compound will also inhibit MMP-8 to a certain extent. However, for diseases in which MMP-8 does not play a role, compound 6 will selectively or exclusively inhibit MMP-2. We had previously reported O-phenyl carbamate and phenyl urea thiiranes as selective MMP-2 inhibitors (Gooyit et al. *J. Med. Chem.* 2013, 56, 8139-8150), with $K_i$ values ranging from 240 to 760 nM. Compound 6 is a more potent MMP-2 inhibitor compared to the O-phenyl carbamate and phenyl urea thiiranes. Because compound 6 does not inhibit MMP-9 or MMP-14, it is a useful tool for ascertaining the role of MMP-2 in the pathology of diseases.

One of the most important factors in sustaining efficacy in vivo is the drug-target complex residence time, the duration in which the drug is physically bound to the target. The longer the residence time is, the longer is the duration of pharmacological effect. Residence time can be calculated as the reciprocal of the dissociation rate constant ($k_{off}$). Residence times for the inhibitors bound to MMP-2, MMP-9, and MMP-14 are given in Table 2. For MMP-2, compound 6 has the shortest residence time of 18.2±0.4 min, while compound 4 has the longest at 50.5±4.1 min. The residence times for all four compounds are longer than those for the complexes of MMP-2-TIMP-1 or MMP-2-TIMP-2, which are 7 min and 10 min, respectively (Olson et al., *J. Biol. Chem.* 1997, 272, 29975-29983). This is an important finding, as TIMPs are protein inhibitors of MMPs and have evolved for inhibition of these enzymes. In essence, these compounds are more effective in inhibition of the targeted MMPs than are TIMPs. Similarly, the residence times for compounds 4, 5, and 7 bound to MMP-9 ranged from 15.2 to 47.4 min, which were significantly longer than those for MMP-9 bound to TIMP-1 or TIMP-2 of 8 min and 7 min, respectively, and also longer than that for MMP-9 bound to compound 1 of 13.4 min. The residence times for compounds 4, 5, and 7 bound to MMP-14 were similar at 14.6±1.1, 12.6±0.3, and 16.4±0.6, respectively, and were significantly lower than those for TIMP-2 or TIMP-4 bound to MMP-14 of 83 min and 39 min, respectively. As the residence times for the thiirane inhibitors are typically significantly longer than those for the gelatinase-TIMP complexes, the thiirane inhibitors should be equally effective or better in regulating gelatinases.

TABLE 2

Residence Times for Inhibition of MMPs by the Synthetic Compounds

|  | 4 | 5 | 6 | 7 |
|---|---|---|---|---|
| MMP-2 | | | | |
| $10^3$ $k_{off}$ (s$^{-1}$) | 0.330 ± 0.027 | 0.712 ± 0.006 | 0.915 ± 0.019 | 0.507 ± 0.049 |
| $k_{on}$ (s$^{-1}$M$^{-1}$) | 521 ± 22 | 8380 ± 110 | 3910 ± 50 | 2420 ± 900 |
| residence time (min) | 50.5 ± 4.1 | 23.4 ± 0.2 | 18.2 ± 0.4 | 32.9 ± 3.2 |
| MMP-9 | | | | |
| $10^3$ $k_{off}$ (s$^{-1}$) | 1.10 ± 0.03 | 0.352 ± 0.033 | NA[a] | 0.355 ± 0.024 |
| $k_{on}$ (s$^{-1}$M$^{-1}$) | 32.0 ± 2.3 | 2360 ± 100 | NA[a] | 3820 ± 210 |
| residence time (min) | 15.2 ± 0.4 | 47.4 ± 4.4 | NA[a] | 47.0 ± 3.2 |

TABLE 2-continued

Residence Times for Inhibition of MMPs by the Synthetic Compounds

|  | 4 | 5 | 6 | 7 |
|---|---|---|---|---|
| MMP-14 | | | | |
| $10^3$ $k_{off}$ (s$^{-1}$) | 1.14 ± 0.09 | 1.33 ± 0.03 | NA[a] | 1.01 ± 0.04 |
| $k_{on}$ (s$^{-1}$M$^{-1}$) | 121 ± 11 | 10800 ± 400 | NA[a] | 25200 ± 400 |
| residence time (min) | 14.6 ± 1.1 | 12.6 ± 0.3 | NA[a] | 16.4 ± 0.6 |

[a]Not applicable

While compound 5 is 1.7-fold more potent inhibitor of MMP-2 than MMP-9, its residence time is 2-fold longer for binding to MMP-9 than to MMP-2. This indicates that when compound 5 is almost completed eliminated from the brain, its slow dissociation from MMP-9 will result in sustained inhibition of this gelatinase.

Water Solubility.

We determined the water solubility of compounds 4, 5, 6, and 7 by analyzing the filtrate of a saturated aqueous solution by ultra performance liquid chromatography (UPLC) with multiple-reaction monitoring (MRM). The results are included in Table 1 above. The guanidine analog (compound 7) is the most water-soluble inhibitor with a solubility of 32 mg/mL. The p-aminomethyl derivative (compound 5) is water soluble up to 4.9 mg/mL, while the p-aminomethyloxadiazol (4) water solubility is 0.61 mg/mL. The p-acetamidomethyl derivative (compound 6) is the least water soluble among the four, with an aqueous solubility of 0.025 mg/mL, which corresponds to more than 10-fold improvement in water solubility over compound 1. Compared to compound 2, addition of a methylene group to give compound 5 did not decrease water solubility.

The increased water solubility of inhibitors 5 and 7 makes them amenable to intravenous (iv) administration, the preferred route in acute neurological diseases, such as stroke and traumatic brain injury.

Pharmacokinetics and Brain Distribution.

Figure 2:
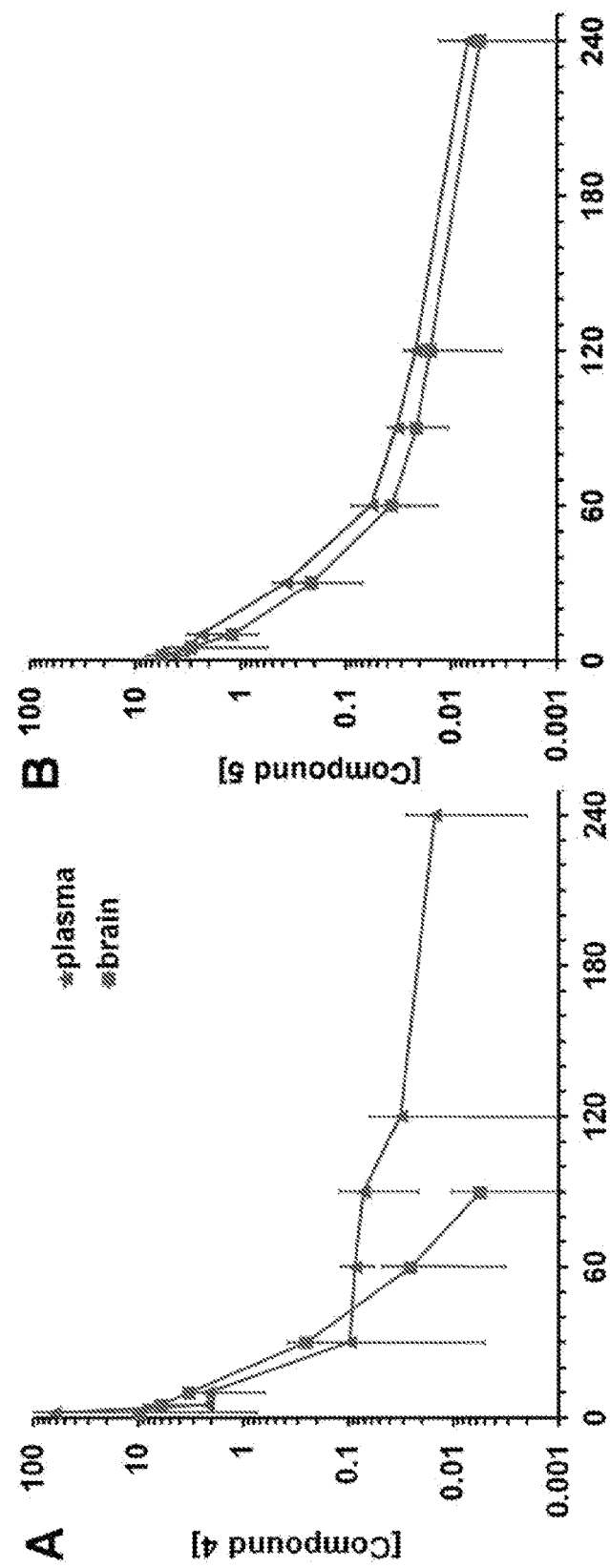
FIG. 2. Plasma and brain concentration-time curves in mice after single iv dose administration at 5 mg/kg of (A) compound 4; (B) compound 5; (C) compound 6; and (D) compound 7. Concentrations in μM for plasma (triangle data point symbols) and in pmol/mg tissue for brain (square data point symbols). The x-axis is time in minutes.
Figure 2:
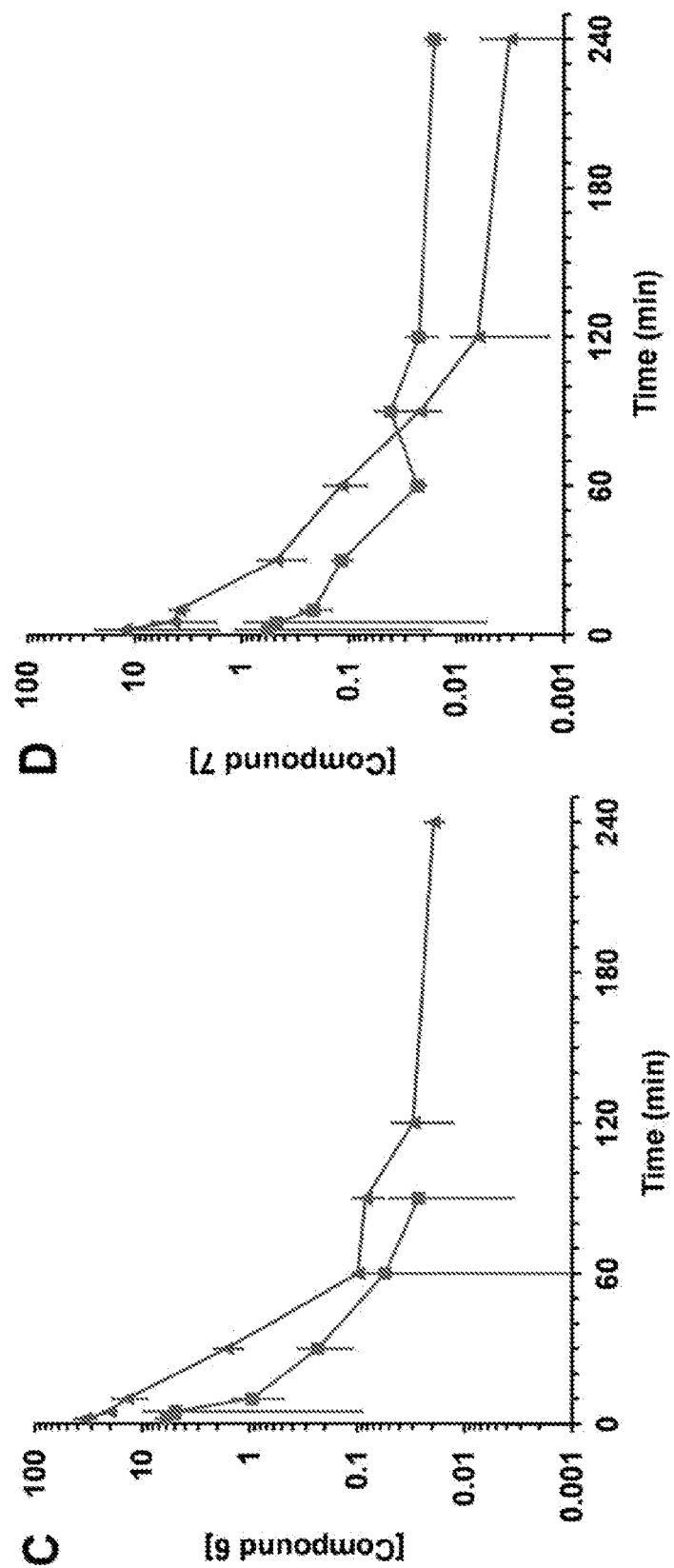

The pharmacokinetics (PK) and brain distribution were evaluated in mice after single iv dose administration at 5 mg/kg of compounds 4, 5, 6, and 7. Plasma and brain concentration-time curves and PK parameters are shown in FIG. 2 and Table 3, respectively. Plasma concentration of 4 was 62.4±61.6 µM at 2 min, the first time point collected, and decreased rapidly to 0.097±0.092 µM by 30 min, a level below the $K_i$ value for MMP-2. Compound 4 had a moderate clearance (CL) of 0.0158 L/min/kg (19% of hepatic blood flow), a low volume of distribution (Vd) of 0.0213 L/kg, a very short distribution half-life ($t_{1/2\alpha}$=0.621 min), and an elimination half-life ($t_{1/2\beta}$) of 74.5 min (Table 3). Levels of 4 in brain were in general lower than those in plasma. Brain levels of 4 were 9.76±7.24 pmol/mg tissue (equivalent to 9.76±7.24 µM assuming a density of 1.0 g/mL) at 2 min and decreased below the $K_i$ value for MMP-2 by 30 min. The brain to plasma $AUC_{0-\infty}$ ratio was 0.138 for compound 4, indicating that it crossed the BBB (FIG. 2A, Table 3).

TABLE 3

Pharmacokinetic Parameters after Single Intravenous Dose Administration

|  | Compound 4 | | Compound 5 | | Compound 6 | | Compound 7 | |
|---|---|---|---|---|---|---|---|---|
| Parameter | Brain | Plasma | Brain | Plasma | Brain | Plasma | Brain | Plasma |
| CL (L/min/Kg) | | 0.0158 | | 0.202 | | 0.0303 | | 0.107 |
| Vd (L/Kg) | | 0.0213 | | 2.76 | | 0.329 | | 1.08 |

TABLE 3-continued

Pharmacokinetic Parameters after Single Intravenous Dose Administration

| Parameter | Compound 4 | | Compound 5 | | Compound 6 | | Compound 7 | |
|---|---|---|---|---|---|---|---|---|
| | Brain | Plasma | Brain | Plasma | Brain | Plasma | Brain | Plasma |
| $AUC_{0-last}{}^{a}$ | 108 | 783 | 57.7 | 72.9 | 66.5 | 435 | 14.3 | 128 |
| $AUC_{0-\infty}{}^{a}$ | 108 | 784 | 58.3 | 73.6 | 67.2 | 437 | 17.4 | 128 |
| $t_{1/2\alpha}$(min) | 5.35 | 0.621 | 3.32 | 6.47 | 2.89 | 6.31 | 47 | 5.22 |
| $t_{1/2\beta}$(min) | 10.9 | 74.5 | 75.3 | 68.0 | 19.1 | 86.6 | 133 | 64.2 |
| $AUC_{brain}/AUC_{plasma}$ | 0.138 | | 0.793 | | 0.154 | | 0.136 | |

[a]AUC in pmol · min/mg for brain and in μM · min for plasma

The concentrations of compounds 4, 5, 6 and 7 after a 5 mg/kg single intravenous dose to mice are shown below in Table 4.

TABLE 4

Concentrations of Compounds 4, 5, 6 and 7 after 5 mg/kg Single I.V. Dose to Mice.

| Time (min) | Compound 4 | | Compound 5 | | Compound 6 | | Compound 7 | |
|---|---|---|---|---|---|---|---|---|
| | Brain[a] | Plasma[b] | Brain[a] | Plasma[b] | Brain[a] | Plasma[b] | Brain[a] | Plasma[b] |
| 2 | 9.76 ± 7.24 | 62.4 ± 61.6 | 5.55 ± 2.38 | 4.35 ± 1.10 | 5.98 ± 1.48 | 35.0 ± 7.7 | 0.577 ± 0.560 | 12.6 ± 10.9 |
| 5 | 5.98 ± 2.94 | 2.19 ± 0.09 | 2.97 ± 2.41 | 3.15 ± 1.49 | 4.90 ± 4.81 | 20.3 ± 2.8 | 0.476 ± 0.470 | 4.37 ± 2.63 |
| 10 | 3.27 ± 0.14 | 2.14 ± 1.51 | 1.20 ± 0.50 | 2.39 ± 0.82 | 0.954 ± 0.473 | 14.1 ± 5.0 | 0.216 ± 0.071 | 3.92 ± 0.78 |
| 30 | 0.249 ± 0.127 | 0.0970 ± 0.0920 | 0.213 ± 0.143 | 0.377 ± 0.116 | 0.231 ± 0.122 | 1.64 ± 0.48 | 0.117 ± 0.024 | 0.482 ± 0.229 |
| 60 | 0.0253 ± 0.0221 | 0.0863 ± 0.0303 | 0.0368 ± 0.0232 | 0.0574 ± 0.0316 | 0.0544 ± 0.0539 | 0.0979 ± 0.0065 | 0.0228 ± 0.0033 | 0.119 ± 0.051 |
| 90 | 0.00548 ± 0.00476 | 0.0716 ± 0.0500 | 0.0213 ± 0.0106 | 0.0332 ± 0.0065 | 0.0263 ± 0.0228 | 0.0827 ± 0.0262 | 0.0409 ± 0.0155 | 0.0220 ± 0.0080 |
| 120 | ND[c] | 0.0318 ± 0.0311 | 0.0158 ± 0.0125 | 0.0218 ± 0.0054 | ND[c] | 0.0297 ± 0.0168 | 0.0222 ± 0.0072 | 0.00630 ± 0.00490 |
| 240 | ND[c] | 0.0149 ± 0.0129 | 0.00531 ± 0.00402 | 0.00694 ± 0.00606 | ND[c] | 0.0193 ± 0.0037 | 0.0161 ± 0.0035 | 0.00320 ± 0.00266 |

[a]Concentrations in pmol/mg tissue;
[b]Concentrations in μM;
[c]Not Detectable.

Plasma and brain concentrations of compound 5 were above the $K_i$ values for MMP-2 and MMP-9 for at least 30 min (FIG. 2B and Table 5). As indicated earlier, the slow dissociation of compound 5 from MMP-9 should result in sustained inhibition even when levels of compound 5 in the brain are below the $K_i$ value. Compound 5 had a clearance of 0.202 L/min/kg, which is much higher than the hepatic blood flow rate of 0.086 L/min/kg, indicating high clearance of 5 from systemic circulation with a plasma $t_{1/2\beta}$ of 68.0 min. Compound 5 had a volume of distribution of 2.76 L/kg, indicating that 5 was highly distributed to tissues (Table 3). The brain to plasma $AUC_{0-\infty}$ ratio of 0.793 indicated that compound 5 crossed the BBB readily with a brain $t_{1/2\beta}$ of 75.3 min.

TABLE 5

Formation of N-Acetyl Metabolite (Compound 6) after a 5 mg/kg Single Intravenous Dose of Compound 5.

| | Compound 5 | | Compound 6 | |
|---|---|---|---|---|
| | Brain | Plasma | Brain | Plasma |
| $AUC_{0-last}{}^{a}$ | 57.7 | 72.9 | 0.265 | 0.926 |
| $AUC_{0-\infty}{}^{a}$ | 58.3 | 73.6 | ND[b] | 2.85 |
| $t_{1/2\alpha}$ (min) | 3.32 | 6.47 | 4.05 | 11.2 |
| $t_{1/2\beta}$ (min) | 75.3 | 68.0 | ND[b] | 990 |
| $AUC_{compound\ 6/5}$ | | | 0.0046 | 0.039 |

[a]AUC in pmol · min/mg for brain and in μM · min for plasma;
[b]Not determined

The plasma levels of compound 6 were 35.0±7.69 μM at 2 min and remained above $K_i$ for MMP-2 for 30 min. The distribution half-life was 6.31 min and the elimination half-life was 86.6 min (FIG. 2C, Table 3 and Table 5). The clearance of compound 6 was 0.0303 L/min/kg (35% of hepatic blood flow rate), indicating moderate clearance of 6 from systemic circulation (Davies et al., B.; Pharm. Res. 1993, 10, 1093-1095). The volume of distribution of compound 6 was 0.329 L/kg, indicating that 6 was moderately distributed to tissues (Table 3). Brain concentrations of compound 6 were 5.98±1.48 pmol/mg tissue at 2 min and were above the $K_i$ for MMP-2 (0.23 μM, Table 1) for 30 min. The brain to plasma $AUC_{0-\infty}$ ratio of 0.154 indicated that compound 6 crossed the BBB and achieved therapeutic concentrations in the brain (FIG. 2C, Table 3 and Table 5).

The AUC of the p-acetamidomethyl analog (compound 6), an aliphatic amide, relative to that of the p-aminomethyl (compound 5) was 0.5% in brain and 3.9% in plasma (Table 5). This indicated minimal in vivo N-acetylation of compound 5, an aliphatic amine. In contrast, N-acetylation of the aromatic amine in compound 2 was significant, as determined from the AUC of compound 2 relative to its corresponding N-acetyl metabolite (3) of 81% in brain and 7.4% in plasma. In addition, the active species after administration of 2 is compound 3. As the enzymes responsible for N-acetylation of compound 2 to compound 3 are polymorphic, direct administration of compound 3 was required to achieve therapeutic concentrations in the brain. On the other hand, p-aminomethyl (5) is active by itself and does not undergo significant N-acetylation.

The guanidino derivative 7 reached concentrations of 12.6±10.9 μM and 0.577±0.560 pmol/mg at 2 min in plasma and brain, respectively. Levels were above the $K_i$ for MMP-2 for 90 min in plasma and 120 min in brain, while concentrations were above the $K_i$ for MMP-9 for 60 min and 30 min in plasma and brain, respectively (FIG. 2D and Table 5). The clearance of compound 7 was high (0.107 L/min/kg) and the high volume of distribution of 1.08 L/kg indicated that compound 7 was highly distributed to tissues. The plasma $t_{1/2\beta}$ was 64.2 min. The brain to plasma $AUC_{0-\infty}$ ratio was 0.136, indicating that compound 7 crossed the BBB, with a brain $t_{1/2\beta}$ of 133 min (Table 3). The brain $t_{1/2\beta}$ of compound 7 was significantly longer than those of compounds 4, 5, and 6, suggesting prolonged duration of pharmacological effect.

Comparison of the PK properties of compounds 4-7 showed that clearance from plasma was the highest for compound 5, followed by 7, 6, and 4. Consistent with clearance, plasma systemic exposure (as measured by AUC) was the highest for compound 4, then 6, 7, and was the lowest for 5. The volume of distribution followed the same order as clearance: 5>7>6>4. While the volume of distribution describes the extent that a drug distributes to the body, it does not imply distribution to the brain. This is because the endothelial cells of the capillaries of organs allow passage of small molecules from blood into organs, however those of the brain capillaries are surrounded by tight junctions that prevent drugs in circulation from entering the brain. As a result, the volume of distribution does not correlate with the $AUC_{brain/blood}$, which was highest for compound 5>6>4=7. The high potency for MMP-9, the long residence time for inhibition of MMP-9, along with distribution of compound 5 to the brain and clearance from the brain, make compound 5 worthy of administration in animal models of MMP-9 dependent neurological diseases. Likewise, the potency and selectivity of compound 6 for MMP-2 and its ability to cross the BBB and achieve therapeutic concentrations in the brain make this compound a useful chemical tool for investigation of MMP-2 dependent animal models of neurological ailments.

Conclusions.

We designed and synthesized four analogs of compound 1 that were 10- to 14,000-fold more water soluble, retained activity towards MMP-2, and crossed the BBB. The p-aminomethyloxadiazol analog (4) is a selective MMP-2 inhibitor with a long residence time and moderate water solubility. The p-acetamidomethyl (compound 6) is a selective and 3-fold more potent slow-binding inhibitor of MMP-2 than 4; it does not inhibit MMP-9 or MMP-14. Because of its slow dissociation from the primary target MMP-2, the compound can provide sustained inhibition of MMP-2 even when concentrations of 6 are below the $K_i$ value. In contrast, compound 6 inhibits MMP-8 as a linear competitive inhibitor, with a short residence time. Compound 6 crosses the BBB and achieves therapeutic concentrations in the brain. This inhibitor is a useful probe to ascertain the role of MMP-2 in neurological diseases. The p-guanidino derivative (compound 7) has a water solubility of 32 mg/mL and inhibits MMP-2, MMP-9, and MMP-14 in a slow-binding manner and inhibits MMP-8 as a linear competitive inhibitor. The p-aminomethyl derivative (compound 5) is a water-soluble nanomolar inhibitor of MMP-2, MMP-9, and MMP-14; it crosses the BBB and achieves therapeutic concentrations in the brain. The residence time of 5 bound to MMP-9 is 6- to 7-fold longer than that of TIMP-1 or TIMP-2 bound to MMP-9. Thus, this inhibitor can be equally or more effective in regulating the activity of MMP-9.

Therapeutic Methods

A compound of Formula I or a pharmaceutically acceptable salt or solvate thereof (collectively, "active agents") are useful as MMP inhibitors, or for providing MMP inhibitors in vivo, or in vitro, in the methods of the invention. The active agents may be used for the treatment or prevention of medical conditions (such as a wound), diseases, or disorders mediated through inhibition or modulation of various MMPs, such as those described herein, including the conditions described in the Background section above. Active agents according to the invention may therefore be used as analgesics, anti-depressants, cognition enhancers, or neuroprotectants, as well as for treatments for the conditions described below.

Described herein are numerous diseases and conditions that might appear to be unrelated but each is related by shared mechanistic attributes. Each disease or condition described herein is gelatinase-dependent. For example, both auto-controlled growth and the ability to metastasize are associated with cancer. The compounds described herein can be anti-proliferative and anti-metastatic toward matrix metalloproteinase dependent diseases.

Compounds and pharmaceutical compositions suitable for use in the invention include those wherein the active agent is administered in an effective amount to achieve its intended purpose. The phrase "therapeutically effective amount" refers to an amount effective to treat the disease, disorder, and/or condition, for example, an amount effective to reduce the progression or severity of the condition or symptoms being treated. Determination of a therapeutically effective amount is well within the capacity of persons skilled in the art. The term "effective amount" can include an amount of a compound described herein, or an amount of a combination of compounds described herein, e.g., to treat or prevent a disease or disorder, or to treat the symptoms of the disease or disorder, in a host. Thus, an "effective amount" generally means an amount that provides the desired effect.

Exemplary medical conditions, diseases, and disorders include anxiety, depression, pain, sleep disorders, inflammation, multiple sclerosis and other movement disorders, HIV wasting syndrome, closed head injury, stroke, learning and memory disorders, Alzheimer's disease, epilepsy, Tourette's syndrome, epilepsy, Niemann-Pick disease, Parkinson's disease, Huntington's chorea, optic neuritis, autoimmune uveitis, symptoms of drug withdrawal, nausea, emesis, sexual dysfunction, post-traumatic stress disorder, or cerebral vasospasm, or combinations thereof, as well as the conditions described below.

The active agents may be used to treat subjects (patients) diagnosed with or suffering from a disease, disorder, or condition that is mediated through MMP activity, e.g., one of the 26 known gelatinases. The term "treat" or "treating" as used herein is intended to refer to administration of an agent or composition of the invention to a subject for the purpose of effecting a therapeutic or prophylactic benefit through modulation of MMP activity. Treating includes reversing, ameliorating, alleviating, inhibiting the progress of, lessening the severity of, or preventing a disease, disorder, or condition, or one or more symptoms of such disease, disorder or condition mediated through modulation of MMP activity.

The term "subject" refers to a mammalian patient in need of such treatment, such as a human. "Modulators" include both inhibitors and activators, where "inhibitors" refer to compounds that decrease, prevent, inactivate, desensitize or down-regulate MMP expression or activity, and "activators" are compounds that increase, activate, facilitate, sensitize, or up-regulate MMP expression or activity.

Accordingly, the invention relates to methods of using the active agents described herein to treat subjects diagnosed with or suffering from a disease, disorder, or condition mediated through MMP activity, such as anxiety, pain, sleep disorders, inflammation, or movement disorders (e.g., multiple sclerosis).

Symptoms or disease states are intended to be included within the scope of "medical conditions, disorders, or diseases." For example, pain may be associated with various diseases, disorders, or conditions, and may include various etiologies. Illustrative types of pain treatable with a MMP-modulating agent according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia.

Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

The invention also provides a composition comprising a compound of any one of the formulas described herein and a pharmaceutically acceptable diluent or carrier. The pharmaceutical composition can include a thrombolytic agent or an analgesic, such as an opioid or a non-steroidal anti-inflammatory drug. Examples of such analgesics include aspirin, acetaminophen, opioids, ibuprofen, naproxen, COX-2 inhibitors, gabapentin, pregabalin, tramadol, or combinations thereof.

The term "thrombolytic agent" refers to a drug that is able to dissolve a clot or "thrombus" and reopen an artery or vein. Thrombolytic agents may be used to treat a heart attack, stroke, deep vein thrombosis (e.g., a clot in a deep leg vein), pulmonary embolism, and occlusion of a peripheral artery or indwelling catheter. Thrombolytic agents are serine proteases and they convert plasminogen to plasmin, which breaks down fibrinogen and fibrin and dissolves blood clots. Currently available thrombolyic agents include reteplase (r-PA or Retavase), alteplase (t-PA or Activase), urokinase (Abbokinase), prourokinase, anisoylated purified streptokinase activator complex (APSAC), and streptokinase. Thrombolytic agents are also called clotbusters, clot-dissolving medications, and fibrinolyic agents.

Accordingly, the invention also provides a method of treating a subject suffering from or diagnosed with a disease, disorder, or medical condition mediated by MMP activity, comprising administering to the subject in need of such treatment an effective amount of at least one compound of a formula described herein, a pharmaceutically acceptable salt thereof, a pharmaceutically acceptable prodrug thereof, or a pharmaceutically active metabolite thereof. The disease, disorder, or medical condition can include anxiety, depression, pain, sleep disorders, eating disorders, inflammation, movement disorders, HIV wasting syndrome, closed head injury, stroke, Alzheimer's disease, epilepsy, Tourette's syndrome, Niemann-Pick disease, Parkinson's disease, Huntington's chorea, optic neuritis, autoimmune uveitis, drug withdrawal, nausea, emesis, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, hypertension, cancer, hepatitis, allergic airway disease, autoimmune diabetes, intractable pruritus, neuroinflammation, or a combination thereof.

The invention further includes a pharmaceutical composition for treating a disease, disorder, or medical condition mediated by MMP activity, comprising: (a) an effective amount of at least one compound of a formula described herein, or a pharmaceutically acceptable salt, a pharmaceutically acceptable prodrug, or a pharmaceutically active metabolite thereof, or any combination thereof, and a pharmaceutically acceptable excipient.

Diseases, Disorders, and Conditions

The compounds and compositions described herein can be used to treat or reduce the symptoms of the following diseases, disorders, and conditions.

The term "neurological disorder" refers to any disorder of the nervous system and/or visual system. "Neurological disorders" include disorders that involve the central nervous system (brain, brainstem and cerebellum), the peripheral nervous system (including cranial nerves), and the autonomic nervous system (parts of which are located in both central and peripheral nervous system). Neurodegenerative disorder also refers to a type of neurological disease marked by the loss of nerve cells, including, but not limited to, Alzheimer's disease, Parkinson's disease, amyotrophic lateral sclerosis, tauopathies (including fronto-temporal dementia), and Huntington's disease.

Major groups of neurological disorders include, but are not limited to, headache, stupor and coma, dementia, seizure, sleep disorders, trauma, infections, neoplasms, neuroophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological disorder. The following is a list of several neurological disorders, symptoms, signs and syndromes: Acquired Epileptiform Aphasia; Acute Disseminated Encephalomyelitis; Adrenoleukodystrophy; Agenesis of the corpus callosum; Agnosia; Aicardi syndrome; Alexander disease; Alpers' disease; Alternating hemiplegia; Alzheimer's disease; Amyotrophic lateral sclerosis; Anencephaly; Angelman syndrome; Angiomatosis; Anoxia; Aphasia; Apraxia; Arachnoid Cysts; Arachnoiditis; Arnold-Chiari malformation; Arteriovenous malformation; Asperger syndrome; Ataxia Telangiectasia; Attention Deficit Hyperactivity Disorder; Autism; Autonomic Dysfunction; Back Pain; Batten disease; Behcet's disease; Bell's palsy; Benign Essential Blepharospasm; Benign Focal; Amyotrophy; Benign Intracranial Hypertension; Binswanger's disease; Blepharospasm; Bloch Sulzberger syndrome; Brachial plexus injury; Brain abscess; Brain injury; Brain tumors (including Glioblastoma multiforme); Spinal tumor; Brown-Sequard syndrome; Canavan disease; Carpal tunnel syndrome (CTS); Causalgia; Central pain syndrome; Central pontine myelinolysis; Cephalic disorder; Cerebral aneurysm; Cerebral arteriosclerosis; Cerebral atrophy; Cerebral gigantism; Cerebral palsy; Charcot-Marie-Tooth disease; Chemotherapy-induced neuropathy and neuropathic pain; Chiari malformation; Chorea; Chronic inflammatory demyelinating polyneuropathy (CIDP); Chronic pain; Chronic regional pain syndrome; Coffin Lowry syndrome; Coma, including Persistent Vegetative State; Congenital facial diplegia; Corticobasal degeneration; Cranial arteritis; Craniosynostosis; Creutzfeldt-Jakob disease; Cumulative trauma disorders; Cushing's syndrome; Cytomegalic inclusion body disease (CIBD); Cytomegalovirus Infection; Dancing eyes-dancing feet syndrome; Dandy-Walker syndrome; Dawson disease; De Morsier's syndrome; Dejerine-Klumpke palsy; Dementia; Dermatomyositis; Diabetic neuropathy; Diffuse sclerosis; Dysautonomia; Dysgraphia; Dyslexia; Dystonias; Early infantile epileptic encephalopathy; Empty sella syndrome; Encephalitis; Encephaloceles; Encephalotrigeminal angiomatosis; Epilepsy; Erb's palsy; Essential tremor; Fabry's disease; Fahr's syndrome; Fainting; Familial spastic paralysis; Febrile seizures; Fisher syndrome; Friedreich's ataxia; Fronto-Temporal Dementia and other "Tauopathies"; Gaucher's disease; Gerstmann's syndrome; Giant cell arteritis; Giant cell inclusion disease; Globoid cell Leukodystrophy; Guillain-Barre syndrome; HTLV-1 associated myelopathy; Hallervorden-Spatz disease; Head injury; Headache; Hemifacial Spasm; Hereditary Spastic Paraplegia; Heredopathia atactica polyneuritiformis; Herpes zoster oticus; Herpes zoster; Hirayama syndrome; HIV-Associated Dementia and Neuropathy (see also Neurological manifestations of AIDS); Holoprosencephaly; Huntington's disease and other polyglutamine repeat diseases; Hydranencephaly; Hydrocephalus; Hypercortisolism; Hypoxia; Immune-Mediated encephalomyelitis; Inclusion body myositis; Incontinentia pigmenti; Infantile; phytanic acid storage disease; Infantile Refsum disease; Infantile spasms; Inflammatory myopathy; Intracranial cyst; Intracranial hypertension; Joubert syndrome; Kearns-Sayre syndrome; Kennedy disease; Kinsbourne syndrome; Klippel Feil syndrome; Krabbe disease; Kugelberg-Welander disease; Kuru; Lafora disease; Lambert-Eaton myasthenic syndrome; Landau-Kleffner syndrome; Lateral medullary (Wallenberg) syndrome; Learning disabilities; Leigh's disease; Lennox-Gastaut syndrome; Lesch-Nyhan syndrome; Leukodystrophy; Lewy body dementia; Lissencephaly; Locked-In syndrome; Lou Gehrig's disease (aka Motor Neuron Disease or Amyotrophic Lateral Sclerosis); Lumbar disc disease; Lyme disease-Neurological Sequelae; Machado-Joseph disease; Macrencephaly; Megalencephaly; Melkersson-Rosenthal syndrome; Menieres disease; Meningitis; Menkes disease; Metachromatic leukodystrophy; Microcephaly; Migraine; Miller Fisher syndrome; Mini-Strokes; Mitochondrial Myopathies; Mobius syndrome; Monomelic amyotrophy; Motor Neurone Disease; Moyamoya disease; Mucopolysaccharidoses; Multi-Infarct Dementia; Multifocal motor neuropathy; Multiple sclerosis and other demyelinating disorders; Multiple system atrophy with postural hypotension; Muscular dystrophy; Myasthenia gravis; Myeloclastic diffuse sclerosis; Myoclonic encephalopathy of infants; Myoclonus; Myopathy; Myotonia congenital; Narcolepsy; Neurofibromatosis; Neuroleptic malignant syndrome; Neurological manifestations of AIDS; Neurological sequelae of lupus; Neuromyotonia; Neuronal ceroid lipofuscinosis; Neuronal migration disorders; Niemann-Pick disease; O'Sullivan-McLeod syndrome; Occipital Neuralgia; Occult Spinal Dysraphism Sequence; Ohtahara syndrome; Olivopontocerebellar Atrophy; Opsoclonus Myoclonus; Optic neuritis; Orthostatic Hypotension; Overuse syndrome; Paresthesia; Parkinson's disease; Paramyotonia Congenita; Paraneoplastic diseases; Paroxysmal attacks; Parry Romberg syndrome; Pelizaeus-Merzbacher disease; Periodic Paralyses; Peripheral Neuropathy; Painful Neuropathy and Neuropathic Pain; Persistent Vegetative State; Pervasive developmental disorders; Photic sneeze reflex; Phytanic Acid Storage disease; Pick's disease; Pinched Nerve; Pituitary Tumors; Polymyositis; Porencephaly; Post-Polio syndrome; Postherpetic Neuralgia (PHN); Postinfectious Encephalomyelitis; Postural Hypotension; Prader-Willi syndrome; Primary Lateral Sclerosis; Prion diseases; Progressive; Hemifacial Atrophy; Progressive multifocal leukoencephalopathy; Progressive Sclerosing Poliodystrophy; Progressive Supranuclear Palsy; Pseudotumor cerebri; Ramsay-Hunt syndrome (Type I and Type II); Rasmussen's Encephalitis; Reflex Sympathetic Dystrophy syndrome; Refsum disease; Repetitive Motion Disorders; Repetitive Stress Injuries; Restless Legs syndrome; Retrovirus-Associated Myelopathy; Rett syndrome; Reye's syndrome; Saint Vitus Dance; Sandhoff disease; Schilder's disease; Schizencephaly; Septo-Optic Dysplasia; Shaken Baby syndrome; Shingles; Shy-Drager syndrome; Sjogren's syndrome; Sleep Apnea; Soto's syndrome; Spasticity; Spina bifida; Spinal cord injury; Spinal cord tumors; Spinal Muscular Atrophy; Stiff-Person syndrome; Stroke; Sturge-Weber syndrome; Subacute Sclerosing Panencephalitis; Subarachnoid Hemorrhage; Subcortical Arteriosclerotic Encephalopathy; Sydenham Chorea; Syncope; Syringomyelia; Tardive dyskinesia; Tay-Sachs disease; Temporal arteritis; Tethered Spinal Cord syndrome; Thomsen disease; Thoracic Outlet syndrome; Tic Douloureux; Todd's Paralysis; Tourette syndrome; Transient ischemic attack; Transmissible Spongiform Encephalopathies; Transverse myelitis; Traumatic Brain injury; Tremor; Trigeminal Neuralgia; Tropical Spastic Paraparesis; Tuberous Sclerosis; Vascular Dementia (Multi-Infarct Dementia); Vasculitis including Temporal Arteritis; Von Hippel-Lindau Disease (VHL); Wallenberg's syndrome; Werdnig-Hoffman disease; West syndrome; Whiplash; Williams syndrome; Wilson's disease; and Zellweger syndrome.

The medical therapy can also be for the treatment of cancer, angiogenesis, cardiovascular disease, neurological disease, inflammation, eye disease, autoimmune disease, or other conditions that are affected by the regulation of MMPs. The cancer can be pancreatic cancer, gastric cancer, lung cancer, colorectal cancer, prostate cancer, renal cell cancer, basal cell cancer, breast cancer, bone cancer, brain cancer, lymphoma, leukemia, melanoma, myeloma and other hematological cancers, and the like. The cancer can be primary, metastatic, or both. The treatment of cancer using a compound of the invention can affect (i.e., inhibit or promote) angiogenesis. The cardiovascular disease can be stroke, aneurysm, ischemia or reperfusion injury.

A compound of a formula described herein, or a pharmaceutically acceptable salt thereof, can be administered to a mammal (e.g., human) alone or in conjunction with a second agent, such as a neurological agent, or a pharmaceutically acceptable salt thereof. Accordingly, the compound can be administered in conjunction with a thrombolytic agent, such as tPA to treat a disorder, disease, or condition as described herein.

The term "neurological agent" refers to a compound, including chemical and biological compounds (e.g., peptides, oligonucleotides and antibodies), that has an effect on the nervous system, e.g., compounds capable of treating, inhibiting or preventing disorders affecting the nervous system or compounds capable of eliciting a neurological and/or an ophthalmological disorder or symptoms thereof.

Various studies indicate that MMP-9 and MMP-2 contribute in the disease process of stroke. Gelatinase inhibitors can protect the neurovascular integrity of the brain from ischemia or exogenous tPA thrombolysis by blocking degradation of the basal membrane laminin and exerting anti-apoptotic effects on neurons. The selectivity of the compounds described herein therefore allow for the treatment of both ischemic and hemorrhagic stroke. Additionally, combined treatment with selective gelatinase inhibitors and tPA can minimize neurotoxicity and hemorrhagic transformation associated with tPA use, thereby extending the window of treatment for reperfusion therapy of tPA.

For this approach to effectively treat stroke patients, it may require delivery of the gelatinase inhibitors by intravenous administration. Water-soluble prodrugs of second-generation gelatinase inhibitors have been prepared as described herein, and are amenable to intravenous administration. This novel therapeutic strategy by itself or in combination with tPA can reduce injury and extend the time window for thrombolytic therapy in patients with stroke.

The neurological disease can be one that arises from at least one of painful neuropathy, neuropathic pain, diabetic neuropathy, drug dependence, drug withdrawal, depression, anxiety, movement disorders, tardive dyskinesia, cerebral infections that disrupt the blood-brain barrier, meningitis, stroke, hypoglycemia, cardiac arrest, spinal cord trauma, head trauma, and perinatal hypoxia. The neurological disease can also be a neurodegenerative disorder. The neurological disease can be epilepsy, Alzheimer's disease, Huntington's disease, Parkinson's disease, multiple sclerosis, or amyotrophic lateral sclerosis, as well as Alexander disease, Alper's disease, Ataxia telangiectasia, Batten disease (also known as Spielmeyer-Vogt-Sjogren-Batten disease), Canavan disease, Cockayne syndrome, Corticobasal degeneration, Creutzfeldt-Jakob disease, Kennedy's disease, Krabbe disease, lewy body dementia, Machado-Joseph disease (Spinocerebellar ataxia type 3), Multiple System Atrophy, Pelizaeus-Merzbacher disease, Pick's disease, primary lateral sclerosis, Refsum's disease, Sandhoff disease, Schilder's disease, spinocerebellar ataxia (multiple types with varying characteristics), spinal muscular atrophy, Steele-Richardson-Olszewski disease, or tabes dorsalis.

The compounds described herein can be used to treat conditions of the eye, including corneal wounds, glaucoma, dry eye disease, and macular degeneration. The compounds can also be used to treat eye conditions that involve, are caused by, are effected by, or are exacerbated by MMP-9.

The compounds described herein can be used to treat inflammation, wherein the inflammation involves connective tissue, airway tissue, or central nervous system tissue. The inflammation can be acute asthma, chronic asthma, allergic asthma, or chronic obstructive pulmonary disease. In one embodiment, the inflammation is arthritis.

The compounds described herein can be used to treat an ophthalmologic disease. The term "ophthalmologic disease" or "ophthalmologic disorder" refers to a disease or disorder involving the anatomy and/or function of the visual system, including but not limited to, glaucoma, retinal artery occlusion, ischemic optic neuropathy and wet or dry macular degeneration.

A neurological disorder can be an affective disorder (e.g., depression or anxiety). The term "affective disorder" or "mood disorder" refers to a variety of conditions characterized by a disturbance in mood as the main feature.

The term "depression" refers to an abnormal mood disturbance characterized by feelings of sadness, despair, and discouragement. Depression refers to an abnormal emotional state characterized by exaggerated feelings of sadness, melancholy, dejection, worthlessness, emptiness, and hopelessness that are inappropriate and out of proportion to reality. See, *Mosby's Medical, Nursing & Allied Health Dictionary*, 5th Edition (1998). Depression can be at least one of a major depressive disorder (single episode, recurrent, mild, moderate, severe without psychotic features, severe with psychotic features, chronic, with catatonic features, with melancholic features, with atypical features, with postpartum onset, in partial remission, in full remission), dysthymic disorder, adjustment disorder with depressed mood, adjustment disorder with mixed anxiety and depressed mood, premenstrual dysphoric disorder, minor depressive disorder, recurrent brief depressive disorder, post-psychotic depressive disorder of schizophrenia, a major depressive disorder associated with Parkinson's disease, and a major depressive disorder associated with dementia.

The term "anxiety disorders" refers to an excessive or inappropriate aroused state characterized by feelings of apprehension, uncertainty, or fear. Anxiety disorders have been classified according to the severity and duration of their symptoms and specific behavioral characteristics. Categories include: Generalized anxiety disorder (GAD), which is long-lasting and low-grade; Panic disorder, which has more dramatic symptoms; Phobias; Obsessive-compulsive disorder (OCD); Post-traumatic stress disorder (PTSD); and Separation anxiety disorder.

The neurological disorder can be pain associated depression (PAD). The term "pain associated depression" refers to a depressive disorder characterized by the co-morbidity of pain and atypical depression. Specifically, the pain can be chronic pain, neuropathic pain, or a combination thereof. Specifically, the pain associated depression can include atypical depression and chronic pain wherein the chronic pain precedes the atypical depression. Alternatively, the pain associated depression can include atypical depression and chronic pain wherein the atypical depression precedes the chronic pain. The pain associated depression can include atypical depression and neuropathic pain.

"Chronic pain" refers to pain that continues or recurs over a prolonged period of time (i.e., >3 mos.), caused by various diseases or abnormal conditions, such as rheumatoid arthritis. Chronic pain may be less intense than acute pain. The person with chronic pain does not usually display increased pulse and rapid perspiration because the automatic reactions to pain cannot be sustained for long periods of time. Others with chronic pain may withdraw from the environment and concentrate solely on their affliction, totally ignoring their family, their friends, and external stimuli. See, *Mosby's Medical, Nursing & Allied Health Dictionary*, 5th Edition (1998).

"Atypical depression" refers to a depressed affect, with the ability to feel better temporarily in response to positive life effect (mood reactivity), plus two or more neurovegetative symptoms selected from the group of hypersomnia, increased appetite or weight gain, leaden paralysis, and a long standing pattern of extreme sensitivity to perceived interpersonal rejection; wherein the neurovegetative symptoms are present for more than about two weeks. It is appreciated that those of skill in the art recognize that the neurovegatative symptoms can be reversed compared to those found in other depressive disorders (e.g., melancholic depression); hence the term "atypical."

The term "acute neurological disorder" refers to a neurological disorder, as defined above, wherein the disorder has a rapid onset which is followed by a short but severe course, including, but not limited to, Febrile Seizures, Guillain-Barré syndrome, stroke, and intracerebral hemorrhaging (ICH).

The term "chronic neurological disorder" refers to a neurological disorder, as defined above, wherein the disorder lasts for a long period of time (e.g., more than about 2 weeks; specifically, the chronic neurological disorder can continue or recur for more than about 4 weeks, more than about 8 weeks, or more than about 12 weeks) or is marked by frequent recurrence, including, but not limited to, narcolepsy, chronic inflammatory demyelinating polyneuropathy, Cerebral palsy (CP), epilepsy, multiple sclerosis, dyslexia, Alzheimer's disease and Parkinson's Disease.

The term "trauma" refers to any injury or shock to the body, as from violence or an accident. The term trauma also refers to any emotional wound or shock, many of which may create substantial, lasting damage to the psychological development of a person, often leading to neurosis.

The term "ischemic conditions" refers to any condition which results in a decrease in the blood supply to a bodily organ, tissue, or part caused by constriction or obstruction of the blood vessels, often resulting in a reduction of oxygen to the organ, tissue, or part. The term "hypoxic conditions" refers to conditions in which the amount/concentration of oxygen in the air, blood or tissue is low (subnormal).

The term "painful neuropathy" or "neuropathy" refers to chronic pain that results from damage to or pathological changes of the peripheral or central nervous system. Peripheral neuropathic pain is also referred to as painful neuropathy, nerve pain, sensory peripheral neuropathy, or peripheral neuritis. With neuropathy, the pain is not a symptom of injury, but rather the pain is itself the disease process. Neuropathy is not associated with the healing process. Rather than communicating that there is an injury somewhere, the nerves themselves malfunction and become the cause of pain.

"Neuropathic pain" refers to pain associated with inflammation or degeneration of the peripheral nerves, cranial nerves, spinal nerves, or a combination thereof. The pain is typically sharp, stinging, or stabbing. The underlying disorder can result in the destruction of peripheral nerve tissue and can be accompanied by changes in the skin color, temperature, and edema. See, *Mosby's Medical, Nursing & Allied Health Dictionary*, 5th Edition (1998); and *Stedman's Medical Dictionary*, 25th Edition (1990).

The term "diabetic neuropathy" refers to a peripheral nerve disorder/nerve damage caused by diabetes, including peripheral, autonomic, and cranial nerve disorders/damage associated with diabetes. Diabetic neuropathy refers to a common complication of diabetes mellitus in which nerves are damaged as a result of hyperglycemia (high blood sugar levels).

The term "tardive dyskinesia" refers to a serious, irreversible neurological disorder that can appear at any age. Tardive Dyskinesia, e.g., Tourette's syndrome, can be a side effect of long-term use of antipsychotic/neuroleptic drugs. Symptoms involve uncontrollable movement of various body parts, including the body trunk, legs, arms, fingers, mouth, lips, or tongue.

The term "movement disorder" refers to a group of neurological disorders that involve the motor and movement systems, including, but are not limited to, Ataxia, Parkinson's disease, Blepharospasm, Angelman Syndrome, Ataxia Telangiectasia, Dysphonia, Dystonic disorders, Gait disorders, Torticollis, Writer's Cramp, Progressive Supranuclear Palsy, Huntington's Chorea, Wilson's Disease, Myoclonus, Spasticity, Tardive dyskinesia, Tics and Tourette syndrome and Tremors.

The term "cerebral infections that disrupt the blood-brain barrier" refers to infections of the brain or cerebrum that result in an alteration in the effectiveness of the blood-brain barrier, either increasing or decreasing its ability to prevent, for example, substances and/or organisms from passing out of the bloodstream and into the CNS.

The term "the blood-brain barrier" refers to a semipermeable cell layer of endothelial cells (interior walls) within capillaries of the central nervous system (CNS). The blood-brain barrier prevents large molecules, immune cells, many potentially damaging substances, and foreign organisms (e.g., viruses), from passing out of the bloodstream and into the CNS (Brain and Spinal Cord). A dysfunction in the Blood-Brain Barrier may underlie in part the disease process in MS (multiple sclerosis).

The term "meningitis" refers to inflammation of the meninges of the brain and the spinal cord, most often caused by a bacterial or viral infection and characterized by fever, vomiting, intense headache, and stiff neck. The term "meningoencephalitis" refers to inflammation of both the brain and meninges.

The term "stroke" refers to a sudden loss of brain function caused by a blockage or rupture of a blood vessel to the brain (resulting in the lack of oxygen to the brain), characterized by loss of muscular control, diminution or loss of sensation or consciousness, dizziness, slurred speech, or other symptoms that vary with the extent and severity of the damage to the brain, also called cerebral accident, or cerebrovascular accident. The term "cerebral ischemia" (or "stroke") also refers to a deficiency in blood supply to the brain, often resulting in a lack of oxygen to the brain.

The term "cardiac arrest" refers to a sudden cessation of heartbeat and cardiac function, resulting in a temporary or permanent loss of effective circulation.

The term "spinal cord trauma" refers to damage to the spinal cord that results from direct injury to the spinal cord itself or indirectly by damage to the bones and soft tissues and vessels surrounding the spinal cord. It is also called Spinal cord compression; Spinal cord injury; or Compression of spinal cord.

The term "head trauma" refers to a head injury of the scalp, skull, or brain. These injuries can range from a minor bump on the skull to a devastating brain injury. Head trauma can be classified as either closed or penetrating. In a closed head injury, the head sustains a blunt force by striking against an object. A concussion is a type of closed head injury that involves the brain. In a penetrating head injury, an object breaks through the skull and enters the brain.

The term "perinatal hypoxia" refers to a lack of oxygen during the perinatal period (defined as the period of time occurring shortly before and after birth, variously defined as beginning with completion of the twentieth to twenty eighth week of gestation and ending 7 to 28 days after birth).

The term "hypoglycemic neuronal damage" refers to neuronal damage, for example, nerve damage, as a result of a hypoglycemic condition (an abnormally low level of glucose in the blood).

The term "epilepsy" refers to any of various neurological disorders characterized by sudden recurring attacks of motor, sensory, or psychic malfunction with or without loss of consciousness or convulsive seizures.

The term "Alzheimer's disease" refers to a disease marked by the loss of cognitive ability, generally over a period of 10 to 15 years, and associated with the development of abnormal tissues and protein deposits in the cerebral cortex (known as plaques and tangles).

The term "Huntington's disease" refers to a disease that is hereditary in nature and develops in adulthood and ends in dementia. More specifically, Huntington's disease (HD) results from genetically programmed degeneration of brain cells, called neurons, in certain areas of the brain caused by a polyglutamine repeat in the DNA sequence of the gene encoding the protein huntingtin. This degeneration causes uncontrolled movements, loss of intellectual faculties, and emotional disturbance.

The term "Parkinsonism" refers to a disorder similar to Parkinson's disease, but which is caused by the effects of a medication, a different neurodegenerative disorder or another illness. The term "parkinsonism" also refers to any condition that causes any combination of the types of movement abnormalities seen in Parkinson's disease by damaging or destroying dopamine neurons in a certain area of the brain.

The term "amyotrophic lateral sclerosis" (ALS), also called Lou Gehrig's disease and Motor Neuron Disease, refers to a progressive, fatal neurological disease. The disorder belongs to a class of disorders known as motor neuron diseases. ALS occurs when specific nerve cells in the brain and spinal cord that control voluntary movement gradually degenerate (usually the "upper" (in the cerebrocortex) and "lower" (in the spinal cord) motor neurons, although some variants known as primary lateral sclerosis, apparently representing a separate disease, affect only the upper motor neurons). The loss of these motor neurons causes the muscles under their control to weaken and waste away, leading to paralysis. ALS manifests itself in different ways, depending on which muscles weaken first. Symptoms may include tripping and falling, loss of motor control in hands and arms, difficulty speaking, swallowing and/or breathing, persistent fatigue, and twitching and cramping, sometimes quite severely. Upper motor neuron variants (e.g., primary lateral sclerosis) are also included.

The term "glaucoma" refers to any of a group of eye diseases characterized by abnormally high intraocular fluid pressure, damaged optic disk, hardening of the eyeball, and partial to complete loss of vision. The retinal ganglion cells are lost in glaucoma. Some variants of glaucoma have normal intraocular pressure (known also as low tension glaucoma).

The term "retinal ischemia" refers to a decrease in the blood supply to the retina.

The term "ischemic optic neuropathy" refers to a condition that usually presents with sudden onset of unilaterally reduced vision. The condition is the result of decreased blood flow to the optic nerve (ischemia). There are two basic types: arteritic and non-arteritic ischemic optic neuropathy. Non-arteritic ischemic optic neuropathy is generally the result of cardiovascular disease. Those patients at greatest risk have a history of high blood pressure, elevated cholesterol, smoking, diabetes, or combinations of these. Arteritic ischemic optic neuropathy is a condition caused by the inflammation of vessels supplying blood to the optic nerve, known as temporal arteritis. This condition usually presents with sudden and severe vision loss in one eye, pain in the jaw with chewing, tenderness in the temple area, loss of appetite, and a generalized feeling of fatigue or illness.

The term "macular degeneration" refers to the physical disturbance of the center of the retina called the macula. The macula is the part of the retina which is capable of our most acute and detailed vision. Macular degeneration is the leading cause of legal blindness in people over age 55 (legal blindness means that a person can see 20/200 or less with eyeglasses.) Even with a loss of central vision, however, color vision and peripheral vision may remain clear. Vision loss usually occurs gradually and typically affects both eyes at different rates.

As used herein a "demyelinating disorder" refers to a medical condition where the myelin sheath is damaged. The myelin sheath surrounds nerves and is responsible for the transmission of impulses to the brain. Damage to the myelin sheath may result in muscle weakness, poor coordination and possible paralysis. Examples of demyelinating disorders include Multiple Sclerosis (MS), optic neuritis, transverse neuritis and Guillain-Bane Syndrome (GBS). In one embodiment, when treating a demyelinating disorder, an MMP inhibitor is administered with an NMDAR antagonist (e.g., memantine) or with β-interferon isoforms, copaxone or Antegren (natalizumab). Recently, it has been noted that underlying neuronal damage can occur in demyelinating conditions such as MS, and therefore useful drugs may also protect the neurons instead or in addition to the myelin.

The term "multiple sclerosis" refers to a chronic disease of the central nervous system, which predominantly affects young adults. Viral and autoimmune etiologies are postulated. Genetic and environmental factors are known to contribute to MS, but a specific cause for this disease is not yet identified. Pathologically, MS is characterized by the presence of areas of demyelination and T-cell predominant perivascular inflammation in the brain white matter. Some axons may be spared from these pathological processes. The disease begins most commonly with acute or subacute onset of neurologic abnormalities. Initial and subsequent symptoms may dramatically vary in their expression and severity over the course of the disease that usually lasts for many years. Early symptoms may include numbness and/or paresthesia, mono- or paraparesis, double vision, optic neuritis, ataxia, and bladder control problems. Subsequent symptoms also include more prominent upper motor neuron signs, i.e., increased spasticity, increasing para- or quadriparesis. Vertigo, incoordination and other cerebellar problems, depression, emotional lability, abnormalities in gait, dysarthria, fatigue and pain are also commonly seen.

The term "sequelae of hyperhomocystinemia" refers to a condition following as a consequence hyperhomocystinemia, meaning elevated levels of homocysteine.

The term "brain edema" refers to an excessive accumulation of fluid in, on, around and/or in relation to the brain.

The term "AIDS induced dementia" or "HIV-associated dementia" refers to dementia (deterioration of intellectual faculties, such as memory, concentration, and judgment, resulting from an organic disease or a disorder of the brain) induced by AIDS (Acquired Immunodeficiency Syndrome—an epidemic disease caused by an infection by human immunodeficiency virus (HIV-1, HIV-2), a retrovirus that causes immune system failure and debilitation and is often accompanied by infections such as tuberculosis).

The term "HIV-related neuropathy" refers to a neuropathy in a mammal infected with HIV were the neuropathy is caused by infections such as CMV or other viruses of the herpes family. Neuropathy is the name given to a group of disorders whose symptoms may range from a tingling sensation or numbness in the toes and fingers to paralysis. Neuropathy might more accurately be called "neuropathies" because there are several types and can be painful.

The term "retinopathy" refers to any pathological disorder of the retina.

The term "cognitive disorder" refers to any cognitive dysfunction, for example, disturbance of memory (e.g., amnesia) or learning.

The term "neuronal injury associated with HIV infection" refers to damage/injury of nerve cells caused either directly or indirectly by infection with HIV.

The term "dysfunction in cognition, movement and sensation" refers to abnormal or impaired functioning in cognition (mental process of knowing, including aspects such as awareness, perception, reasoning, and judgment), movement or sensation.

Any of the above diseases, disorders, or conditions can be treated by administering a compound or composition that includes a compound described herein to treat the disease, disorder, or condition by selectively inhibiting matrix a metalloproteinase.

Wound Therapy

Selective matrix metalloproteinase (MMP) inhibitors have been found to facilitate healing of wounds, including diabetic wounds and chronic wounds. It has been discovered that a number of selective inhibitor compounds significantly accelerate the healing process of various chronic wounds. The evaluations described herein demonstrate that these compounds are indeed efficacious in accelerating the healing process in diabetic mammals. Notably, the therapy was effective in diabetic mice but not in non-diabetic mice. The non-diabetic mice treated with an MMP inhibitor failed to show any acceleration effect for their wound healing. These compounds are the first discovered for this type of therapy. There are no current clinical agents that can accelerate the wound healing process in diabetics, therefore the compounds, compositions, and methods described herein will be of significant importance to patients and practitioners in need of therapeutic methods for treating chronic wounds.

The invention thus provides methods of accelerating the healing process of a skin wound. The methods can include administering to a mammal afflicted with a skin wound an effective amount of an MMP inhibitor, or a pharmaceutically acceptable salt thereof, wherein the gelatinase inhibitor accelerates the healing process of the skin wound.

The invention also provides methods of inhibiting the progression of a skin wound associated disease state characterized by elevated levels of matrix metalloproteinases. The methods can include administering to a mammal afflicted with a skin wound an effective amount of a gelatinase inhibitor, or a pharmaceutically acceptable salt thereof, effective to inhibit the progression of the skin wound in the mammal.

The invention further provides a method for enhancing the rate of repair of a diabetic skin wound. The method can include administering to the skin wound an effective amount of a gelatinase inhibitor, or a pharmaceutically acceptable salt thereof, wherein the rate of repair of the skin wound is enhanced, for example, compared to the rate of repair of a skin wound not receiving administration of the gelatinase inhibitor.

The invention additionally provides a dressing or patch for a chronic skin wound. The dressing or patch can include an effective amount of a gelatinase inhibitor, or a pharmaceutically acceptable salt thereof, and a pharmaceutically acceptable carrier, diluent, or excipient. For example, the active can be included in an ointment base, where the gelatinase inhibitor and the ointment base are combined and incorporated into a dressing. The dressing can a woven or non-woven fabric and can further include a backing and/or an adhesive.

In some embodiments, the effective amount of an MMP inhibitor described herein can be, for example, about 0.01 to about 50 mg per day, about 0.1 to about 10 mg per day, about 0.5 to about 5 mg per day, or about 0.5 to about 2.5 mg per day. The effective amount of the gelatinase inhibitor can be applied, for example, topically, optionally in combination with other actives and/or carriers. The amount per day can be an amount in a composition applied, for example, topically or transdermally, or it can be an amount administered by another means, such as subdermally. For topical administration, the amount can also be about 0.01 to about 50 mg per day, about 0.1 to about 10 mg per day, about 0.5 to about 5 mg per day, or about 0.5 to about 2.5 mg per 100 $cm^2$ of wound on the surface of the patient being treated.

In some embodiments, the skin wound is a chronic skin wound. Subjects having wounds treatable by the methods described herein include mammals, such as humans. In some cases, the mammal can be suffering from diabetes, and the skin wound can be a chronic diabetic skin wound. The inhibitor can be delivered to the skin wound in a variety of forms, such as in an ointment, or the administration of the inhibitor can be intraperitoneal, such as intravenous administration.

The invention therefore provides therapeutic methods of treating skin wounds in a mammal. The methods can include administering to a mammal having a wound, such as a chronic skin wound, an effective amount of a compound or composition described herein. The invention also provides compounds useful for treating wounds of the integument (e.g., skin ulcers and any break or damage to the integument) or wounds as a result of surgery, which can include systemic treatment to aid the healing of such internal wounds.

Marked upregulation of MMP-2 and MMP-9 is found in chronic wounds. Higher levels of MMP-9 in chronic wound fluid correlate with clinically more severe wounds. Reduced levels of TIMP are also found in chronic wounds. As described herein, it has now been determined that selective gelatinase inhibitors can be effective in the treatment of chronic wounds.

The compositions and methods described herein can be used for aiding wound management. The term "wound management" refers to therapeutic methods that induce and/or promote repair of a wound including, but not limited to, arresting tissue damage such as necrotization, promoting tissue growth and repair, reduction or elimination of an established microbial infection of the wound and prevention of new or additional microbial infection or colonization. The term can further include reducing or eliminating the sensation of pain attributable to a wound.

The therapeutic compositions for use in methods of wound management can include a surfactant that can useful in cleaning a wound or contributing to bactericidal activity of the administered compositions. Suitable surfactants include, but are not limited to, phospholipids such as lecithin, including soy lecithin and detergents. The surfactant selected for application to a wound or skin surface will typically be mild and will not lead to extensive irritation or promote further tissue damage to the patient.

A "wound" refers to an injury to the body, including but not limited to an injury from trauma, violence, accident, or surgery. A wound may occur due to laceration or breaking of a membrane (such as the skin) and usually damage to underlying tissues. A wound may occur in a topical location or internally. Chronic wounds may be caused by diseases, including but not limited to diabetes; diseases of internal organs, including but not limited to diseases of the liver, kidneys or lungs; cancer; or any other condition that slows the healing process.

Natural healing occurs in clearly defined stages. Skin wounds of acute nature may heal in 1-3 weeks in a biological process that restores the integrity and function of the skin and the underlying tissue. Such wounds may be the result of a scrape, abrasion, cut, graze, incision, tear, or bruise to the skin. If a wound does not heal in 4-12 weeks, it may be considered chronic. In the chase of chronic wounds, the wound may be attenuated at one of the stages of healing or fail to progress through the normal stages of healing. A chronic wound may have been present for a brief period of time, such as a month, or it may have been present for several years.

The phrase "chronic skin wound" includes, but is not limited to, skin ulcers, bed sores, pressure sores, diabetic ulcers and sores, and other skin disorders. Chronic skin wounds can be any size, shape or depth, and may appear discolored as compared to normal, healthy skin pigment. Chronic skin wounds can bleed, swell, seep pus or purulent discharge or other fluid, cause pain or cause movement of the affected area to be difficult or painful. Chronic skin wounds can become infected, producing elevated body temperatures, as well as pus or discharge that is milky, yellow, green, or brown in color, and is odorless or has a pungent odor. If infected, chronic skin wounds may be red, tender, or warm to the touch.

Chronic skin wounds can be caused by diabetes, poor blood supply, low blood oxygen, by conditions where blood flow is decreased due to low blood pressure, or by conditions characterized by occluded, blocked or narrowed blood vessels. A low oxygen supply can be caused by certain blood, heart, and lung diseases, and/or by smoking cigarettes. Chronic skin wounds can also be the result of repeated trauma to the skin, such as swelling or increased pressure in the tissues, or constant pressure on the wound area. Chronic skin wounds can be caused by a weakened or compromised immune system. A weakened or compromised immune system can be caused by increasing age, radiation, poor nutrition, and/or medications, such as anti-cancer medicines or steroids. Chronic skin wounds can also be cause by bacterial, viral or fungal infections, or the presence of foreign objects.

The term "diabetes" refers to any of several metabolic conditions characterized by the excessive excretion of urine and persistent thirst. The excess of urine can be caused by a deficiency of antidiuretic hormone, as in diabetes insipidus, or it can be the polyuria resulting from the hyperglycemia that occurs in diabetes mellitus.

The phrase "type 1 diabetes mellitus" refers to the first of the two major types of diabetes mellitus, characterized by abrupt onset of symptoms (often in early adolescence), insulinopenia, and dependence on exogenous insulin. It results from a lack of insulin production by the pancreatic beta cells. With inadequate control, hyperglycemia, protein wasting, and ketone body production occur. The hyperglycemia leads to overflow glycosuria, osmotic diuresis, hyperosmolarity, dehydration, and diabetic ketoacidosis, which can progress to nausea and vomiting, stupor, and potentially fatal hyperosmolar coma. The associated angiopathy of blood vessels (particularly microangiopathy) affects the retinas, kidneys, and arteriolar basement membranes. Polyuria, polydipsia, polyphagia, weight loss, paresthesias, blurred vision, and irritability can also occur.

The phrase "type 2 diabetes mellitus" refers to the second of the two major types of diabetes mellitus, peaking in onset between 50 and 60 years of age, characterized by gradual onset with few symptoms of metabolic disturbance (glycosuria and its consequences) and control by diet, with or without oral hypoglycemics but without exogenous insulin required. Basal insulin secretion is maintained at normal or reduced levels, but insulin release in response to a glucose load is delayed or reduced. Defective glucose receptors on the pancreatic beta cells may be involved. It is often accompanied by disease of blood vessels, particularly the large ones, leading to premature atherosclerosis with myocardial infarction or stroke syndrome.

Patients suffering from diabetes can develop chronic wounds of the skin, internal wounds from surgery, or other medical conditions that are not able to fully heal without the aid of the treatments methods described herein.

Combination Therapy

In the following description, component "(b)" is to be understood to represent one or more agents as described herein (e.g., a compound of Formula I). Thus, if components (a) and (b) are to be treated the same or independently, each agent of component (b) may also be treated the same or independently. Components (a) and (b) may be formulated together, in a single dosage unit (that is, combined together, e.g., in one lotion, cream, gel, ointment, or formulation for injection) as a combination product. When component (a) and (b) are not formulated together in a single dosage unit, the component (a) may be administered at the same time as component (b), or in any order. For example component (a) may be administered first, followed by administration of component (b), or they may be administered in the reverse order. If component (b) contains more than one agent, e.g., a thrombolytic agent and NSAID, these agents may be administered together or separately in any order. When not administered at the same time, the administration of component (a) and (b) can occur less than about one day, or less than about ten hours apart, or about one hour apart in some embodiments.

As is appreciated by a medical practitioner skilled in the art, the dosage of the combination therapy of the invention may vary depending upon various factors such as the pharmacodynamic characteristics of the particular agent and its mode of administration, the age, health and weight of the recipient, the nature and extent of the symptoms, the kind of concurrent treatment, the frequency of treatment, and the effect desired, as described above. The proper dosage of components (a) and (b) will be readily ascertainable by a medical practitioner skilled in the art. By way of general guidance, typically a daily dosage may be about 10 milligrams to about 1.5 grams of each component. If component (b) represents more than one compound, then typically a daily dosage may be about 10 milligrams to about 1.5 grams of each agent of component (b). By way of general guidance, when the compounds of component (a) and component (b) are administered in combination, the dosage amount of each component may be reduced by about 50-80% relative to the usual dosage of the component when it is administered alone as a single agent for the treatment of a disorder, and related symptoms, in view of synergistic effect of the combination.

Pharmaceutical kits useful for the treatment of disorders described herein, and related symptoms, which include a therapeutically effective amount of a pharmaceutical composition that includes a compound of component (a) and one or more compounds of component (b), in one or more sterile containers, are also within the ambit of the invention. Sterilization of the container may be carried out using conventional sterilization methodology well known to those skilled in the art. Component (a) and component (b) may be in the same sterile container or in separate sterile containers. The sterile containers of materials may include separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

An MMP inhibitor described herein can optionally be co-administered with a neuroprotectant drug, used, for example, in the treatment of Alzheimer's disease or other neurologic or ophthalmologic disorders (e.g., glaucoma), including, but not limited to, memantine or a derivative thereof.

An MMP inhibitor described herein can optionally be co-administered with at least one of the following:

An anti-glaucoma agent, beta adrenergic blocking agent, carbonic anhydrase inhibitor, miotic agent, sympathomimetic agent, acetylcholine blocking agent, antihistamine, anti-viral agent, quinolone, anti-inflammatory agent, non-steroidal anti-inflammatory agent, steroidal anti-inflammatory agent, antidepressant (e.g., serotonin reuptake inhibitors, SSRIs), psychotherapeutic agent, anti-anxiety agent, analgesic, antiseizure agent, anti-convulsant, gabapentine, anti-hypertensive agent, benzoporphyrin phtosensitiser, immunosuppressive antimetabolite, barbiturate, benzodiazepine, GABA inhibitors, hydantoin, anti-psychotic, neurolaptic, antidysknetic, adrenergic agent, tricyclic antidepressant, anti-hypoglycemic, glucose solution, plypeptide hormone, antibiotic, thrombolytic agent, blood thinner, anti-arrhythmic agent, corticosteroid, seizure disorder agent, anticholinesterase, dopamine blocker, antiparkinsonian agent, muscle relaxant, anxiolytic muscle relaxant, CNS stimulant, antiemetic, beta adrenergic blocking agents, ergot derivative, isometheptene, antiserotonin agent, analgesic, selective serotonin reuptake inhibitors (SSRIs), monoamine oxidase inhibitor, anti-infective agent, nucleoside reverse transcriptase, a protease inhibitor, or a thrombolytic agent such as tPA.

Specifically, the MMP inhibitor can optionally be co-administered with at least one of the following:

A beta adrenergic blocking agent, carbonic anhydrase inhibitor, cholinesterase inhibitor, cholinergic (miotic), docosanoid, prostaglandin, tricyclic antidepressant, psychotherapeutic agent, antianxiety agent, analgesic, anti-seizure agent, tricyclic antidepressants having analgesic effect in neuropathic pain, linolenic acid, coenzyme, vitamin, immunosuppressive antimetabolite, antiviral, copolymer, barbiturate, benzodiazepine, GABA inhibitor, hydantoin, tranquilizer, anti-psychotic, norephedrine, peptide, antibacterial, tissue plasminogen activator (tPA), blood thinner/anticoagulant, cardiostimulant, carbonic anhydrase inhibitor, ketoderivative of carbamazepine, acetylcholinesterase, antipsychotic, alkaloid, GABA-B receptor agonist, benzodiazepine, antiparkinsonian, antidepressant, CNS stimulant, receptor antagonist, beta adrenergic blocking agent, ergot derivatives (anti migraine), anticonvulsant, serotonin(5-HT) receptor agonist, antimanic, SSRI, MAOI, aids adjunct anti-infective agent, antiviral, or protease inhibitor.

Additionally, the MMP inhibitor can optionally be co-administered with at least one of the following:

Timolol Maleate; Timolol Hemihydrate; Betaxolol HCl; Metipranolol; Brimonidine Tartarate; Brinzolamide; Dorzolamide; Acetazolamide; Echothiophate Iodide; Pilocarpine HCl; Unoprostone Isopropyl ester; Latanoprost; Acamprosate; Amitriptyline; Perphenazine; Chlordiazepoxide; Trimipramine Maleate; Chlodiazepoxide HCl; Alprazolam; Hydroxyzine dihydrochloride; Meprobamate; Doxipin HCl; Hydroxyzine Pamoate; Aspirin; Acetaminophen; Ibuprofen; Carbamazepine; Flupirtine; Lamotrigine; Phenytoin Sodium; Pentaxifylline; Thioctic Acid; Levocarnitine; Biotin; Nicotinic acid; Taurine; Verteporfin; Azathioprine; Interferon Beta 1; Interferon Beta 1; Cyclophosphamide; Methotrexate; Neurmexane; Mephobarbitol; Pentobarbitol; Lorazipam; Clonazepam; Chlorazeptate Dipotassium salt; Fosphenytoin Sodium; Olanzapine; Heloperidol; Trifluoperizine; Fluphenazine; Phenylpropanol amine; Pseudoephedrine HCl; Imipramine; Glucagon; Glucagon-related peptide-1; Glucagon-related peptide-2; Penicilin G,N,O, or V; Ampicillin; Chloramphenicol; Phorbol; Heparin, D-glucosamine with L-iduronic or D-glucuronic acids; Warfarin; Epinephrine; Amiodarone; Lidocaine; Nitroglycerin, isosorbide dinitrate, amyl, butyl, isobutyl or various other nitrates that have been shown to be neuroprotective; Atenolol; Dexamethasone; Prednisolone; Acetazolamide; Phenytoin; Tiagabin HCl; Gabapentin; Oxacarbazepine; Tacrine; Donepezil; Rivastigmine; Heloperidol; Phenothiazine; Reserpine; Tetrabenazene; Bromocryptine; Tiapride; Baclofen; Diazepam; Trihexyphenidyl HCl; Amitrityline; Amphetamines; Methylphenidate; Amitriptylinec; Clomipramine; Dolasetron; Granisetron; Huperzine; Metoclopramide; Prochlorperazine; Dexamethasone; Timolol Hydrogen maleate salt; Propanolol; Isometheptine; Atenolol; Metoprolol; Nadolol; Ergotamine; Dihydroargotamine; Naratriptan; Sumatriptan; Rizatriptan; Zolmitriptan; Imipramine HCl; Dopamine; Clozapine; Valproic Acid; Amitriptylinec; Imipramine HCl; Imipramine Pamoate; Clomipramine; Amphetamine; Methylphenidate; Phenytoin; Phenobarbital; Amitryptyline; Imipramine Pamoate; Nortrityline; Trazodone; Nefazodone; Sertraline; Fluoxetine; Paroxetine; Phenalzine; Tranylcypromine; Erythropoietin, a glycoprotein; Immunoglobulins (gamma globulins); Tetrahydrocannabinols; Alitretinoin; Lamivudin; Stavudin; Zalcitabine; Abacavir; Ritonavir; Indinavir; and Nelfinavir; the chemical names of which are well known in the art and are also described in U.S. Publication No. 2009/0209615 (Liption et al.), which is incorporated herein by reference. The MMP inhibitor can be administered with an additional MMP inhibitors, including a compounds disclosed in U.S. Pat. No. 6,703,415 (Mobashery et al.) and U.S. Pat. No. 7,928,127 (Lee et al.); PCT Publication No. WO 2011/026107 (Mobashery et al.); and U.S. Publication No. 2013/0064878 (Chang et al.); which patent documents are incorporated herein by reference. Any one or more of the above compounds can be used in a pharmaceutically acceptable salt form, solvate form (e.g., a mono- or di-hydrate), or any combination thereof.

Pharmaceutical Salts and Solvates

The invention also includes pharmaceutically acceptable salts and/or solvates of the compounds represented by a formula described herein, such as those described above and of the specific compounds exemplified herein, and methods of treatment using such salts and/or solvates.

A "pharmaceutically acceptable salt" is intended to mean a salt of a free acid or base of a compound represented by a formula described herein that is non-toxic, biologically tolerable, or otherwise biologically suitable for administration to the subject. See, generally, S. M. Berge, et al., "Pharmaceutical Salts", *J. Pharm. Sci.*, 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response.

Pharmaceutically acceptable salts include the addition salts of inorganic acids such as hydrochloride, hydrobromide, hydroiodide, halide, sulfate, phosphate, carbonate, bicarbonate, diphosphate and nitrate or of organic acids such as acetate, malonate, maleate, fumarate, tartrate, succinate, citrate, lactate, benzoate, ascorbate, tosylate, mesylate, triflate, palmoate, stearate, α-ketoglutarate, and α-glycerophosphate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

A compound of a formula described herein may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, behenates, besylates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of a formula described herein contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of a formula described herein includes an acid moiety, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The term "solvate" refers to a solid compound that has one or more solvent molecules associated with its solid structure. Solvates can form when a compound is crystallized from a solvent, wherein one or more solvent molecules become integral part(s) of the crystal. The compounds of a formula described herein can be solvates, for example, ethanol solvates. Likewise, a "hydrate" refers to a solid compound that has one or more water molecules associated with its solid structure. A hydrate is a subgroup of solvates. Hydrates can form when a compound is crystallized from water, wherein one or more water molecules become integral part(s) of the crystal. The compounds of a formula described herein can be hydrates.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis. The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known. The invention also provides therapeutic methods of treating wounds such as chronic wounds and wounds of diabetic patients, and neurological conditions such as stroke and traumatic brain injury, as well as compounds useful for evaluating the role of MMPs in various conditions and disorders, such as the conditions and disorders described herein.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Abbreviations

ADAM, a disintegrin and metalloproteinase; AUC, area under the concentration-time curve, BBB, blood-brain barrier; Boc, t-butoxycarbonyl; m-CPBA, meta-chloroperbenzoic acid; CNS, central nervous system; DIEA, N,N-diisopropylethylamine; DMF, dimethylformamide; DMSO, dimethyl sulfoxide; ESI, electrospray ionization; HCTU, O-(1H-6-Chlorobenzotriazole-1-yl)-1,1,3,3-tetramethyluronium hexafluorophosphate; MMP, matrix metalloproteinase; MOCAc, (7-methoxycoumarin-4-yl)acetyl; MRM, multiple reaction monitoring; MS, mass spectrometry; TEA, triethylamine; THF, tetrahydrofuran; TIMP, tissue inhibitor of metalloproteinase; TLC, thin-layer chromatography; UPLC, ultra-performance liquid chromatography.

Example 1

Selective Water-Soluble and Slow-Binding Matrix Metalloproteinase-2 and -9 Inhibitors that Cross the Blood-Brain Barrier The invention provides selective MMP inhibitors such as p-aminomethyloxadiazol (4), p-aminomethyl (5, ND-336), p-acetamidomethyl (6, ND-378), and p-guanidino (7) analogs of compound SB-3CT (1), and methods for their use. The compounds are 10- to 14,000-fold more water-soluble than 1, retain slow-binding inhibition behavior toward MMP-2, and can cross the blood brain barrier (BBB). The p-acetamidomethyl analog (compound 6) is a selective nanomolar slow-binding inhibitor of MMP-2, which does not inhibit the closely related MMP-9 or MMP-14. Because of the slow dissociation of compound 6 from the target MMP-2, it results in sustained inhibition of MMP-2 even when concentrations of 6 fall below the $K_i$ value. This inhibitor is a useful tool in therapeutic intervention and in investigations of the role of MMP-2 in neurological diseases. The p-aminomethyl derivative (compound 5) is a water-soluble nanomolar slow-binding inhibitor of MMP-2, MMP-9, and MMP-14 and has residence times for inhibition of these enzymes 6- to 7-fold longer than those of the tissue inhibitors of metalloproteinase 1 or 2 (TIMP-1 or TIMP-2) bound to MMP-9.

Chemistry.

The syntheses of the p-aminomethyloxadiazol (4), p-aminomethyl (5, ND-336), p-acetamidomethyl (6, ND-378), and p-guanidino (7) derivatives of 1 are outlined below in Scheme 1. Allylation of 4-mercaptophenol (8) gave compound 9 (Ikejiri et al. *J. Biol. Chem.* 2005, 280, 33992-34002), which was allowed to react with 4-fluorobenzonitrile to afford the diphenyl ether 10. Reaction of 10 with hydroxylamine, followed by the addition of Boc-glycine to the amidoxime generated the oxadiazol derivative 12, which was further oxidized to the corresponding oxirane 13 and subsequently reacted with thiourea to yield the Boc-protected thiirane 14. Boc-deprotection using 4 N HCl in 1,4-dioxane gave the desired thiirane 4. Reduction of 10 with LiAlH$_4$, followed by Boc-protection gave 15. Compound 5 was synthesized from 15 using similar procedures used for the synthesis of 4 from 12. N-acetylation of 5 using acetyl chloride, in the presence of TEA, afforded compound 6. Reaction of 2 with N,N'-di-Boc-1H-pyrazole-1-carboxamidine, using N,N-diisopropylethylamine (DIEA) as base, readily provided thiirane 18, which was then Boc-deprotected with HCl gas to afford the p-guanidino derivative 7.

Scheme 1. Syntheses of the inhibitors 4, 5, 6 and 7[a].
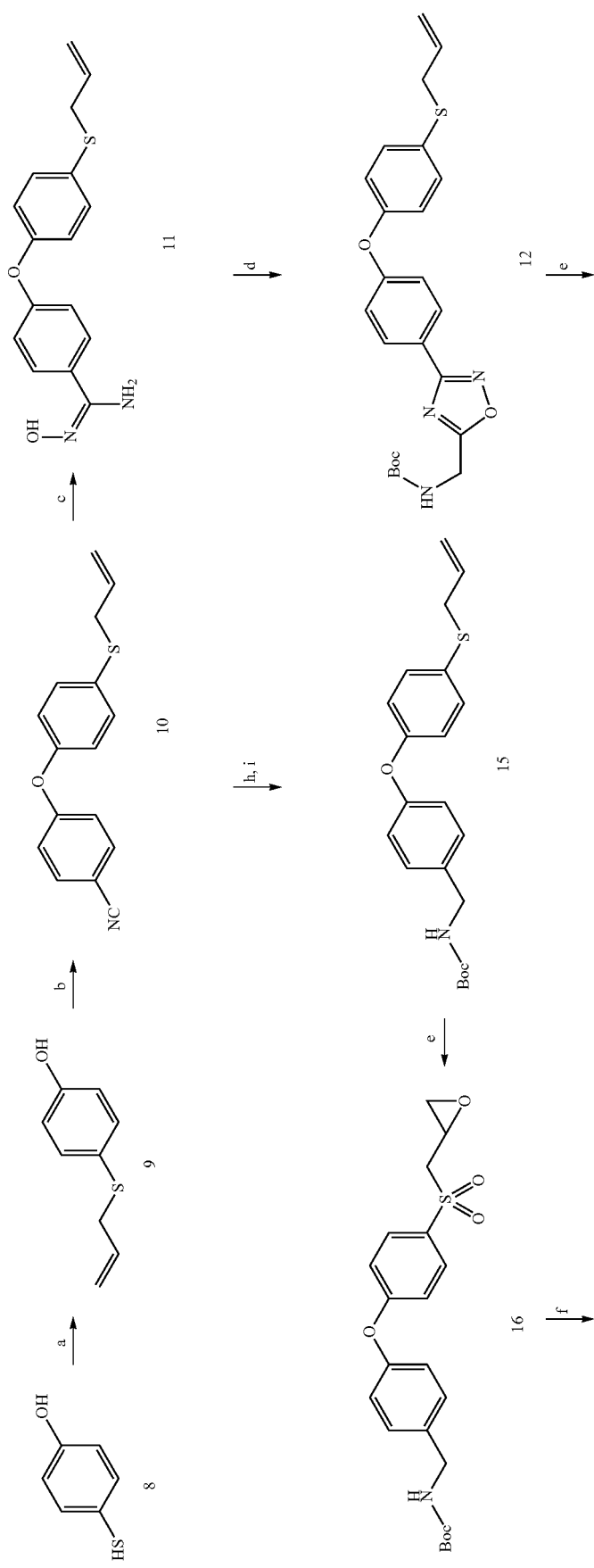

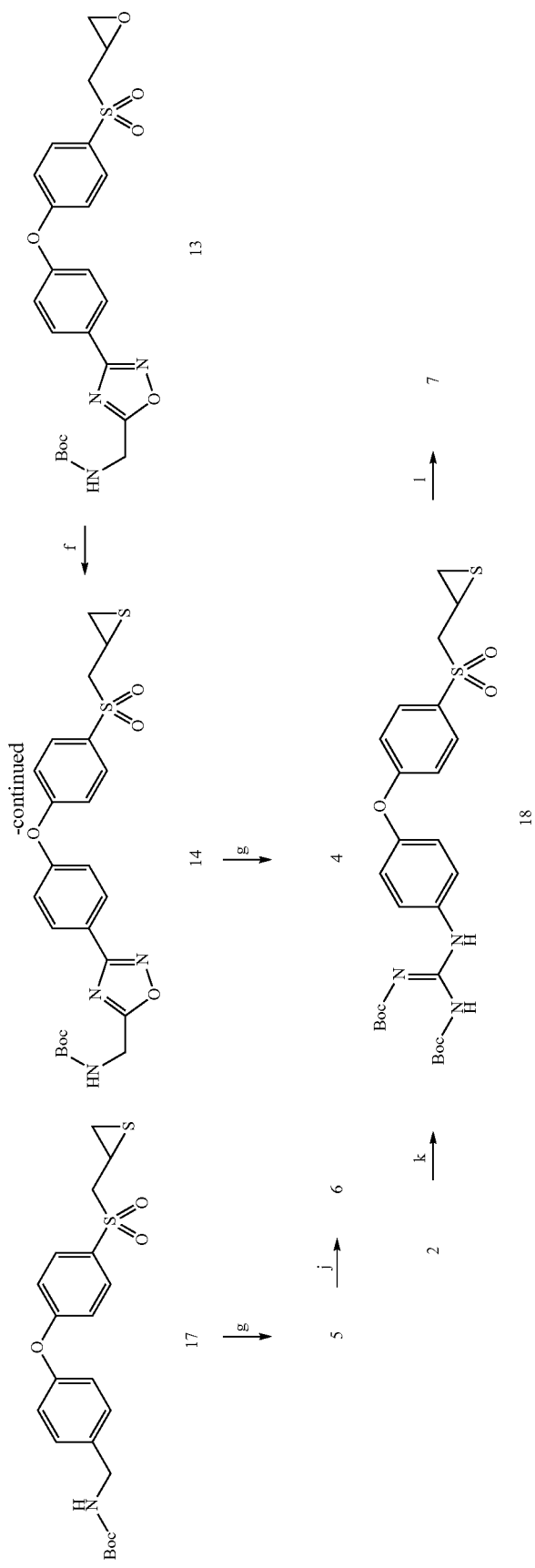

<sup>a</sup> Reagents and conditions:
(a) allyl bromide, K₂CO₃, 94%
(b) 4-fluorobenzonitrile, Cs₂CO₃, DMF, 100° C., 82%;
(c) hydroxylamine (50% in water), EtOH, reflux;
(d) Boc-glycine, HCTU, DIEA, DMF, 100° C., 78% in two steps;
(e) m-CPBA, CH₂Cl₂, 0° C. to room temperature (~22° C.), 8 d, 36-75%;
(f) thiourea, MeOH/CH₂Cl₂, room temperature, 24 h, 58-78%;
(g) 4N HCl (in 1,4-dioxane), EtOAc/CH₂Cl₂, 0° C. to room temperature, 24 h 98-99%;
(h) LiAlH₄, THF;
(i) (Boc)₂O, I₂, MeOH/CH₂Cl₂, 55% in two steps;
(j) acetyl chloride, TEA, THF, 0° C. to room temperature (~22° C.), 66%;
(k) N,N'-di-Boc-1H-pyrazole-1-carboxamidine, DIEA (2.2 eq), THF, room temperature, 24 h 68%;
(l) HCl (gas), EtOAc/CH₂Cl₂, 0° C., 3 min, 95%.

EXPERIMENTAL SECTION

Chemistry.

All reactions were performed under nitrogen atmosphere, unless noted otherwise. $^1$H and $^{13}$C NMR spectra were recorded on Varian INOVA-500 (Varian Inc., Palo Alto, Calif., USA), Varian UnityPlus 300 spectrometer (Varian Inc., Palo Alto, Calif., USA), Bruker AVANCE III HD 500 (Bruker Corporation, Billerica, Mass., USA), or Bruker AVANCE III HD 400 (Bruker Corporation, Billerica, Mass., USA). TLC silica gel 60 $F_{254}$ aluminum sheets (EMD Millipore Corporation, Billerica, Mass., USA) were used for thin-layer chromatography. Flash chromatography was performed with an automated chromatograph system: Combiflash RF 200i UV/Vis (Teledyne Isco, Lincoln, Nebr., USA). High-resolution mass spectra were obtained by ESI ionization, using a BrukermicrOTOF/Q2 mass spectrometer (BrukerDaltonik, Bremen, Germany). Purity of the prepared compounds was in general >95%, as confirmed by UPLC. Conditions are detailed in the UPLC section. 4-(Allylthio) phenol (9) was prepared as previously described (Ikejiri et al., *J. Biol. Chem.* 2005, 280, 33992-34002; Goux et al., C.; *Tetrahedron* 1994, 50, 10321-10330).

4-(4-(Allylthio)phenoxy)benzonitrile (10)

A mixture of 9 (1.45 g, 8.72 mmol), 4-fluorobenzonitrile (1.01 g, 8.38 mmol), and $Cs_2CO_3$ (4.26 g, 13.1 mmol) in DMF (50 mL) was heated at 100° C. for 3.5 h. After the addition of saturated aqueous LiBr (250 mL), the mixture was extracted with hexanes/EtOAc (9:1). The combined organic layers were washed with water and brine, dried over anhydrous $Na_2SO_4$, and concentrated under reduced pressure. The resultant residue was purified by silica gel chromatography (hexanes/EtOAc, 97:3) to give 5 (1.84 g, 82%) as an oil. $^1$H NMR (300 MHz, $CDCl_3$) δ 7.77-7.52 (m, 2H), 7.49-7.30 (m, 2H), 7.14-6.82 (m, 4H), 5.87 (ddt, J=16.9, 10.0, 6.9 Hz, 1H), 5.29-4.93 (m, 2H), 3.53 (dt, J=6.9, 1.1 Hz, 2H). $^{13}$C NMR (126 MHz, $CDCl_3$) δ 161.6, 153.9, 134.4, 133.7, 132.7, 132.4, 121.0, 119.0, 118.2, 118.1, 106.3, 38.2. HRMS (ESI+, m/z): calcd for $C_{16}H_{14}NO$ $[M+H]^+$, 268.0791. found, 268.0799.

(E)-4-(4-(Allylthio)phenoxy)-N'-hydroxybenzimidamide (11)

A solution of 10 (865 mg, 3.24 mmol) and hydroxylamine (793 μL, 50% in water, 12.9 mmol) in EtOH (40 mL) was refluxed for 1.5 h. The solvent was evaporated under reduced pressure to give 11 as a white solid, which was used directly in the next step without further purification.

t-Butyl ((3-(4-(4-(allylthio)phenoxy)phenyl)-1,2,4-oxadiazol-5-yl)methyl)carbamate (12)

DIEA (1.05 mL, 5.93 mmol) was added to a solution of Boc-glycine (692 mg, 3.95 mmol) and 11 (989 mg, 3.29 mmol) in DMF (16 mL). HCTU (1.64 g, 3.95 mmol) was then added to the resulting mixture at room temperature and stirred at 100° C. for 3 h. At this time, the TLC showed complete conversion of starting materials. The solution was partitioned between EtOAc and LiBr aqueous solution. The aqueous solution was extracted with EtOAc and the combined organic layers were washed with saturated $NaHCO_3$ and brine, dried over anhydrous $Na_2SO_4$ and concentrated in vacuo. The residue was purified by silica gel chromatography (hexanes/EtOAc, 85:15) to give 12 (1.13 g, 78% in two steps). $^1$H NMR (500 MHz, $CDCl_3$) δ 8.03 (d, J=8.6 Hz, 2H), 7.43-7.35 (m, 2H), 7.05 (d, J=8.7 Hz, 2H), 7.02-6.97 (m, 2H), 5.95-5.80 (m, 1H), 5.22 (s, b, 1H), 5.15-5.02 (m, 2H), 4.64 (s, 2H), 3.52 (d, J=7.0 Hz, 2H), 1.48 (s, 9H). $^{13}$C NMR (126 MHz, $CDCl_3$) δ 176.7, 168.1, 160.2, 155.7, 155.2, 132.9, 131.2, 131.0, 129.5, 120.7, 120.4, 118.6, 118.0, 80.9, 38.5, 37.4, 28.6. HRMS (ESI+, m/z): calcd for $C_{23}H_{26}N_3O_4S$ $[M+H]^+$, 440.1639. found, 440.1634.

t-Butyl ((3-(4-(4-((oxiran-2-ylmethyl)sulfonyl)phenoxy)phenyl)-1,2,4-oxadiazol-5-yl)methyl)carbamate (13)

m-CPBA (2.03 g, 11.8 mmol) was added in batches to a solution of 12 (1.04 g, 2.36 mmol) in $CH_2Cl_2$ (8 mL) immersed in an ice-water bath. After completion of the addition, the ice-water bath was removed and the solution was stirred at room temperature for 3 days. Another batch of m-CPBA (1.02 g, 5.89 mmol) was added, and the mixture was stirred at room temperature for an additional 5 d. The suspension was filtered, and the filtrate was diluted with $CH_2Cl_2$ and washed with 10% aqueous sodium thiosulfate, followed by saturated $NaHCO_3$ and brine. The organic layer was dried over anhydrous $Na_2SO_4$, the suspension was filtered, and the solution was concentrated in vacuo. The product was purified by silica gel chromatography (hexanes/ EtOAc, 2:1 to 1:1) to yield 13 (0.85 g, 74%). $^1$H NMR (500 MHz, $CDCl_3$) δ 8.05 (d, J=8.8 Hz, 2H), 7.87 (d, J=8.9 Hz, 2H), 7.11 (d, J=8.9 Hz, 4H), 5.58 (s, b, 1H), 4.59 (d, J=5.8 Hz, 2H), 3.38-3.24 (m, 3H), 2.79-2.76 (m, 1H), 2.55-2.34 (m, 1H), 1.42 (s, 9H). $^{13}$C NMR (126 MHz, $CDCl_3$) δ 176.9, 173.9, 167.9, 162.1, 157.8, 133.7, 131.0, 129.9, 123.5, 120.6, 118.7, 81.1, 59.9, 46.13, 46.12, 37.5, 28.6. HRMS (ESI+, m/z): calcd for $C_{23}H_{26}N_3O_7S$ $[M+H]^+$, 488.1486. found, 488.1498.

t-Butyl ((3-(4-(4-((thiiran-2-ylmethyl)sulfonyl)phenoxy)phenyl)-1,2,4-oxadiazol-5-yl)methyl)carbamate (14)

Thiourea (55.3 mg, 0.73 mmol) was added to a solution of compound 13 (161.1 mg, 0.33 mmol) in MeOH/$CH_2Cl_2$ (1:1, 3 mL), and the resulting mixture was stirred at room temperature for 24 h. The solvent was removed under reduced pressure and the residue was partitioned between $CH_2Cl_2$ and water. The organic layer was washed with water and brine, dried over anhydrous $Na_2SO_4$, and filtered. Evaporation of the solvent gave the crude product, which was purified by silica gel chromatography (130.1 mg, 78%). $^1$H NMR (300 MHz, $CDCl_3$) δ 8.13 (d, J=8.9 Hz, 2H), 7.92 (d, J=8.7 Hz, 2H), 7.18 (d, J=8.5 Hz, 4H), 5.30 (s, b, 1H), 4.65 (s, 2H), 3.52 (dd, J=14.0, 5.8 Hz, 1H), 3.22 (dd, J=14.3, 7.6 Hz, 1H), 3.16-2.99 (m, 1H), 2.56 (dd, J=6.0, 1.6 Hz, 1H), 2.18 (dd, J=5.0, 1.6 Hz, 1H), 1.48 (s, 9H). $^{13}$C NMR (75 MHz, $CDCl_3$) δ 177.0, 167.9, 162.1, 157.9, 143.2, 133.2, 131.2, 130.0, 123.5, 120.5, 118.8, 77.5, 62.9, 37.5, 28.5, 26.3, 24.4. HRMS (ESI+, m/z): calcd for $C_{23}H_{26}N_3O_6S2$ $[M+H]^+$, 504.1258. found, 504.1247.

(3-(4-(4-((Thiiran-2-ylmethyl)sulfonyl)phenoxy) phenyl)-1,2,4-oxadiazol-5-yl)methanamine.HCl salt (4)

HCl (0.7 mL, 4 N in 1,4-dioxane) was added to a solution of thiirane 14 (71 mg, 0.14 mmol) in $CH_2Cl_2$/EtOAc (1:1, 4 mL). After stirring at room temperature for 24 h, the mixture was concentrated under reduced pressure. The resulting crude compound was triturated with diethyl ether, and the product was obtained by filtration (60.5 mg, 98%). $^1$H NMR (300 MHz, CD$_3$OD) δ 8.32-8.12 (m, 2H), 8.09-7.92 (m, 2H), 7.42-7.20 (m, 4H), 4.62 (s, 2H), 3.65-3.41 (m, 2H), 3.11-3.03 (m, 1H), 2.53 (dd, J=6.5, 1.5 Hz, 1H), 2.16 (dd, J=5.2, 1.5 Hz, 1H). $^{13}$C NMR (75 MHz, CD$_3$OD) δ 174.7, 169.2, 163.0, 159.8, 134.8, 132.4, 130.8, 123.8, 121.4, 120.0, 63.1, 36.2, 26.9, 24.1. HRMS (ESI+, m/z): Calcd for C$_{18}$H$_{18}$N$_3$O$_4$S$_2$[M+H]$^+$, 404.0733. found, 404.0746.

t-Butyl 4-(4-(allylthio)phenoxy)benzylcarbamate (15)

A solution of compound 10 (4.98 g, 18.63 mmol) in THF (78 mL) was added dropwise to LiAlH$_4$ (2.12 g, 55.89 mmol) in THF (78 mL) at 0° C. over a period of 30 min. The ice-bath was removed and the reaction mixture was stirred at room temperature for 1.5 h at which point the TLC showed the reaction to be complete. The solution was cooled again to ice-water temperature and quenched carefully with the dropwise addition of 2.4 mL water, 2.4 mL 15% aqueous NaOH, and 7.2 mL water. The solution was gradually warmed to room temperature and stirred for 30 min, filtered through a celite pad, extracted with diethyl ether and EtOAc. The combined organic layer was washed with water and brine, and the solution was dried over anhydrous Na$_2$SO$_4$. The solvent was evaporated under reduced pressure to give the crude primary amine, which was used directly in the next step.

To a mixture of amine (4.3 g, 15.84 mmol) and (Boc)$_2$O (5.2 g, 23.77 mmol) in MeOH/CH$_2$Cl$_2$ (3:2, 150 mL), was added a catalytic amount of iodine (402 mg, 1.58 mmol, 10 mol %). After stirring the reaction mixture for 24 h at room temperature, the solvent was evaporated in vacuo, and EtOAc was added. The solution was washed with 5% aqueous Na$_2$S$_2$O$_3$ and saturated NaHCO$_3$, and dried over anhydrous Na$_2$SO$_4$. The solvent was evaporated in vacuo, and the residue was purified by silica gel chromatography (hexanes/EtOAc, 95:5) to afford compound 15 (3.21 g, 55% in two steps). $^1$H NMR (300 MHz, CDCl$_3$) δ 7.38-7.32 (m, 2H), 7.31-7.25 (m, 2H), 6.99-6.90 (m, 4H), 6.17-6.09 (m, 1H), 5.08-5.03 (m, 2H), 4.85 (s, b, 1H), 4.29 (d, J=3.0 Hz, 2H), 3.49-3.47 (m, 2H), 1.46 (s, 9H). $^{13}$C NMR (75 MHz, CDCl$_3$) δ 156.8, 156.4, 156.1, 134.0, 133.2, 131.4, 131.2, 129.2, 127.2, 119.3, 117.7, 79.7, 44.4, 38.8, 28.6. HRMS (ESI+, m/z): calcd for C$_{21}$H$_{25}$NNaO$_3$S [M+Na]$^+$, 394.1447. found, 394.1472.

t-Butyl 4-(4-((oxiran-2-ylmethyl)sulfonyl)phenoxy) benzylcarbamate (16)

Compound 16 was prepared following the same procedure as described for the synthesis of compound 13. Yield, 36%. $^1$H NMR (400 MHz, CDCl$_3$) δ 7.91-7.65 (m, 2H), 7.27-7.25 (m, 2H), 7.06-6.95 (m, 4H), 5.22 (s, b, 1H), 4.24 (d, J=5.1 Hz, 2H), 3.44-3.02 (m, 3H), 2.72 (dd, J=8.0, 2.0 Hz, 1H), 2.39 (dd, J=4.8, 2.0 Hz, 1H), 1.39 (s, 9H). $^{13}$C NMR (100 MHz, CDCl$_3$) δ 163.0, 154.1, 136.6, 130.7, 129.5, 123.2, 120.7, 118.0, 117.8, 79.7, 59.8, 46.04, 45.99, 44.1, 28.6. HRMS (ESI+, m/z): calcd for C$_{21}$H$_{25}$NNaO$_6$S [M+Na]$^+$, 442.1295. found, 442.1292.

t-Butyl 4-(4-((thiiran-2-ylmethyl)sulfonyl)phenoxy) benzylcarbamate (17)

Compound 17 was prepared following the same procedure as described for the synthesis of compound 14. Yield, 58%. $^1$H NMR (300 MHz, CDCl$_3$) δ 7.85 (d, J=8.7 Hz, 2H), 7.33 (d, J=8.7 Hz, 2H), 7.13-6.97 (m, 4H), 4.95 (s, b, 1H), 4.33 (d, J=5.9 Hz, 2H), 3.51 (dd, J=14.1, 5.7 Hz, 1H), 3.17 (dd, J=14.1, 7.8 Hz, 1H), 3.11-2.98 (m, 1H), 2.53 (dd, J=6.3, 1.6 Hz, 1H), 2.15 (dd, J=5.1, 1.6 Hz, 1H), 1.46 (s, 9H). $^{13}$C NMR (75 MHz, CDCl$_3$) δ 163.1, 156.0, 154.0, 136.3, 132.1, 130.8, 129.4, 120.7, 117.8, 79.8, 62.8, 44.1, 28.5, 26.2, 24.4. HRMS (ESI+, m/z): calcd for C$_{21}$H$_{25}$NNaO$_5$S$_2$[M+Na]$^+$, 458.1066. found, 458.1089.

(4-(4-((Thiiran-2-ylmethyl)sulfonyl)phenoxy)phenyl)methanamine HCl salt (5)

Compound 5 was prepared following the same procedure as described for the synthesis of compound 4. Yield, 98%. $^1$H NMR (300 MHz, CD$_3$OD) δ 7.93 (d, J=8.6 Hz, 2H), 7.58 (d, J=8.6 Hz, 2H), 7.19 (d, d, J=8.4 Hz, 4H), 4.16 (s, 2H), 3.57-3.43 (m, 2H), 3.11-2.99 (m, 1H), 2.52 (dd, J=6.3, 1.4 Hz, 1H), 2.14 (dd, J=5.1, 1.4 Hz, 1H). $^{13}$C NMR (75 MHz, CD$_3$OD) δ 162.5, 156.2, 133.0, 131.3, 131.1, 130.0, 120.7, 118.2, 62.0, 42.6, 25.8, 23.0. HRMS (ESI+, m/z): calcd for C$_{16}$H$_{18}$NO$_3$S$_2$[M+H]$^+$, 336.0723. found, 336.0709.

N-(4-(4-((Thiiran-2-ylmethyl)sulfonyl)phenoxy) benzyl)acetamide (6)

Acetyl chloride (43.6 μL, 0.61 mmol) in THF (0.5 mL) was slowly added to a cooled solution of 5 (69 mg, 0.19 mmol), triethylamine (85.4 μL, 0.61 mmol) in THF (1.0 mL). The reaction mixture was stirred for 3 h under ice-water bath, warmed to room temperature, and allowed to stir overnight. The reaction was quenched with saturated NaHCO$_3$ and the product was extracted with CH$_2$Cl$_2$. The combined organic layers were dried over anhydrous Na$_2$SO$_4$, filtered, and evaporated to dryness. The residue was purified by preparative TLC (hexanes/EtOAc/MeOH, 14:85:1) to give 6 (45.8 mg, 65%). $^1$H NMR (500 MHz, CDCl$_3$) δ 7.87 (d, J=8.5 Hz, 2H), 7.36 (d, J=8.5 Hz, 2H), 7.08 (d, d, J=8.6 Hz, 4H), 6.03 (s, b, 1H), 4.47 (d, J=5.9 Hz, 2H), 3.52 (dd, J=14.2, 5.7 Hz, 1H), 3.21 (dd, J=14.2, 7.7 Hz, 1H), 3.14-2.98 (m, 1H), 2.56 (dd, J=6.2, 1.6 Hz, 1H), 2.18 (dd, J=5.1, 1.6 Hz, 1H), 2.07 (s, 3H). $^{13}$C NMR (126 MHz, CDCl$_3$) δ 170.1, 163.0, 154.5, 135.8, 132.6, 130.9, 129.9, 120.8, 118.0, 63.0, 43.3, 26.2, 24.4, 23.4. HRMS (ESI+, m/z): calcd for C$_{18}$H$_{20}$NO$_4$S$_2$[M+H]$^+$, 378.0828. found, 378.0836.

1-(4-(4-((Thiiran-2-ylmethyl)sulfonyl)phenoxy)phenyl)-2,3-bis(t-butoxycarbonyl)guanidine (18)

DIEA (31 μL, 0.17 mmol) was added to a solution of compound 2 (56.8 mg, 0.16 mmol) and (Z)-t-butyl (((t-butoxycarbonyl)imino)(1H-pyrazol-1-yl)methyl)carbamate (44.3 mg, 0.14 mmol) in THF (0.5 mL). The resulting reaction mixture was stirred at room temperature for 24 h. The organic solvent was removed under reduced pressure and the residue was purified by preparative TLC (hexanes/EtOAc, 3:1) to give 18 (54.8 mg, 68%). $^1$H NMR (300 MHz, CDCl$_3$) δ 11.64 (s, 1H), 10.40 (s, 1H), 7.85 (d, J=8.7 Hz, 2H), 7.67 (d, J=8.7 Hz, 2H), 7.07 (d, d, J=8.8 Hz, 4H), 3.53 (dd, J=13.9, 5.3 Hz, 1H), 3.16 (dd, J=13.9, 8.1 Hz, 1H), 3.09-3.01 (m, 1H), 2.54 (dd, J=6.1, 1.6 Hz, 1H), 2.16 (dd, J=4.8, 1.6 Hz, 1H), 1.52 (s, s, 18H); $^{13}$C NMR (75 MHz, CDCl$_3$) δ 163.6, 163.3, 153.8, 153.6, 151.5, 134.3, 132.0, 131.0, 124.3, 121.2, 117.8, 84.2, 80.2, 62.9, 28.4, 28.4, 26.4, 24.6; HRMS (ESI+, m/z): calcd for C$_{26}$H$_{34}$N$_3$O$_7$S$_2$[M+H]$^+$, 564.1833. found, 564.1836.

1-(4-(4-((Thiiran-2-ylmethyl)sulfonyl)phenoxy)phenyl)guanidine HCl salt (7)

Hydrogen chloride gas was passed through a solution of 18 (37.1 mg) in $CH_2Cl_2$/EtOAc (1:1, 3 mL) under ice-water temperature for 3 min. The organic solvent was then removed under reduced pressure to give 7 (37.1 mg, 95%). $^1$H NMR (500 MHz, DMSO-$d_6$) δ 9.92 (s, 1H), 7.91 (d, J=8.8 Hz, 2H), 7.50 (s, 3H), 7.34 (d, J=8.8 Hz, 2H), 7.28-7.16 (m, 4H), 3.66 (m, 2H), 2.99 (m, 1H), 2.56 (dd, J=6.0, 1.0 Hz, 1H), 2.16 (dd, J=5.0, 1.0 Hz, 1H). $^{13}$C NMR (126 MHz, DMSO-d6) δ 162.5, 157.0, 153.7, 133.3, 132.7, 131.5, 128.1, 122.2, 118.4, 61.3, 27.7, 24.6. HRMS (ESI+): calcd for $C_{16}H_{18}N_3O_3S_2[M+H]^+$, 364.0784. found, 364.0770.

Enzyme Inhibition Studies.

Human recombinant active MMP-2 and MMP-7, and the catalytic domains of MMP-3 and MMP-14/MT1-MMP were purchased from EMD Chemicals, Inc. (San Diego, Calif., USA); human recombinant catalytic domains of MMP-1, MMP-8, and MMP-9 were purchased from Enzo Life Sciences, Inc. (Farmingdale, N.Y., USA); human recombinant active ADAM9 and ADAM10 were purchased from R&D Systems (Minneapolis, Minn., USA). Fluorogenic substrates MOCAc-Pro-Leu-Gly-Leu-A2pr(Dnp)-Ala-Arg-$NH_2$ (for MMP-2, MMP-7, MMP-9 and MMP-14) and MOCAc-Arg-Pro-Lys-Pro-Val-Glu-Nva-Trp-Arg-Lys(Dnp)-$NH_2$ (for MMP-3) were purchased from Peptides International (Louisville, Ky., USA); Mca-KPLGL-Dpa-AR-$NH_2$ (for MMP-1, MMP-8 and ADAM10) and Mca-PLAQAV-Dpa-RSSSR-$NH_2$ (for ADAM9) were purchased from R&D Systems (Minneapolis, Minn., USA). The $K_m$ values for MMP-2, MMP-9 and MMP-14 were as previously reported by Gooyit et al., *J. Med. Chem.* 2013, 56, 8139-8150. Inhibitor stock solutions (10 mM) were prepared fresh in DMSO before enzyme inhibition assays. We followed the same methodology for enzyme inhibition studies as reported by Page-McCaw et al. (*Nat. Rev. Mol. Cell Biol.* 2007, 8, 221-233). Enzyme inhibition studies were carried out using a Cary Eclipse fluorescence spectrophotometer (Varian, Walnut Creek, Calif., USA). Compounds 4, 5, 6 and 7 were stable in the buffers that were used in the kinetic assays.

Computational Analysis.

MMP-2 protein coordinates were obtained from our previous QM/MM study (Zhou et al., *J. Chem. Theory Comput.* 2010, 6, 3580-3587). Coordinates of MMP-9 and MMP-14 were downloaded from the Protein Data Bank (PDB codes of 1GKC and 3MA2, respectively) and prepared using Protein Preparation Wizard via Maestro v 9.3.5 (Schrodinger LLC, Portland, Oreg., USA). Compounds were prepared using LigPrep v2.55. Molecular docking of the compounds to the catalytic site of MMPs was carried out with Glide v5.8, implementing 1-Å core restraints of the thiirane group and scored with Standard Precision (Friesner et al., *J. Med. Chem.* 2004, 47, 1739-1749).

Animals.

Mice (male CD-1, 6-7 weeks old, ~30 g body weight, specific pathogen free) were purchased from Charles River Laboratories, Inc. (Wilmington, Mass., USA). Mice were fed Teklad 2019 Extruded Rodent Diet (Harlan, Madison, Wis., USA) and provided with water ad libitum. Animals were housed in polycarbonate shoebox cages containing Bed-o'Cobs ¼" (The Andersons Inc., Maumee, Ohio)/Alpha-dri (Sheperd Specialty Papers, Inc., Richland, Mich.) bedding under a 12 h light/12 h dark cycle at 72±2° F.

Animal Dosing and Sample Collection.

Compounds 4, 5, 6, and 7 were formulated as a solution at a concentration of 1.25 mg/mL. Compounds 4, 5, and 7 were dissolved in 73% water/20% propylene glycol/7% DMSO. Compound 6 was dissolved in 61% water/27% propylene glycol/12% DMSO. Mice were given a single 120-µL iv dose of compounds 4, 5, 6, or 7 (equivalent to 5 mg/kg, n=3 per time point). The sterilization of the dosing solutions and the procedure for collection of both plasma and brain as reported by Gooyit et al. (*J. Med. Chem.* 2013, 56, 8139-8150).

Sample Analysis.

Procedures for the preparation of plasma and brain samples, as well as calibration curves for quantification analysis, were as described by Gooyit et al. (*J. Med. Chem.* 2013, 56, 8139-8150). Samples were analyzed by ultraperformance liquid chromatography (UPLC)/(+)electrospray ionization (ESI)-multiple-reaction monitoring (MRM) with a reversed phase C18 column (Acclaim® RSLC 120 C18, 2.2 µm, 120 Å, 2.1×100 mm, Dionex, Sunnyvale, Calif., USA). The chromatographic and mass spectrometric conditions were as previously reported by Gooyit et al. (*J. Med. Chem.* 2013, 56, 8139-8150), except for the following: the capillary voltage, cone voltage, extractor voltage, and RF lens voltage were set at 4.6 kV, 25 V, 3 V, and 0.1 V, respectively; the cone gas-flow rate was set at 50 L/h (nitrogen). The MRM transitions were 404→209 for 4, 319→182 for 5, 378→182 for 6, 364→227 for 7, and 300→93 for internal standard 19.

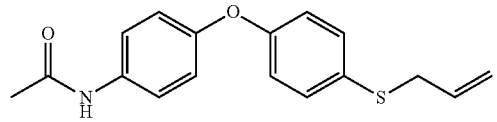

19

Quantification of the compounds in plasma and brain was obtained using peak-area ratios of the compounds to the internal standard, and the linear-regression parameters obtained from the calibration curves. The coefficients of determination ($R^2$) were >0.99, and the assays were linear up to concentrations of 100 µM.

Pharmacokinetic Parameters.

The methodology for the calculation of pharmacokinetic parameters listed in Table 3 is as reported by Gooyit et al. (*J. Med. Chem.* 2013, 56, 8139-8150).

Example 2

Figure 5:
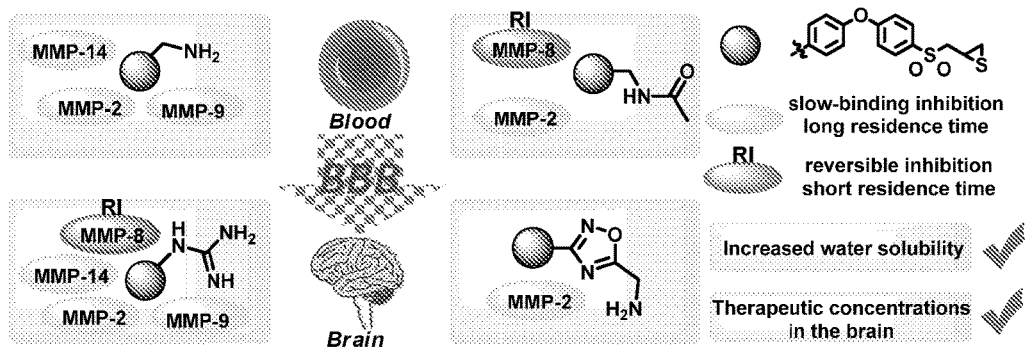
FIG. 5. A schematic showing that compounds ND-336, ND-378, 4, and 7, cross the blood-brain barrier and achieve therapeutic concentrations in the brain.

Selective Water-Soluble and Slow-Binding Matrix Metalloproteinase Inhibitors for Traumatic Brain Injury Therapy, for Neurological Diseases, and for Wound Healing Therapy Traumatic brain injury (TBI) is a devastating disease caused by primary and secondary injuries that can lead to a chronic disease process characterized by persistent cognitive deficits. This disease process starts with biochemical changes that result in brain cell damage and cell death over months to years later. Matrix metalloproteinase-9 (MMP-9) is at the top of the biochemical cascade of events that lead to secondary injury. We have shown that selective inhibition of MMP-9 attenuates secondary damage resulting from TBI. We have created water-soluble selective MMP-9 inhibitors to address the therapeutic need in the area of TBI treatment (Table 2.1). The compounds ND-336 and ND-378 cross the blood-brain barrier and achieve therapeutic concentrations in the brain (FIG. 5).

TABLE 2.1

| ND-336 (5) | ND-378 (6) |
|---|---|
| Ki (MMP-2) 0.085 ± 0.001 μM (slow-binding) | Ki (MMP-2) 0.234 ± 0.006 μM (slow-binding) |
| Ki (MMP-9) 0.150 ± 0.005 μM (slow-binding) | Ki (MMP-9) 23% inhibition at 50 μM |
| Ki (MMP-14) 0.120 ± 0.005 μM (slow-binding) | Ki (MMP-14) 23% inhibition at 50 μM |
| Ki (MMP-8) 7.72 ± 0.07 μM (linear noncompetitive) | Ki (MMP-8) 0.692 ± 0.042 μM (linear competitive) |
| Ki (MMP-1) 4% inhibition at 100 μM | Ki (MMP-1) 37% inhibition at 100 μM |
| Ki (MMP-3) 23% inhibition at 100 μM | Ki (MMP-3) 14% inhibition at 100 μM |
| Ki (MMP-7) 1% inhibition at 100 μM | Ki (MMP-7) 4.7% inhibition at 100 μM |
| Ki (ADAM-9) 31% inhibition at 100 μM | Ki (ADAM-9) 31% inhibition at 100 μM |
| Ki (ADAM-10) 14% inhibition at 100 μM | Ki (ADAM-10) 8% inhibition at 100 μM |
| Water Solubility 4.9 mg/mL | Water Solubility 0.025 mg/mL |

Gelatinases (matrix metalloproteinases (MMP)-2 and 9) play important roles in the pathology of many neurological diseases, as well as in wound healing. A major challenge to the development of therapeutics for the treatment of neurological diseases is the inability of >98% of small-molecule drugs to cross the blood-brain barrier (BBB) and achieve therapeutic concentrations in the brain.

SB-3CT (compound 1) is a selective slow-binding and potent inhibitor of gelatinases that shows efficacy in animal models of neurological diseases. However, this compound is poorly water-soluble. We synthesized and evaluated p-aminomethyloxadiazol (4), p-aminomethyl (5, ND-336), p-acetamidomethyl (6, ND-378), and p-guanidino (7) compounds as improvements on compound 1. The compounds are 10- to 14,000-fold more water-soluble than 1, retained slow-binding inhibition behavior towards MMP-2, and cross the BBB.

The p-acetamidomethyl analog (compound 6) is a selective nanomolar slow-binding inhibitor of MMP-2, which does not inhibit the closely related MMP-9 or MMP-14. Because of the slow dissociation of compound 6 from the target MMP-2 (residence time of 6 bound to MMP-2 is 18.2±0.4 min), it results in sustained inhibition of MMP-2 even when concentrations of 6 fall below the $K_i$ value. This inhibitor is a useful tool in therapeutic intervention and in investigations of the role of MMP-2 in neurological diseases. The p-aminomethyl derivative (compound 5) is a water-soluble nanomolar slow-binding inhibitor of MMP-2, MMP-9, and MMP-14 and has residence times for inhibition of these enzymes 6- to 7-fold longer than those of the tissue inhibitors of metalloproteinase 1 or 2 (TIMP-1 or TIMP-2) bound to MMP-9, protein inhibitors that have evolved for the purpose of regulating MMPs.

Figure 3:
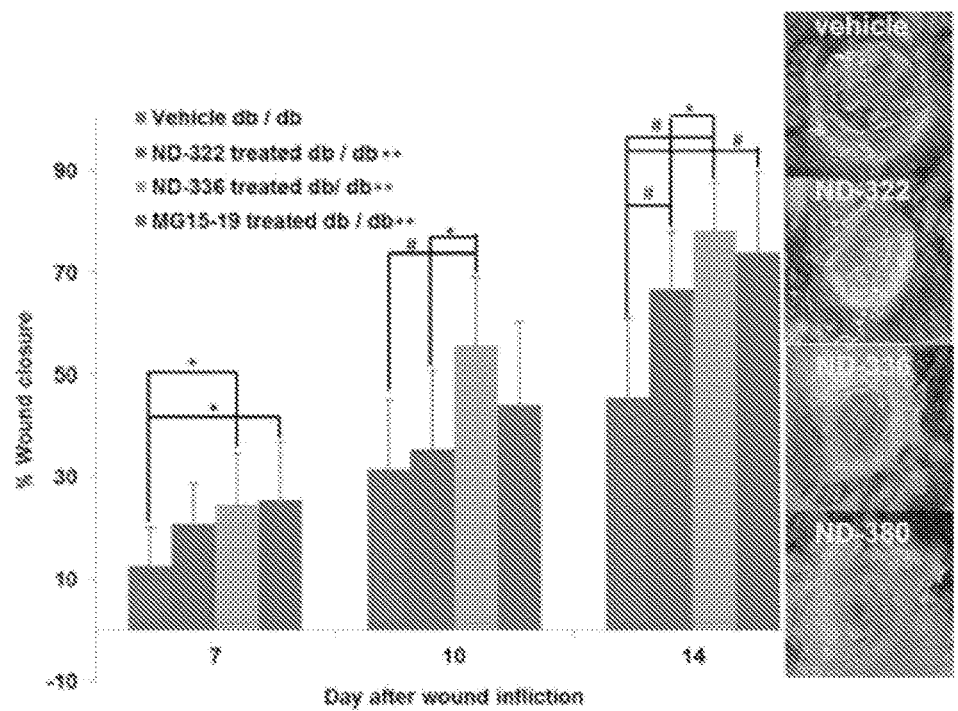
FIG. 3. Data from experiments involving a mouse model of diabetic wound healing showing that ND-336 provides significantly better efficacy than ND-322. Left column=vehicle; second from left column=ND-322; second from right column=ND-336; right column=ND-380.
Figure 4:
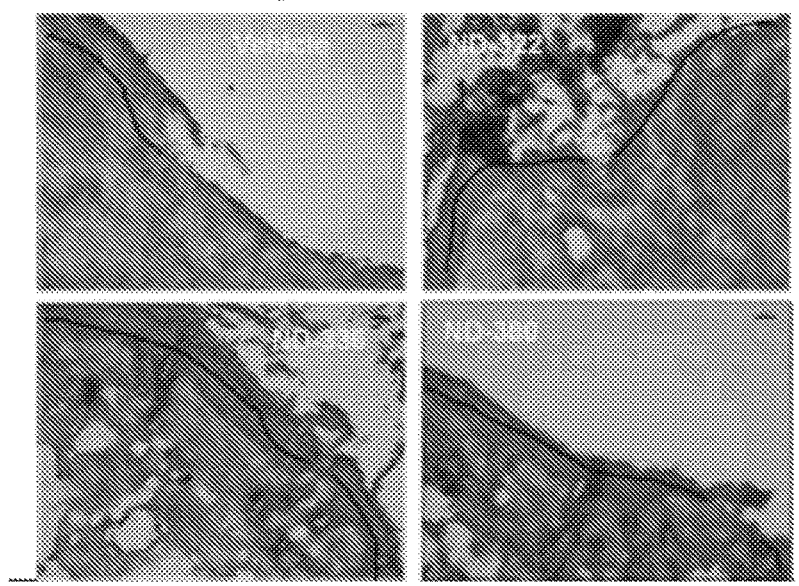
FIG. 4. Picture showing re-epithilialization in the presence of a control (vehicle), ND-322, ND-336, and ND-380.

Chronic wounds are a complication of diabetes. We previously showed that MMP-9 is detrimental to wound healing, while MMP-8 is involved in repair of wounds. The p-aminomethyl compound ND-336 has better selectivity towards MMP-9 than the p-amino compound ND-322 (Table 2.2). In experiments involving a mouse model of diabetic wound healing, ND-336 showed significantly better efficacy than ND-322 (FIGS. 3 and 4).

Figure 6:
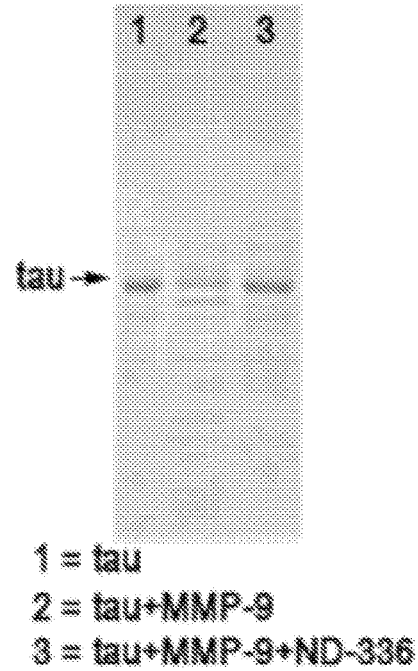
FIG. 6. Gel experiment showing that ND-336 prevents cleavage of tau in the presence of MMP-9.

ND-336 is >2,000-fold more water-soluble than SB-3CT, 4-fold more potent towards inhibition of MMP-9 than SB-3CT, it crosses the BBB, and achieves therapeutic concentrations in the brain. Furthermore, we have shown that MMP-9 cleaves tau and that ND-336 prevents cleavage of tau (FIG. 6). Because cleaved tau can lead to chronic neurodegeneration after traumatic brain injury (TBI) and plays an important role in the pathology of Alzheimer's disease and chronic traumatic encephalopathy, ND-336 can be used to reverse cognitive dysfunction following TBI.

TABLE 2.2

| | MMP-9 Ki (nM) | MMP-8 Ki (nM) |
|---|---|---|
| ND-322 (2) | 870 ± 110 | 2600 ± 400 |
| ND-336 (5) | 150 ± 10 | 7700 ± 100 |

TABLE 2.2-continued

| | MMP-9 Ki (nM) | MMP-8 Ki (nM) |
|---|---|---|
| 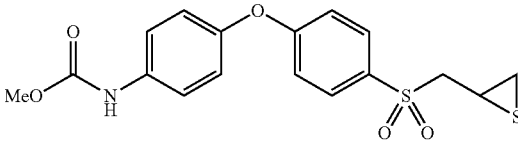 ND-380 | 180 ± 30 | 13000 ± 2000 |

ND-378 is also a selective MMP-2 inhibitor that also crosses the BBB. Recent efforts in defining the role of MMPs in cancer have correlated increased expression of MMP-2 with aggressive breast cancer, malignant prostate cancer, pancreatic cancer, gastric cancer, brain metastasis and melanoma, and lung cancer brain metastasis. Tumors expressing MMP-2 have increased vasculature at the brain-tumor interface, indicating that MMP-2 plays a role in enhancing invasion and vascularization within the central nervous system. Therefore, selective MMP-2 inhibition can be a targeted therapy for the treatment of brain metastasis.

Example 3

MMP-9 is Detrimental, MMP-8 is Beneficial, and MMP-2 is not Involved in Diabetic Wound Healing The incidence of diabetes mellitus is increasing. In 2010, 8.3% of the population in the United States had diabetes (approximately 25.8 million Americans). Two years later, the percentage increased to 9.3% (29.1 million people). A complication of diabetes is the inability of wounds to heal, which results in greater than 60% of non-traumatic limb amputations occurring in individuals with diabetes. The number of lower-limb amputations was 65,700 in 2006, increasing to 73,000 in 2010.

Wound healing involves four stages: hemostasis, inflammation, proliferation, and remodeling. During hemostasis, blood vessels are constricted and a fibrin clot is formed. The fibrin clot releases pro-inflammatory cytokines and growth factors, followed by infiltration of neutrophils, macrophages, and lymphocytes. Neutrophils release reactive oxygen species and matrix metalloproteinases (MMPs), while macrophages induce apoptotic cells. As apoptotic cells are cleared, angiogenesis is stimulated to promote re-epithelialization. Collagen is produced, as well as extracellular matrix (ECM) components, leading to remodeling and wound closure. Any disruption, abnormality, or prolongation in this process leads to delayed wound healing or a chronic wound.

MMPs are a family of 26 proteinases that are zinc-dependent and degrade the ECM. MMPs play an important role in wound healing, cleaving excess ECM, as well as proteolytically process chemokines and cytokines. Normally, MMP activity is regulated by complexation with tissue inhibitors of matrix metalloproteinases (TIMPs). However, in chronic wounds MMP activity is dysregulated and the elevated levels of MMPs contribute to excessive degradation of the ECM and lead to a stalled wound healing process.

We recently reported on the identification of MMP-8 and MMP-9 in wounds of diabetic mice (Gooyit et al., ACS Chem. Biol. 2014, 9, 505-510). We used an inhibitor-tethered resin that binds only to active MMPs, to the exclusion of MMP zymogens and TIMP-complexed MMPs. Using this resin we did not detect MMP-2, however we observed an active MMP-2 band by gelatin zymography, suggesting that MMP-2 was in complex with TIMP. MMP-2 and MMP-9 have been reported in wounds of diabetic patients and diabetic mice. In these studies, the levels of the gelatinases were determined by ELISA, gelatin zymography, mRNA, and Western blot. However, these methods cannot distinguish between active gelatinases and TIMP-complexed gelatinases (inactive forms). Sodium dodecyl sulfate is used in gelatin zymography, which denatures the inactive TIMP-MMP complex and results in the appearance of active MMP bands. As such, the MMP-2 reported in wounds of diabetic patients and diabetic mice could in fact be inactive MMP-2 complexed with TIMP.

We recently designed and synthesized a selective MMP-2 inhibitor (compound 1x); this compound inhibits MMP-2 as a slow-binding inhibitor with a $K_i$ value of 440±60 nM and poorly inhibits or does not inhibit other MMPs, including MMP-8 ($K_i$=17,000±2,000 nM) and MMP-9 (28% inhibition at 50,000 nM) (Gooyit et al., J. Med. Chem. (2013) 56, 8139-8150). The residence time for compound 1x bound to MMP-2 is 24.5 min, which is significantly longer than those of TIMP-1 and TIMP-2 bound to MMP-2 of 6.9 and 10.4 min, respectively. Thus, compound 1x is more effective at inhibiting MMP-2 than TIMPs.

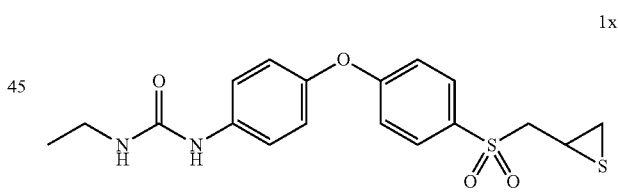

1x

Figure 7:
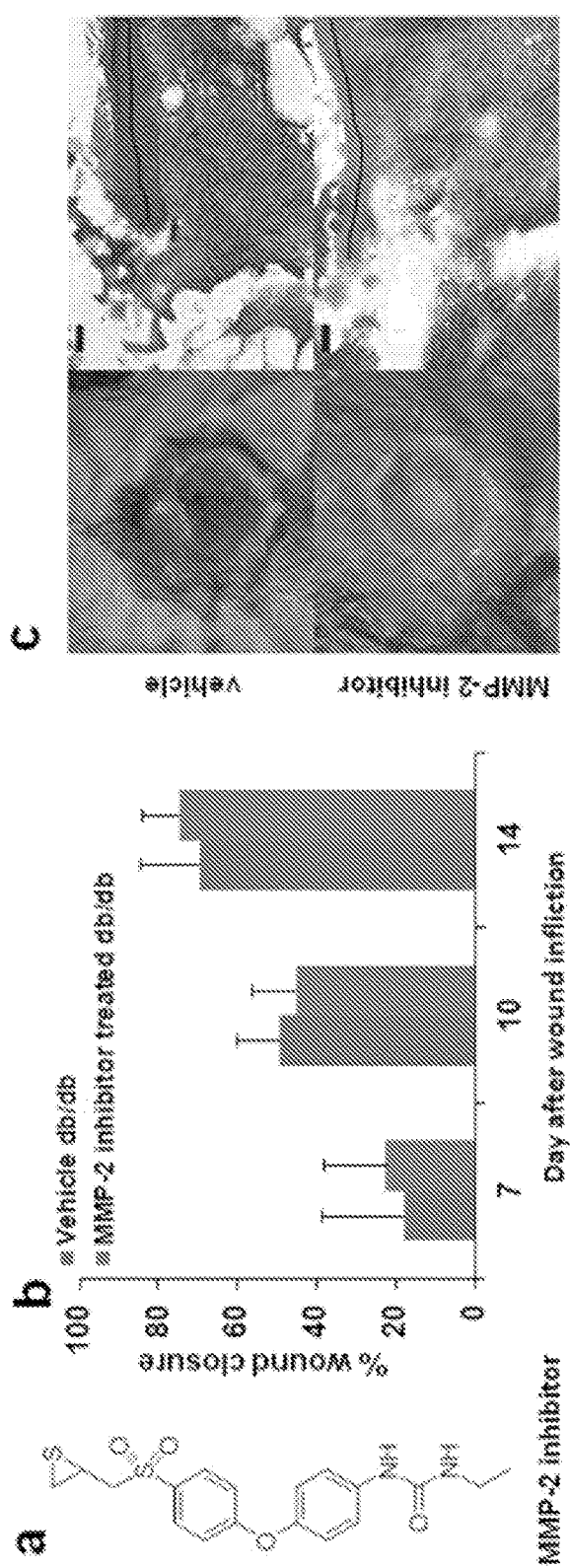
FIG. 7. Inhibition of MMP-2 has no effect on wound healing in diabetic (db/db) mice. Mice were given a single 8-mm punch biopsy lesion on the skin in the dorsal thorax under isoflurane anesthesia. One day later, wounds were treated with MMP-2 inhibitor (0.25 mg/wound/day) or vehicle (20% DMSO/80% propylene glycol). (a) Wound healing in db/db mice treated with MMP-2 inhibitor or vehicle. Mean±SD; n=12, 6, and 6 on days 7, 10, and 14, respectively. (b) Representative wound images of vehicle-treated and MMP-2 inhibitor-treated mice. No differences were observed between the groups. (c) Representative hematoxylin and eosin (H&E) staining of wounds on day 14. Re-epithelialization is indicated by the black line. Scale bars are 50 μm.

We used compound 1x to determine the effect of inhibiting MMP-2 on diabetic wound healing. No significant differences were observed in MMP-2 inhibitor-treated and vehicle groups (day 7: 23±16% vs 18±21%, n=12,p=0.7; day 10:45±11% vs 50±11%, n=6, p=0.5; day 14: 70±15% vs 75±9%, n=6, p=0.5, FIGS. 7a and 7b). Partial re-epithelialization was observed in both MMP-2-inhibitor-treated and vehicle-treated groups (FIG. 7c). Hence, selective inhibition of MMP-2 has no effect in diabetic wound healing. This study confirmed that MMP-2 plays no role in diabetic wound healing. Unfortunately, the role of MMP-2 in diabetic wound healing could not be confirmed with a study in MMP-2 knockout mice, as ablation of MMP-2 results in a compensatory increase in MMP-9, making it difficult to ascertain its role by this method.

Figure 8:
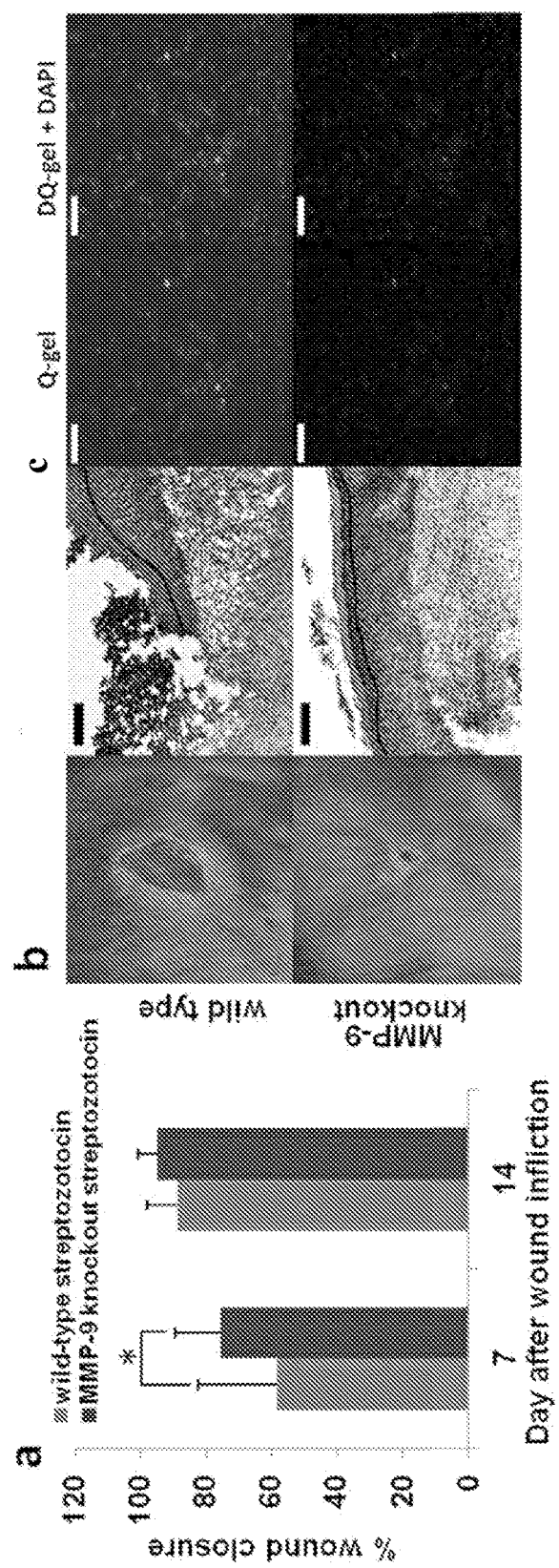
FIG. 8. Ablation of MMP-9 accelerates wound healing. Diabetes was induced by intraperitoneal administration of streptozotocin at 150 mg/kg, as confirmed by measurement of fasting blood glucose of >300 mg/dL. Wounds were inflicted two weeks later. (a) Wound healing in MMP-9 knockout and wild-type streptozotocin-induced diabetic mice. Mean±SD; n=14 and 7 on days 7 and 14, respectively; *p<0.05 indicates statistically significant differences in wound healing between MMP-9 knockout and wild-type streptozotocin-induced diabetic mice. (b) Representative wound images (left, all to the same scale, day 7) and H&E staining (right, day 14). Re-epithelialization is indicated by the black line. (c) In-situ zymography with fluorogenic substrate DQ-gel (DQ-gelatin, green in left panels) merged with nuclear DNA staining by DAPI (blue in right panels); scale bars in panels (c) and (d) are 50 μm. Gelatinase activity in wounds was diminished in MMP-9 knockout mice, as evidenced by significantly decreased fluorescence (lower left).
Figure 9:
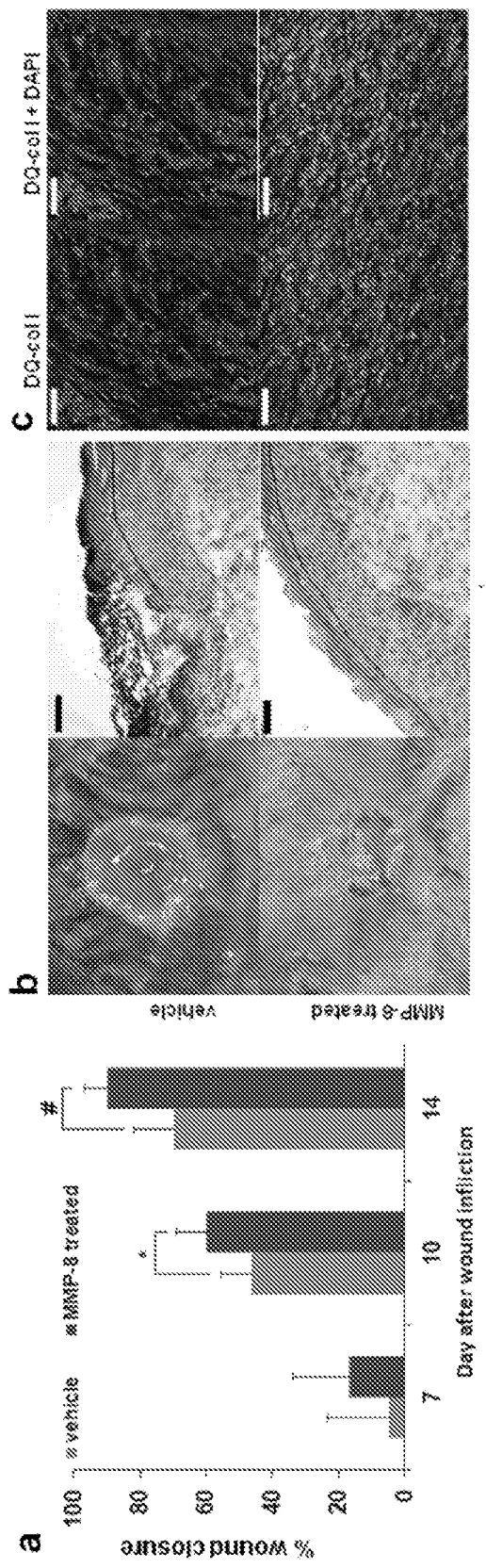
FIG. 9. Topical treatment with exogenously added MMP-8 accelerates wound healing in diabetic (db/db) mice, and can be combined with the compounds described herein for using the methods described herein. A single 8-mm punch biopsy lesion on the skin in the dorsal thorax was given to mice under isoflurane anesthesia. Wounds were treated with MMP-8 (1 μg/wound/day) or vehicle (saline). (a) Wound healing in db/db mice treated with MMP-8 or saline. Mean±SD; n=12, 6, and 6 on days 7, 10, and 14, respectively; *p<0.05 and #p<0.01 indicate statistically significant differences in wound healing between MMP-8-treated and vehicle-treated diabetic mice. (b) Representative wound images (left, all to the same scale) and H&E staining (right, day 14). Re-epithelialization is indicated by the black line. (c) In-situ zymography with MMP fluorogenic substrate DQ-col I (DQ-collagen, green in left panels) merged with nuclear DNA staining by DAPI (blue in right panels). Scale bars in panels b and c are 50 μm. Topical treatment of MMP-8 enhanced the MMP-8 activity in the wounds, as evidenced by the increment of fluorescence (lower left).
Figure 10:
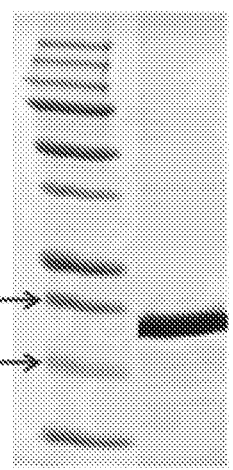
FIG. 10. Gel showing the purification of *Mus musculus* MMP-8.

We had previously shown that MMP-9 was detrimental to diabetic wound healing by selective chemical inhibition (Gooyit et al., *J. Med. Chem.* (2013) 56, 8139-8150). To confirm the detrimental role of MMP-9 in diabetic wound healing, we used MMP-9 knockout mice. We induced diabetes in the animals with streptozotocin. Streptozotocin is highly toxic to the insulin-producing beta cells of the pancreas and produces an animal model for type 1 diabetes (Szkudelski, *Physiol. Res.* (2001) 50, 537-546). Streptozotocin treatment (150 mg/kg given intraperitoneally) reliably induces diabetes in two weeks, as confirmed with fasting blood glucose levels of >300 mg/dL. Diabetes was also induced with streptozotocin in wild-type mice of the same background as the controls. Significant differences in wound healing between MMP-9 knockout and wild-type streptozotocin-induced diabetic mice were observed on day 7 (76±14% vs 58±24%, n=14, p<0.05, FIGS. 8a and 8b). On day 14, wound closure in MMP-9 knockouts was lower than in wild-type mice, although it was not statistically significant (95±6% vs 89±9%, n=7, p=0.15, FIG. 8a). Partial re-epithelialization was seen in wild-type streptozotocin-induced diabetic mice (FIG. 8b, upper right), however re-epithelialization was complete in MMP-9 knockout streptozotocin-induced diabetic mice (FIG. 8b, lower right). In-situ gelatin zymography showed the absence of gelatinase activity in wounds of MMP-9 knockout mice, as evidenced by considerable decrease in fluorescence intensity (FIG. 8c, lower left). Altogether, we conclude that gene ablation of MMP-9 accelerates wound healing in diabetic mice. These results confirmed that MMP-9 is detrimental to wound healing.

We used a uniquely versatile inhibitor-tethered resin for identification of active MMP-8 and MMP-9 in both diabetic and non-diabetic wounds, and showed that the levels of the latter were elevated at statistically significant levels only in diabetic wounds. Working with the hypothesis that MMP-9 is detrimental to healing of diabetic wounds, but that MMP-8 likely plays a beneficial effect, we inhibited MMP-9 selectively by the use of ND-322. The diabetic wounds healed more rapidly in a process that involved re-epithelialization of the wounds, as is the case for the non-diabetic wounds in wild-type mice. In addition, apoptosis was significantly attenuated. We also used a selective MMP-8 inhibitor and showed that healing of the diabetic wounds was delayed, accompanied by decreased re-epithelialization, and undiminished apoptosis. The present study reveals a beneficial effect of selective inhibition of MMP-9 in healing of diabetic wounds. Whereas the use of the selective inhibitor ND-322 does not show any effect on non-diabetic wounds—neither detrimental nor beneficial—it is intriguing that the use of the broad-spectrum MMP inhibitor ilomastat (also known as GM-6001) in non-diabetic wounds in rats, pigs, and humans delayed wound closure and diminished epithelialization. These findings reveal that broad inhibition of the "good" and the "bad" MMPs simultaneously is detrimental to the wound-healing process. Clinical management of diabetic wounds presently involves merely debridement of the wound and attempts at keeping it clean and free of infection. The selective MMP-9 inhibition strategy that we have disclosed here is a first potential pharmacological intervention in treatment of diabetic wounds, which holds great promise in addressing an unmet medical need.

Methods

Synthesis of Compound 1x.

The selective MMP-2 inhibitor (compound 1) was prepared by our methodology as described earlier (Gooyit et al., *J. Med. Chem.* (2013) 56, 8139-8150) and dissolved in 20% DMSO/80% propylene glycol at a concentration of 5.0 mg/mL. The dosing solution and respective vehicle solution were sterilized by passage through a 0.2 µm, 13 mm diameter PTFE membrane connected to an Acrodisc syringe filter (Pall Life Sciences).

Animals.

Female mice were obtained from the Jackson Laboratory and provided with Laboratory 5001 Rodent Diet (PMI) and water ad libitum. Mice were kept in polycarbonate shoebox cages with hardwood bedding at 72±2° F. and a 12:12 h light/dark cycle.

Mouse Diabetic Wound Model.

The excisional mouse diabetic model validated by Sullivan et al. was used (Sullivan et al., *Plast. Reconstr. Surg.* (2004) 113, 953-960). The procedure for inflicting the wounds (single 8 mm wound on the dorsal region) was the same as described previously (Gooyit et al., *ACS Chem. Biol.* (2014) 9, 505-510). Wounds were photographed and covered with a sterile 3M Tegaderm™ transparent dressing (Butler Schein Animal Health, Inc.).

MMP-2 Inhibitor Study.

Female diabetic db/db (BKS.Cg-Dock7m+/+ Leprdb/J, 8-weeks old, 38±3 g, n=24) were used for this study. Wounds were inflicted as described. Treatment with the MMP-2 inhibitor (50 µL of 5.0 mg/mL in 80% propylene glycol/20% DMSO, equivalent to 0.25 mg per wound) or vehicle (50 µL of 80% propylene glycol/20% DMSO) was started one day after wound infliction and continued once a day for 14 days. Digital photographs of wounds were taken on days 0, 7, 10, and 14 while the animals were under isoflurane anesthesia. On day 14, all mice were sacrificed. The wounds were excised, embedded in optimal cutting temperature (OCT) compound, and cryosectioned for histological evaluation.

MMP-9 Knockout Study.

Female MMP-9 knockout mice (B6.FVB(Cg)-9$^{tm1Tvu}$/J, 8-weeks old, 19±2 g, n=14) and wild-type mice (C57BLKS/6J, 8-weeks old, 19±2 g, n=14, same background as MMP-9 knockout mice) were used. The mice were acclimated to the study room for one week prior to commencement of the study. Diabetes was induced by intraperitoneal injection of streptozotocin (Sigma) at 150 mg/kg. Streptozotocin was dissolved in 100 mM sodium citrate buffer (pH 4.5) and administered within 15 min after preparation. After streptozotocin treatment, the mice were housed in disposable cages and given 10% sucrose water to drink for two days. The fasting blood glucose levels were determined two days after streptozotocin treatment. Animals with blood glucose greater than 300 mg/dL were considered diabetic. Animals with blood glucose less than 300 mg/dL received a second dose of streptozotocin one week later. Wounds were inflicted as described and digital photographs were taken on days 0, 7, and 14. Mice (n=7 per group) were sacrificed on days 7 and 14, the wounds were excised, embedded in OCT compound, and cryosectioned for histological evaluation.

Cloning, Purification, and Kinetic Analysis of *Mus Musculus* MMP-8.

The catalytic domain (304-852 bp) of MMP-8 was optimized for expression in *Escherichia coli* and synthesized from GenScript (Piscataway, N.J.) with unique NdeI and XhoI restriction sites flanking the gene at the 5' and 3' termini, respectively. The gene was then cloned into vector pET28a. The construct was transformed into *E. coli* DH5α and verified for the correct insert using NdeI and XhoI double digestion of extracted plasmids and further verified by sequencing of both DNA strands. The purification procedures of recombinant MMP-8 were modified from previously published methods (Tkalcevic et al., *Toxicol. Pathol.* (2009) 37, 183-192). The verified construct was transformed into E. coli BL21 (DE3) cells. The expression of MMP-8 was induced by addition of 0.5 mM isopropyl β-D-1-thiogalactopyranoside at 20° C. Cells were harvested 20 hours later, re-suspended in buffer A (200 mM NaCl, 20 mM HEPES, pH 7.5), and sonicated on ice. The lysed cells were centrifuged for 5 min at 20,000 g. The pellet was gently washed with buffer A to remove cellular debris and was suspended in buffer A, centrifuged for 30 min at 20,000 g, and re-suspended in buffer B (6 M urea, 50 mM Tris (pH 8.5), 5 µM $ZnCl_2$). Undissolved debris was removed by 30-min centrifugation at 20,000 g. The supernatant was loaded onto a Q Sepharose column equilibrated in buffer B. A linear gradient of 0 to 1 M NaCl was used to elute the protein. The fractions with the desired protein were pooled and prepared for dialysis by diluting the protein to an absorbance of 0.3 at 280 nm and increasing the concentration of urea from 6 M to 8 M and the concentration of $ZnCl_2$ from 5 µM to 50 µM.

Three steps of dialysis were performed. First, dialysis was performed twice in 1:5 protein to buffer C (50 mM Tris (pH 8.0), 200 mM NaCl, 100 mM glycine, 10 mM $CaCl_2$, 3 mM $NaN_3$, 50 µM $ZnCl_2$), then in 2 L of buffer D (50 mM Tris (pH7.5), 10 mM $CaCl_2$). The protein solution was concentrated with Macrosep® Centrifugal Filters (Pall Life Sciences). The purity of the protein was determined to be ≥95% by SDS-PAGE (FIG. 11). The enzyme concentration was evaluated spectrophotometrically using the extinction coefficient predicted by ProtParam (Gasteiger et al., Protein identification and analysis tools on the ExPASy Server, in *The Proteomics Protocols Handbook*, 2005, Walker, J. M., Ed., pp 571-607, Humana Press) ($\Delta\Sigma_{280}$=19681.6 $M^{-1}$ $cm^{-1}$). Aliquots of the concentrated protein were stored in 50 mM Tris (pH 7.5), 5 mM $CaCl_2$, 300 mM NaCl, 20 µM $ZnCl_2$, 0.5% (w/v) Brij-35, 30% glycerol at −80° C.

The $K_m$, $k_{cat}$, and $V_{max}$ values for the reaction of MMP-8 with the fluorogenic substrate Mca-KPLGL-Dpa-AR-NH2 (R&D Systems) were evaluated in reaction buffer (50 mM Tris (pH7.5), 10 mM $CaCl_2$, 150 mM NaCl, 0.05% (w/v) Brij-35). The substrate was prepared as a 1 mM stock solution in DMSO. Substrate hydrolysis was monitored with excitation at 325 nm and emission at 393 nm with a Cary Eclipse fluorescence spectrophotometer (Varian). A standard curve was constructed at various concentrations of the full hydrolyzed substrate for calibration. Initial velocities were obtained from plots of fluorescence versus time. The slope from these plots was divided by the fluorescence change corresponding to complete hydrolysis and then multiplied by the substrate concentration to obtain initial velocity in units of second ($s^{-1}$). The parameters $k_{cat}$ and $K_m$ were determined by nonlinear fitting of the initial velocities, at varying concentrations of the substrate, using the Michaelis-Menten equation. Kinetic analysis resulted in $K_m$=4.5±0.5 µM, $V_{max}$=1.07±0.03 nM s-1, $k_{cat}$=0.54±0.02 s-1, $k_{cat}/K_m$=1.19×$10^5$ $M^{-1}$ $s^-$, activity=926 pmol/min/µg. The catalytic efficiency of the purified MMP-8 was high compared to other commercial available MMPs.

Exogenous MMP-8 Study.

Female diabetic db/db (BKS.Cg-Dock7m+/+ Leprdb/J, 8-weeks old, 38±3 g, n=24) were used for this study. Wounds were inflicted and the following day the wounds were treated topically with MMP-8 (50 µL of 20 µg/mL MMP-8 in reaction buffer) or vehicle (50 µL reaction buffer) once a day for 14 days. The reaction buffer consisted of 50 mM Tris (pH 7.5), 10 mM $CaCl_2$, 150 mM NaCl, and 0.05% (w/v) Brij-35. Digital photographs of the wounds were taken on days 0, 7, 10, and 14 while animals were under isoflurane anesthesia. On days 7 and 14, 12 mice (n=6 per group) were sacrificed. The wounds were excised, embedded in OCT compound, and cryosectioned for histological evaluation.

Wound Measurements.

Photographs were taken using the procedure described by Gooyit et al. (*ACS Chem Biol*. (2014) 9, 505-510) at a fixed distance above the wounds and calibrated using a ruler included in the photographic frame. Image J 1.48c software was used to calculate wound areas. The percentage of wound closure was calculated from the wound area on the specified day relative to that on day 0.

Histological Evaluation, Apoptosis Detection, and In-Situ Zymography.

Fresh wound tissue was harvested and embedded in OCT compound. Subsequently, the tissue was cryosectioned for H&E staining (12-µm thickness) and for apoptosis assays and in-situ zymography (8-µm thickness). Re-epithelialization was assessed on a Nikon Eclipse 90i Fluorescent Microscope (Nikon Instruments Inc.) as described earlier (Tkalcevic et al., *Toxicol. Pathol*. (2009) 37, 183-192). Apoptosis was evaluated using Derma TACS™ Apoptosis detection kits (Trevigen, Inc.) according to the manufacturer's instructions. The protocol of in-situ zymography was adapted from known methods. Gelatinolytic activity was detected in unfixed cryostat sections using DQ-gelatin as a substrate. DQ-gelatin was prepared at a concentration of 20 µg/mL in Tris-buffered saline (TBS) buffer (50 mM TBS pH 7.6, 1 mM $CaCl_2$). A general MMP inhibitor in 0.5 mM EDTA was prepared as a negative control. Cryostat sections were air-dried for 10 min and incubated in the substrate mixture in the presence and absence of EDTA for 1 hr at room temperature. After the incubation period, the slides were washed in PBS (three times, 5 min each), fixed with 4% paraformaldehyde in PBS for 10 min in the dark, washed again with PBS (three times, 5 min each), incubated in the dark for 5 min with 300 nM DAPI solution, and mounted with anti-quenching mounting medium. Fluorescence of FITC was detected with excitation at 460-500 nm and emission at 512-542 nm. DAPI was detected with excitation at 340-380 nm and emission at 425-∞ nm.

Statistical Analyses.

Data are expressed as mean±SD. Wound healing between the groups in the studies were analyzed for statistical significance using a paired Student t-test, where p<0.05 was considered statistically significant.

Example 4

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| Tablet 1 | mg/tablet |
| --- | --- |
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

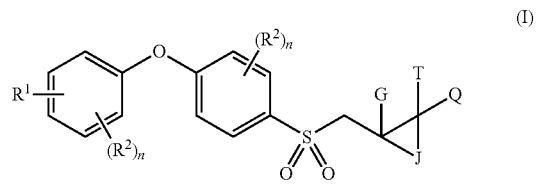

wherein
R$^1$ is —CH$_2$—NHR$^a$ wherein R$^a$ is H or (C$_1$-C$_6$)alkanoyl; —NH—C(═NH)—NH$_2$; or

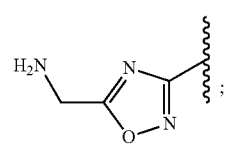 [SMILES: *c1noc(CN)n1]

J is S or O;

G, T, and Q are each independently H, $(C_1$-$C_6)$alkyl, or —CN;

each $R^2$ is independently H, OH, $(C_1$-$C_6)$alkyl, $(C_1$-$C_6)$ alkoxy, $(C_1$-$C_6)$alkanoyl, $(C_1$-$C_6)$alkanoyloxy, aryl, heteroaryl, carboxy, cyano, nitro, halo, trifluoromethyl, trifluoromethoxy, $SR^z$, $SO_2N(R^z)_2$, $NR^zR^z$, or $COOR^z$; wherein each $R^z$ is independently H, $(C_1$-$C_6)$alkyl, $(C_1$-$C_6)$alkanoyl, $(C_6$-$C_{10})$aroyl, aryl, aryl$(C_1$-$C_6)$alkyl, heteroaryl, heteroaryl$(C_1$-$C_6)$alkyl, or optionally a nitrogen protecting group when $R^z$ is covalently bonded to a nitrogen atom; and each n is independently 0, 1, 2, 3, or 4;

or a salt thereof.

2. The compound of claim 1 wherein $R^1$ is —$CH_2$—$NHR^a$.

3. The compound of claim 2 wherein $R^a$ is H or —C(=O)$CH_3$.

4. The compound of claim 1 wherein $R^1$ is —NH—C(=NH)—$NH_2$.

5. The compound of claim 1 wherein $R^1$ is

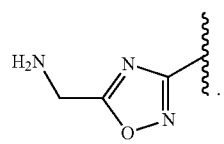 [SMILES: *c1noc(CN)n1]

6. The compound of claim 1 wherein $R^1$ is located at the para position with respect to the oxygen of the phenyl group to which $R^1$ is attached.

7. The compound of claim 1 wherein J is S.

8. The compound of claim 1 wherein G, T, and Q are each independently H.

9. The compound of claim 1 wherein the compound is:

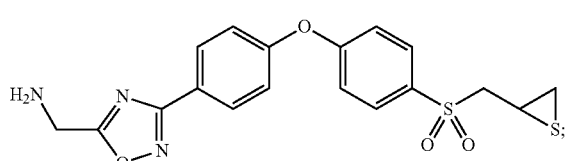

(ND-336, 5)

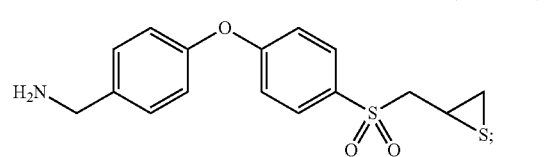

(ND-378, 6)

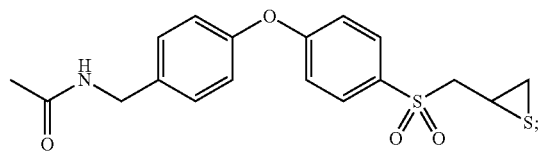

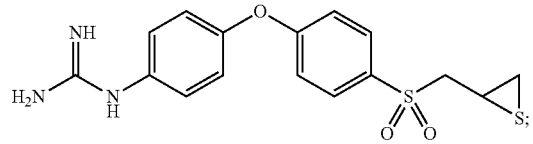

(7)

or a pharmaceutically acceptable salt thereof.

10. The compound of claim 1 wherein the compound is a selective inhibitor of MMP-2, MMP-9, or MMP-14, or a combination thereof.

11. A composition comprising the compound of claim 1 in combination with a pharmaceutically acceptable diluent, excipient, or carrier.

12. A method to inhibit MMP-2, MMP-9, or MMP-14, or a combination thereof, comprising contacting a composition that includes MMP-2, MMP-9, or MMP-14, with a compound of claim 1, thereby inhibiting the enzymatic activity of the matrix metalloproteinase.

13. The method of claim 12 wherein the contacting is in vitro.

14. The method of claim 12 wherein the contacting is in vivo.

15. The method of claim 12 wherein the inhibition is selective for MMP-2 in the presence of MMP-8.

16. The method of claim 12 wherein the inhibition is selective for MMP-9 in the presence of MMP-8.

17. The method of claim 12 wherein the inhibition is selective for MMP-2 in the presence of both MMP-9 and MMP-14.

18. The method of claim 12 wherein the compound is a nanomolar slow-binding inhibitor of MMP-2, MMP-9, and MMP-14, and the compound poorly inhibits MMP-8 in a non-competitive manner.

19. A method to treat a neurological condition comprising administering to a patient having a neurological condition an effective amount of a compound of claim 1 that is effective to treat the neurological condition, thereby alleviating or lessening the symptoms of the condition.

20. The method of claim 19 wherein the neurological condition is stroke; aneurysm; epilepsy; amyotrophic lateral sclerosis (ALS); Alzheimer's Disease; Huntington's disease; Parkinson's disease; HIV-associated dementia; multiple sclerosis; glaucoma; hypoxia; ischemia; reperfusion injury; head trauma; or spinal cord injury.

21. A method of accelerating the healing process of a wound comprising administering to a mammal afflicted with a wound an effective amount of a compound of claim 1, or a pharmaceutically acceptable salt thereof, wherein the compound is a selective MMP inhibitor and the healing process of the wound is accelerated.

22. The method of claim 21 wherein epithelialization of tissues adjacent to the wound is enhanced.

23. A method to treat a patient having traumatic brain injury comprising administering to a patient having traumatic brain injury an effective amount of a compound of claim 1 that is effective to treat the traumatic brain injury, thereby lessening the symptoms of the traumatic brain injury.

24. A method for treating traumatic brain injury in a patient in need of such treatment, the method comprising administering to the patient an effective amount of the compound:

or a pharmaceutically acceptable salt thereof.
25. A method for enhancing the healing of a diabetic wound in a patient in need of such treatment, the method comprising administering to the patient an effective amount of the compound:
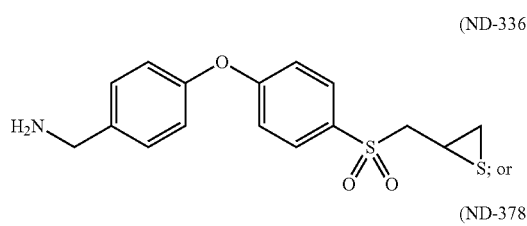
(ND-336, 5)
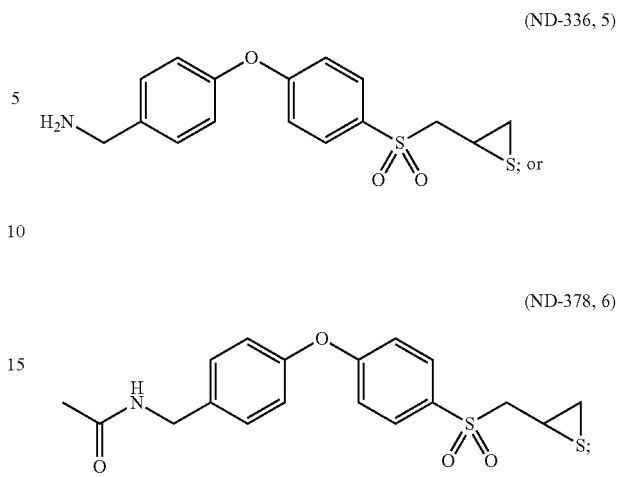
(ND-336, 5)
(ND-378, 6)
or a pharmaceutically acceptable salt thereof.
* * * * *